US006714620B2

(12) United States Patent
Caflisch et al.

(10) Patent No.: US 6,714,620 B2
(45) Date of Patent: Mar. 30, 2004

(54) RADIATION THERAPY TREATMENT METHOD

(75) Inventors: Russel Caflisch, Manhattan Beach, CA (US); Nigel Goldenfeld, Champaign, IL (US); Gennady Gorlachev, Moscow (RU); Pavel Kalugin, Les Ulis (FR); Serguei Mechkov, Montpellier (FR)

(73) Assignee: Numerix, LLC, New York, NY (US)

( * ) Notice: Subject to any disclaimer, the term of this patent is extended or adjusted under 35 U.S.C. 154(b) by 238 days.

(21) Appl. No.: 09/957,397

(22) Filed: Sep. 20, 2001

(65) Prior Publication Data

US 2002/0106054 A1 Aug. 8, 2002

Related U.S. Application Data

(60) Provisional application No. 60/234,538, filed on Sep. 22, 2000, and provisional application No. 60/235,296, filed on Sep. 26, 2001.

(51) Int. Cl.$^7$ ................................................ A61N 5/10
(52) U.S. Cl. ........................................ 378/65; 378/901
(58) Field of Search ............................. 378/64, 65, 901

(56) References Cited

U.S. PATENT DOCUMENTS

| 5,341,292 | A |   | 8/1994  | Zamenhof |
| 5,602,892 | A |   | 2/1997  | Llacer |
| 5,870,697 | A | * | 2/1999  | Chandler et al. ........... 702/179 |
| 6,029,079 | A | * | 2/2000  | Cox et al. .................. 600/407 |
| 6,301,329 | B1| * | 10/2001 | Surridge ....................... 378/65 |
| 6,535,837 | B1| * | 3/2003  | Schach Von Wittenau .. 702/180 |
| 2002/0027971 | A1 | * | 3/2002 | Deasy et al. .................. 378/65 |

FOREIGN PATENT DOCUMENTS

| WO | WO 97/32630 A1 | 9/1997 |
| WO | WO 97/42522 A1 | 11/1997 |
| WO | WO 98/52646 A1 | 11/1998 |
| WO | WO 98/53307 A2 | 11/1998 |
| WO | WO 99/40523 A1 | 8/1999 |
| WO | WO 00/07667 A1 | 2/2000 |

OTHER PUBLICATIONS

Josep Sempau et al., DPM a fast, accurate Monte Carlo code optimized for photon and electron radiotherapy treatment planning dose calculations, Phys. Med. Biol. 45, Feb. 29, 2000; pp. 2263–2291; 2000 IOP Publishing Ltd., UK.

Joseph O. Deasy, Denoising of electron beam Monte Carlo dose distributions using digital filtering techniques; Phys. Med. Biol. 45 (2000) 1765–1779; 2000 IOP Publishing Ltd., UK.

Iwan Kawrakow and Matthias Fippel, Investigation of variance reduction techniques for Monte Carlo photon dose calculation using XVMC, Phys. Med. Biol. 45 (2000) 2163–2183, 2000 IOP Publishing Ltd., UK.

(List continued on next page.)

Primary Examiner—David V. Bruce
(74) Attorney, Agent, or Firm—Foley & Lardner

(57) ABSTRACT

Radiation therapy planning uses a beam commissioning tool and a Monte Carlo dose calculation tool. In the beam commissioning, measured dose data are input into a data processor. The measured dose data are derived from exposing a phantom to radiation from a source; and measuring the radiation dose to obtain a measured dose in the phantom resulting from the exposing step. The dose is measured at a plurality of points within the phantom, at least some of said points being axial points located at positions along a substantially central axis of the radiation source and others of said points being transverse points located at positions along an axis transverse to the central axis. The method further performs a Monte Carlo simulation of the radiation source to determine a simulated dose at the plurality of points; and further models the radiation source using the simulated dose and the measured dose.

104 Claims, 34 Drawing Sheets

OTHER PUBLICATIONS

Jun Deng, Steven B. Jiang, Todd Pawlicki, Jinsheng Li, and C.-M. MA, Derive Electron and Photon Energy Spectra from Electron Central Axis Depth Dose Curves, Phys. Med. Biol. Oct. 5, 2000, pp. 1–40, Stanford, CA.

Luo Zhengming and David Jette, On the possibility of determining an effective energy spectrum of clinical electron beams from percentage depth dose (PDD) data of broad beams, Phys. Med. Biol. 44 (1999) N177–N182, 1999 IOP Publishing Ltd.

J. O. Deasy and P. R. Almond, The spectral dependence of electron central–axis depth–dose curves, Med. Phys. 21, (9), Sep. 1994, pp. 1369–1376, 1994 AM. Assoc. Phys. Med.

B.A. Faddegon and I. Blevis, Electron spectra derived from depth dose distributions, Med. Phys 27, (3) Mar. 2000, pp. 514–526, 2000 Am. Assoc. Phys. Med.

W.R. Nelson and D.W.O. Rogers, Structure and Operation of the EGS4 Code System in Monte Carlo Transport of Electrons and Photons, T.J. Jenkins, W.R. Nelson and A. Rindi, eds., Plenum, 287–305, (1989).

D.W.O. Rogers and A.F. Bielajew, Code Accuracy (Section III, pp. 492–522) in Monte Carlo techniques of electron and photon transport for radiation dosimetry in The Dosimetry of Ionizing Radiation, vol. III, K. Kase, B. Bjangard and F. Attix, ed., Academic Press, 427–539, (1990).

D.W.O. Rogers, B.A.Faddegon, G.X.Ding, C.-M. Ma, J. We and T.R. Mackie, Beam: A Monte Carlo code to simulate radiotherapy treatment units, Medical Physics 22 (1995) 503–524.

C.-M. Ma, B.A. Faddegon, D.W.O. Rogers and T.R. Mackie, Accurate characterization of Monte Carlo calculated electron beams for radiotherapy, Medical Physics 24 (1997) 401–416.

J.J. Demarco, T. D. Solberg and J.B. Smaters, A CT–based Monte Carlo simulation tool for dosimetry planning and analysis, Medical Physics 25 (1998) 1–11.

C.F. Hartmann Siantar, et al., Lawrence Livermore National Laboratory's Peregine Project UCRL–JC–126732 amd in 12$^{th}$ International Conference on the Use of Computers in Radiation Therapy, (1997).

A.F. Bielajw and D.W.O. Rogers, Variance–Reduction Techniques in Monte Carlo Transport of Electrons and Photons, T.J. Jenkins, W.R. Nelson and A. Rindi, eds., Plenum, 407–419, 1989.

D.F. Donoho, De–noising by soft–thresholding, IEEE Transaction Information Theor 41 (1995) 613–627.

L. Rudin and S.J. Osher, Total variation based image restoration with free local constraints, Proceedings of 1$^{st}$ International Conference on Image Processing, Austin, TX, IEEE Comput. Soc. Press, (1994), p. 31–35.

A. L. Ames, D.R. Nadeau and J.L. Moreland (1997) VRML 2.0 Sourcebook Wiley pp. 112–115.

H. A. BEthe (1953), Moliere's theory of mutiple scattering, Phys. Rev. 89, 1256–1266.

W. H. Press, S.A. Teukolsky, W. T. Vetterling and B. P. Flannery, Linear Regularization Methods in Numrical Recipes in C. The Art of Scientific Computing.

T. Holmes and T.R. Mackie (1994) A filtered backprojection dose calculation method for inverse treatment planning, Med. Phys. 21, 303–313.

J. R. Cunningham (1972), Scatter–air ratios, Phys. Med. Biol. 7, 42–51.

T. R. Mackie, J. W. Scrimger and J. J. Battista (1985) A convolution method of calculating dose for 15 MV x–rays, Med. Phys. 12, 188–196.

M. Kalos and P. Whitlock (1986), Monte Carlo Methods vol. Wiley. pp. 92–103 and 107–109.

E. Veach and L. J. Guibas (1995), Optimally combining sampling techniques for Monte Carlo rendering in Computer Graphics Proceedings, SIGGRAPH 95, R. Cook, ed., ACM, 1995. p. 419–28.

K. R. Hogstrom, J.D. Mills AD P.R. Almond (1981) Electron beam dose calculations, phys. Med. Biol. 26, 445.

J. M. Hammersley and D.C. Handscomb, 7.7 Quasi–(that is, Sub–) Random Sequences, 1964, Monte Carlo Methods (London: Methuen), Yu. A. Shreider (ed.) 1966, The Monte Carlo Method (Oxford: Pergamon). Sobol', I.M. 1974, The Monte Carlo Method (Chicago: University of Chicago Press), M. H. Kalos, and P.A. Whitlock, 1986, Monte Carlo Methods (New York: Wiley).

Alex F. Bielajaw and D.W.O. Rogers, Presta: The Parameter Reduced Electron–Step Transport Algorithm for Electron Monte Carlo Transport, Nuclear Instruments and Methods in Physics Research B18 (1987) 615–181.

Moyed Miften, Model, Computerized Medical Systems, Inc. (1999).

Benjamin E. Nelms, Tissue Complication Probability (NT), Computerized Medical Systems, Inc. (1999), 16 pages.

Suzanne Monthofer, Fast Fourier Transform (FFT) Convolu, Computerized Medical Systems, Inc., Jun. 1999, 6 pages.

Focus® Dicom Conformance State, Computerized Medical Systems, Oct. 1998, 16 pages.

* cited by examiner

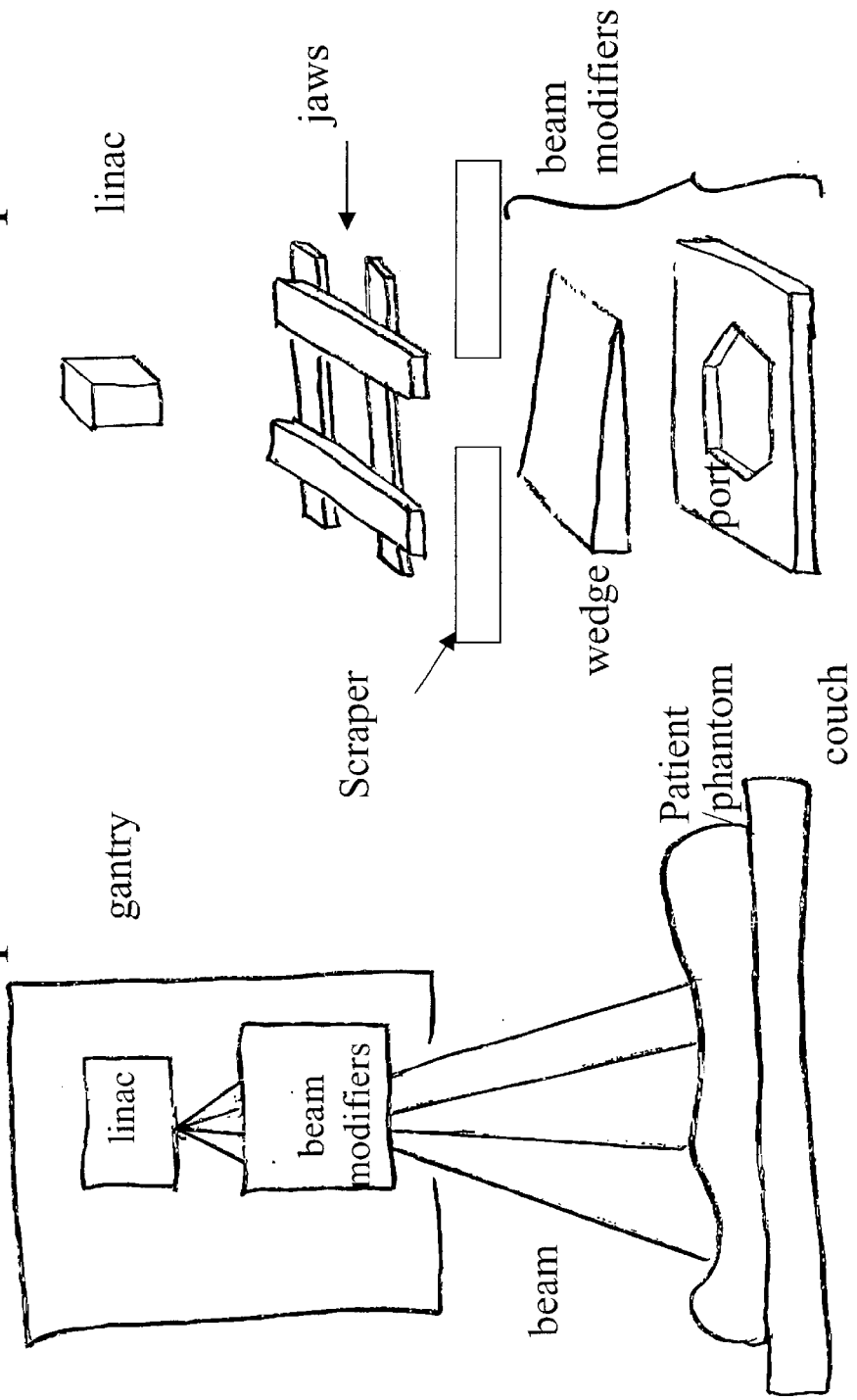
Fig. 1.1 Treatment setup
PRIOR ART
Fig 1.2 Treatment head components
PRIOR ART

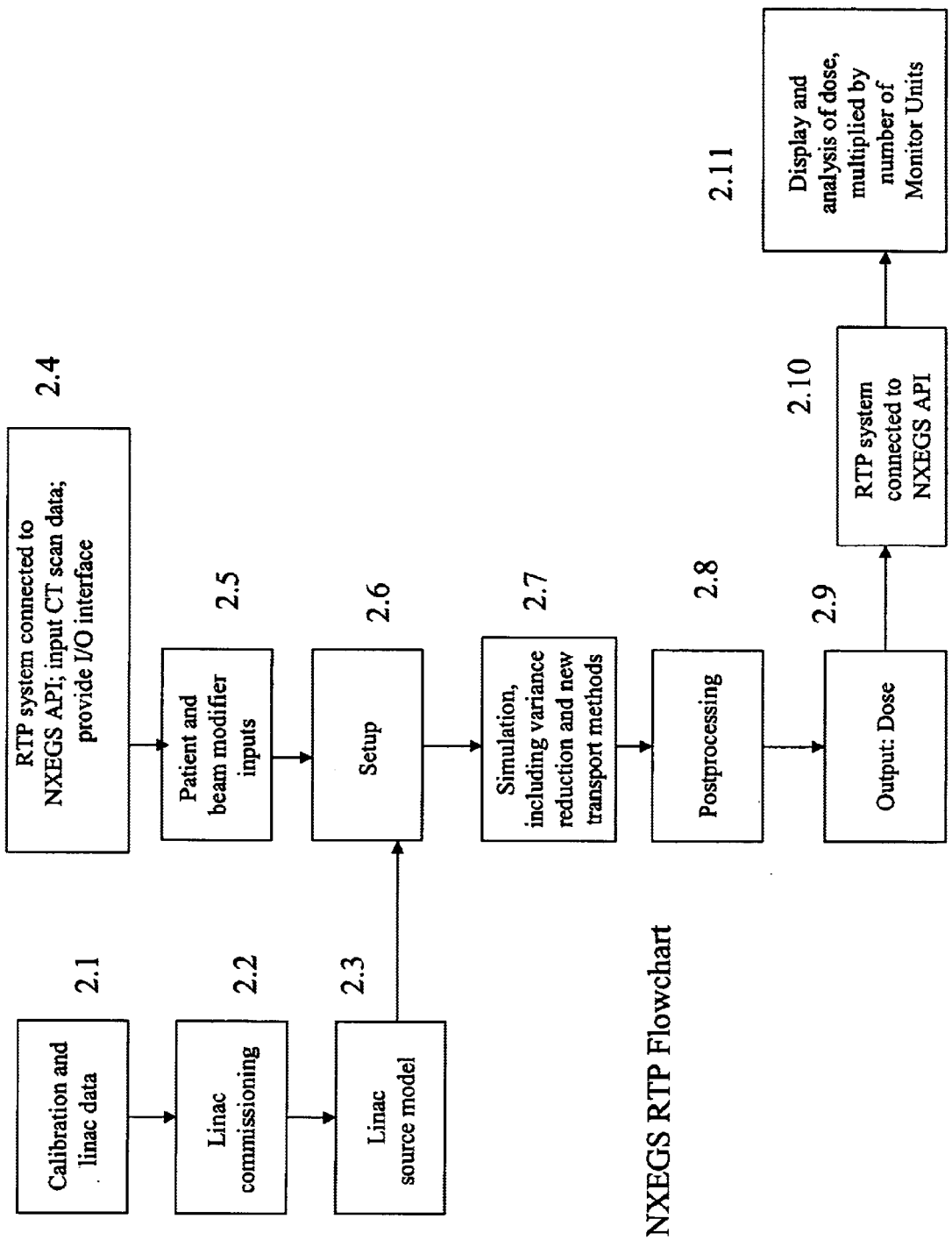
Fig. 2 NXEGS RTP Flowchart

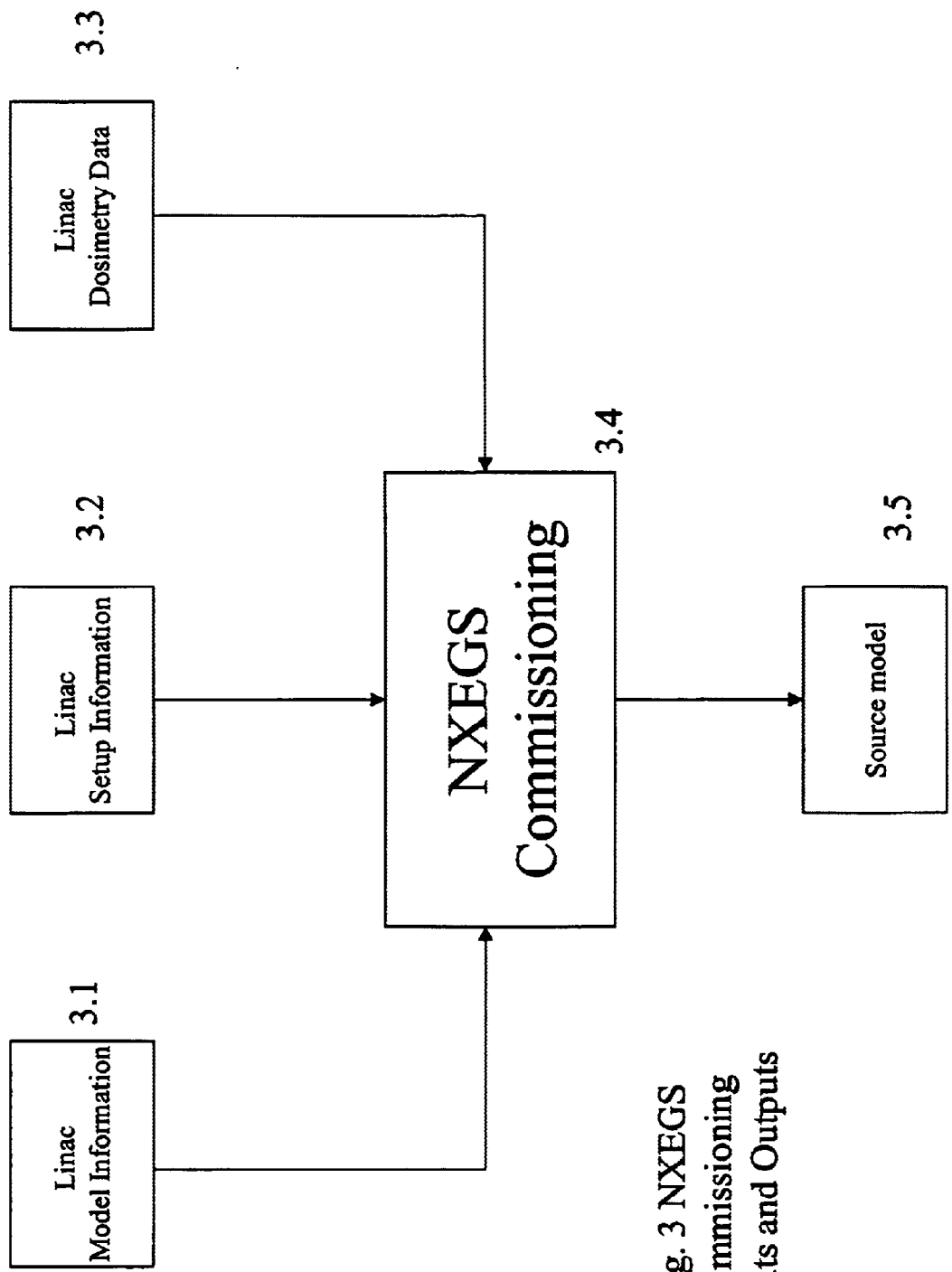
Fig. 3 NXEGS Commissioning Inputs and Outputs

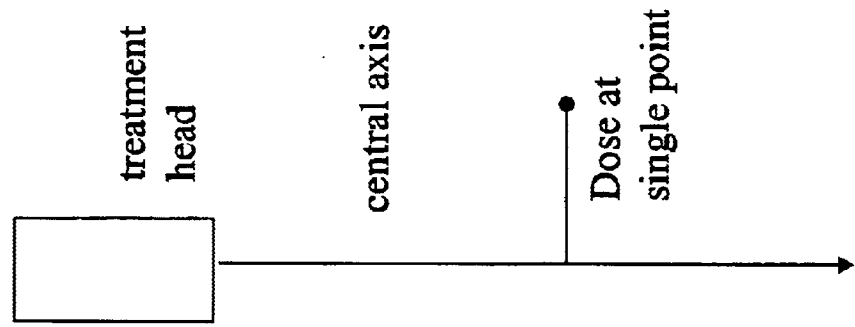
Fig. 4.3 Non-scanning data at single point on central axis
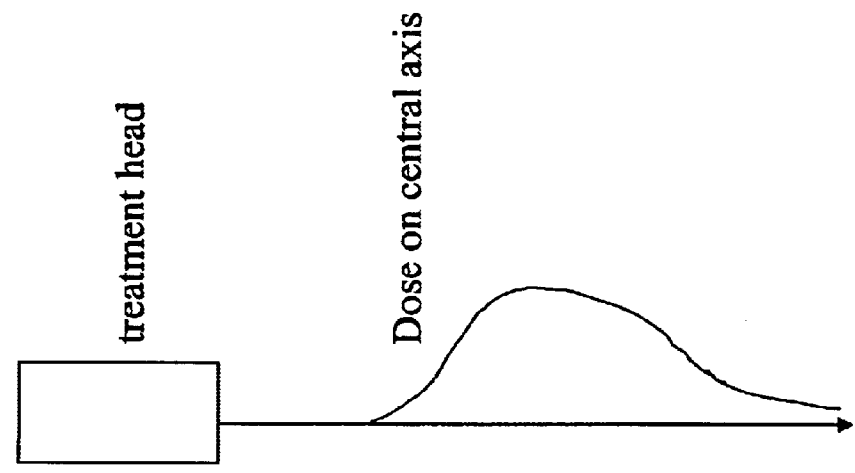
Fig. 4.2 Scanning data on central axis
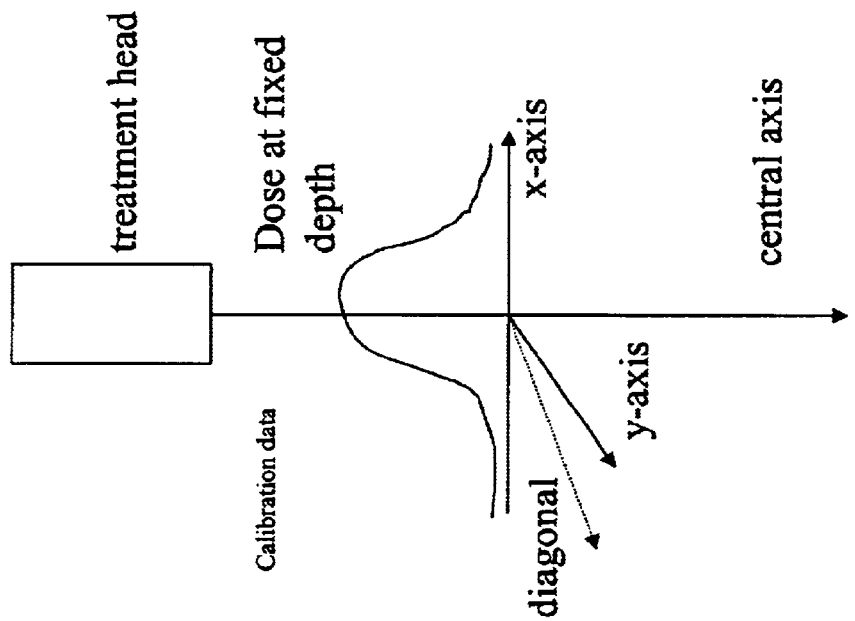
Fig. 4.1 Scanning data on transverse axis (x,y or diagonal)

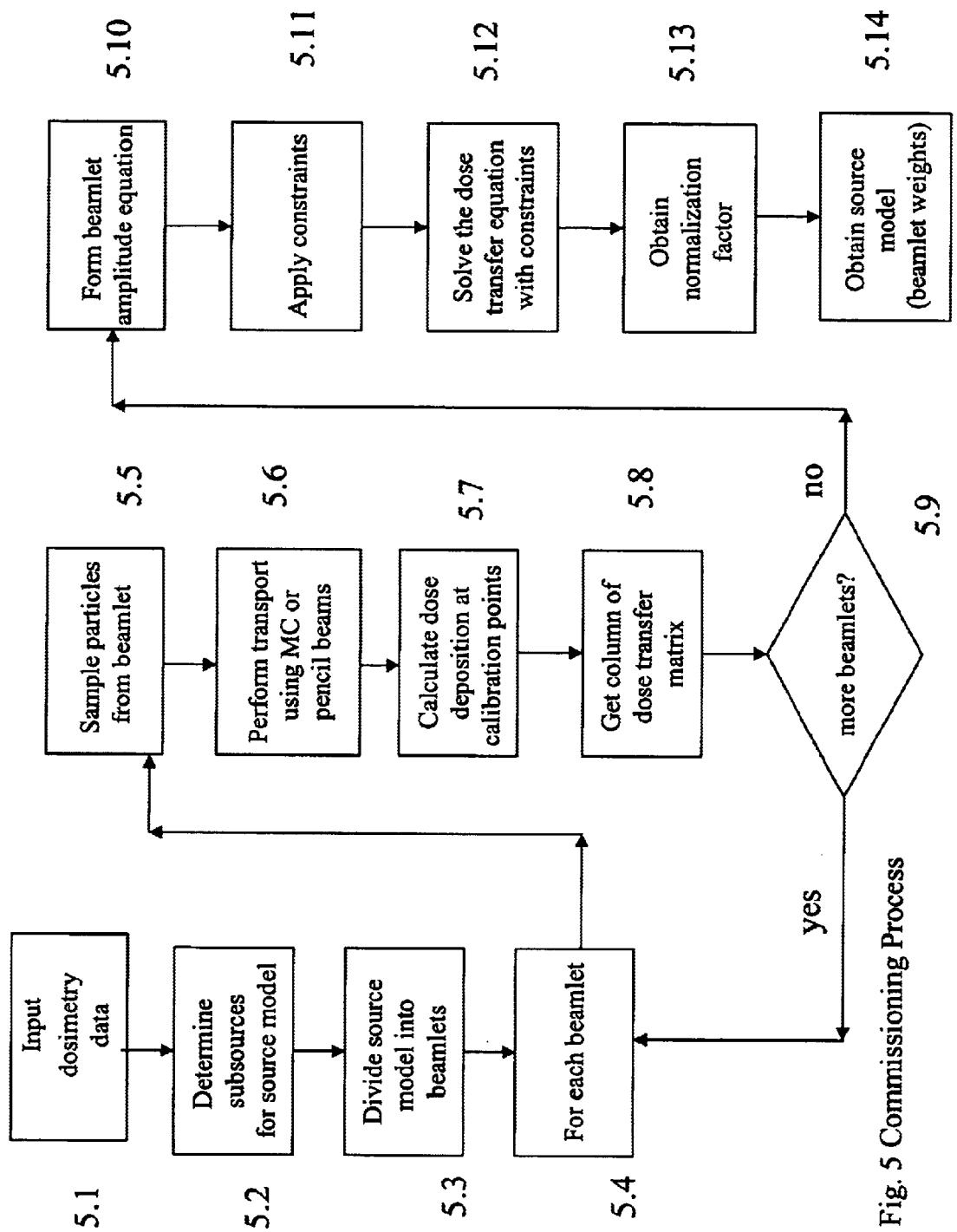
Fig. 5 Commissioning Process

Pencil Beams
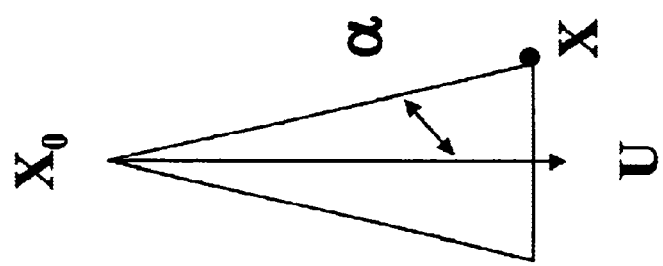
Fig. 6.3 Dose distribution for each pencil beam
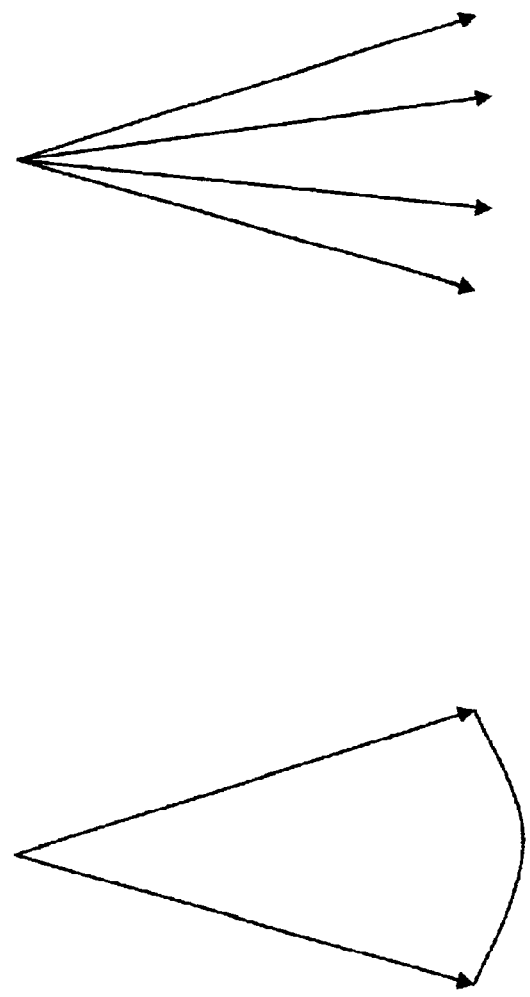
Fig. 6.2 Collection of pencil beams
Fig. 6.1 Continuous beam

Source models
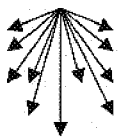 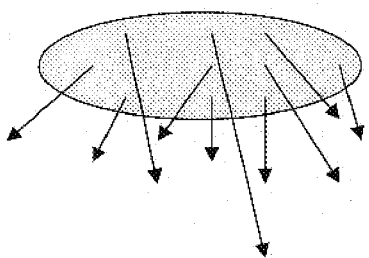
Fig. 7.1 Focal source    Fig. 7.2 Extra-focal source

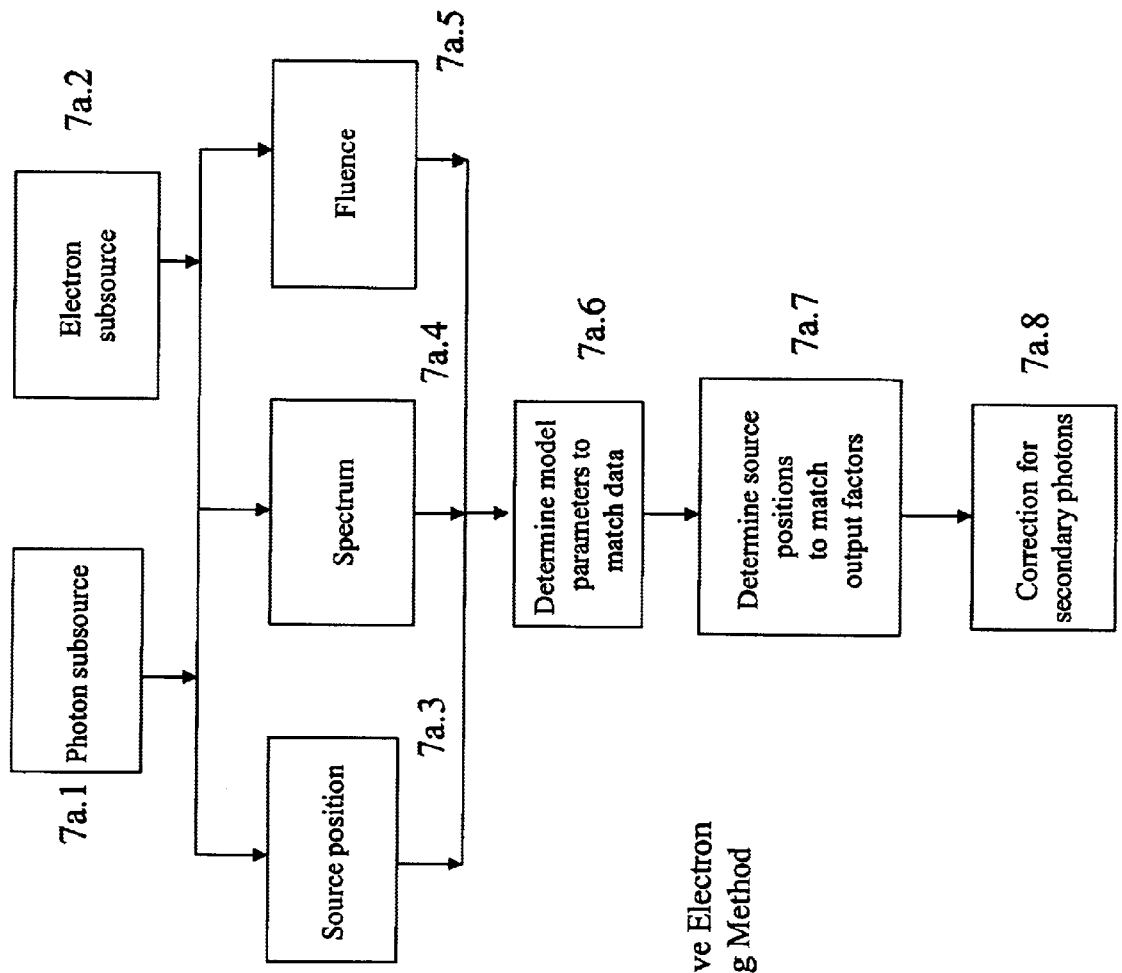
Fig. 7a Alternative Electron Commissioning Method

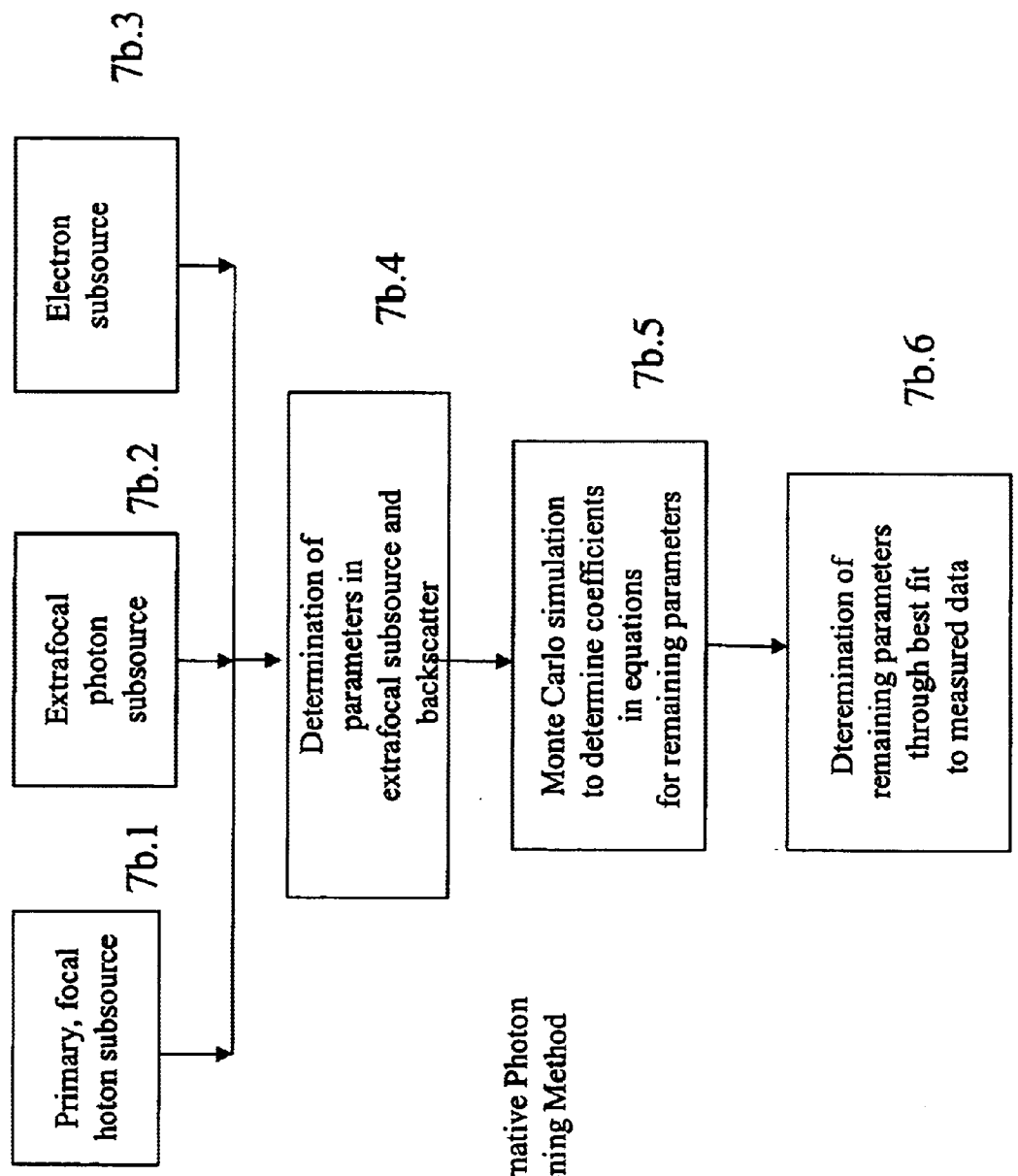
Fig. 7b Alternative Photon Commissioning Method

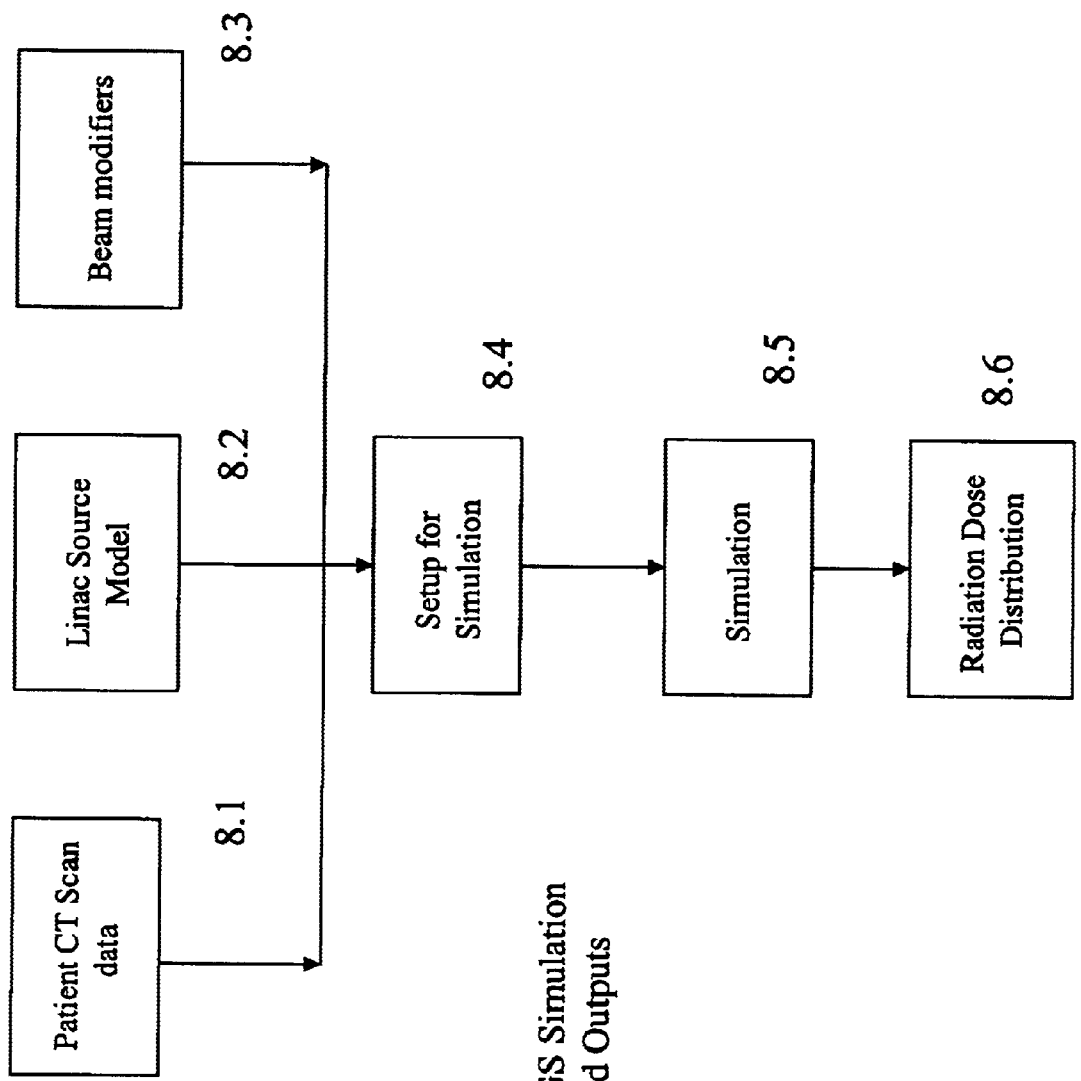
Fig. 8 NXEGS Simulation Inputs and Outputs

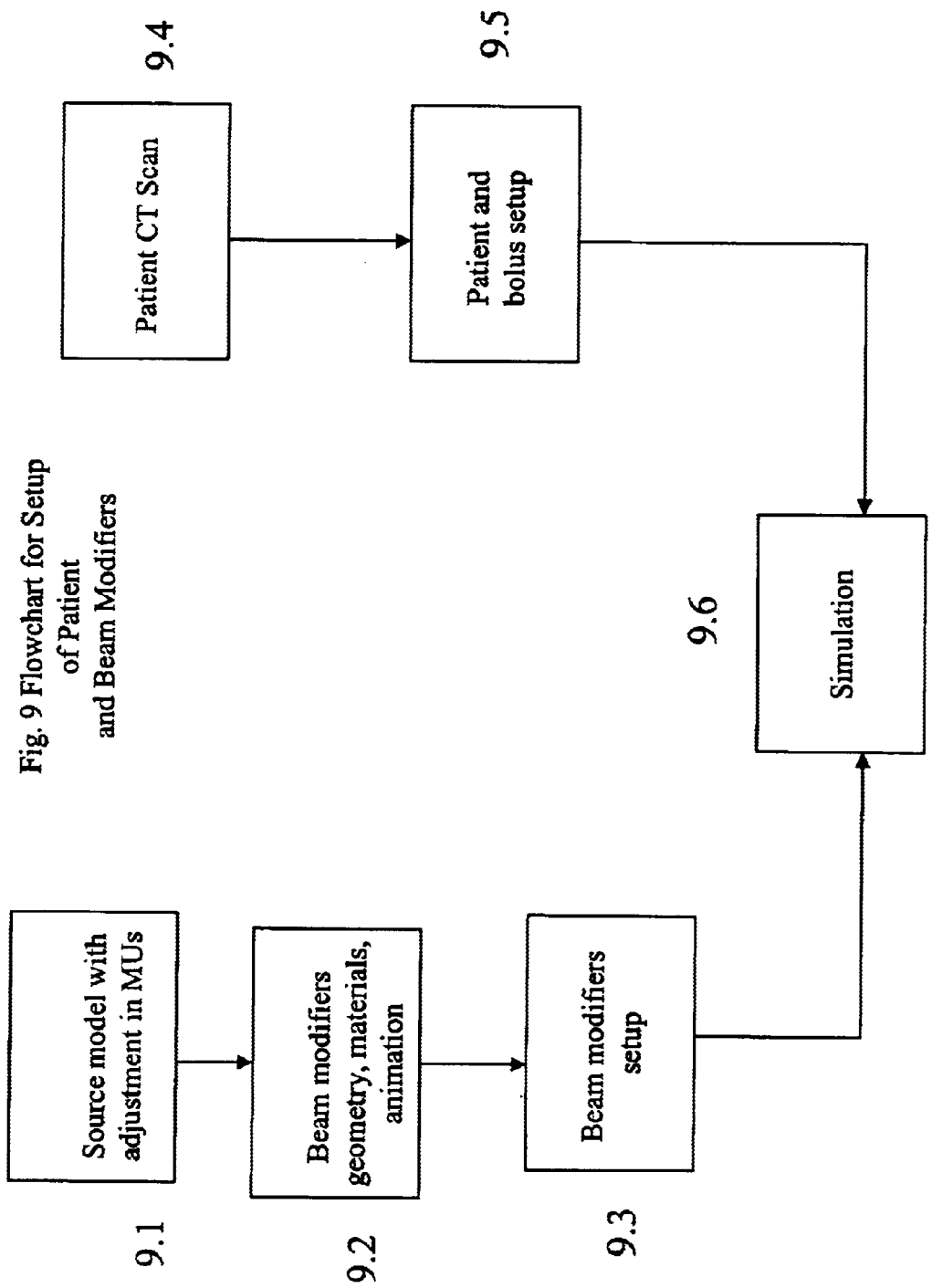

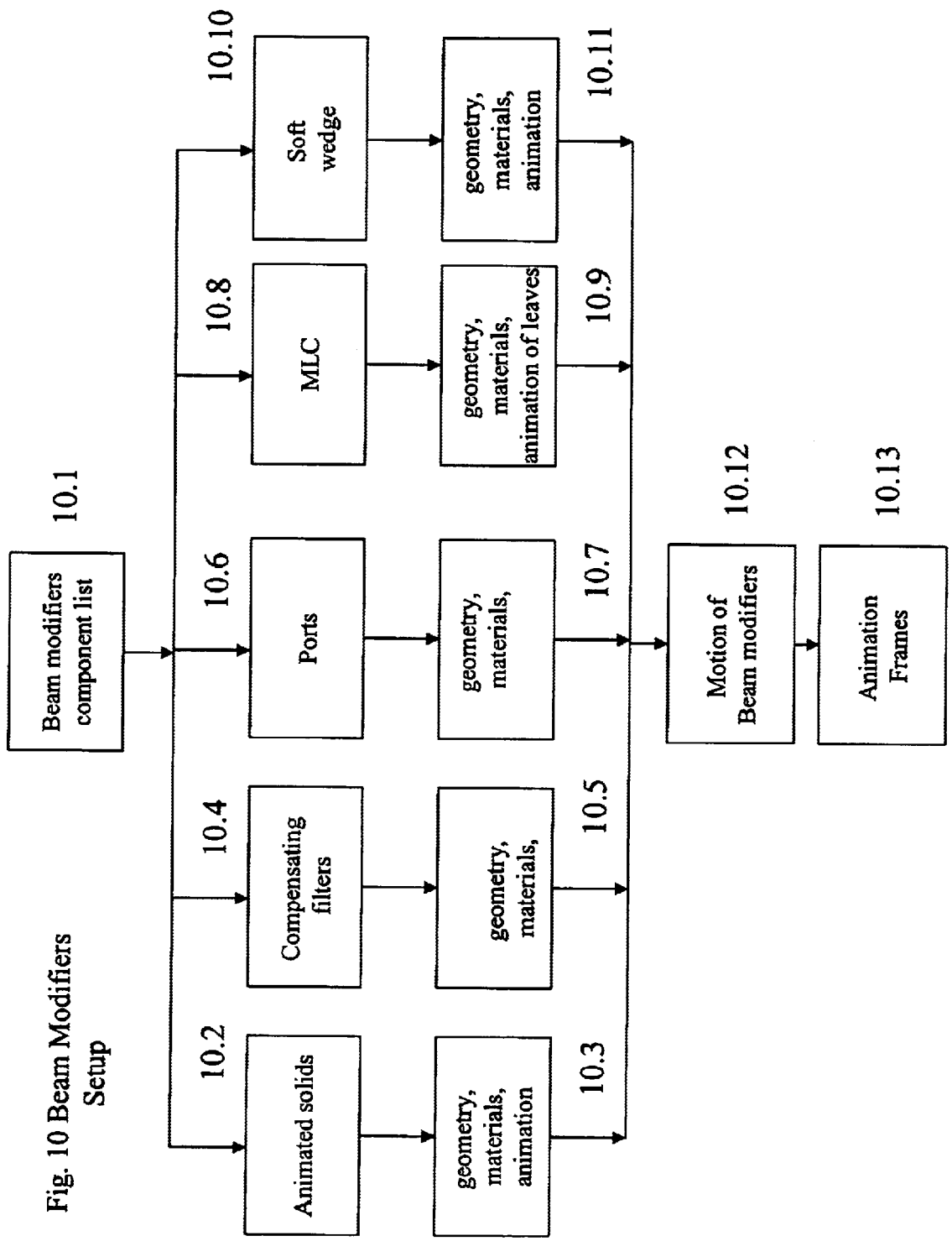
Fig. 10 Beam Modifiers Setup

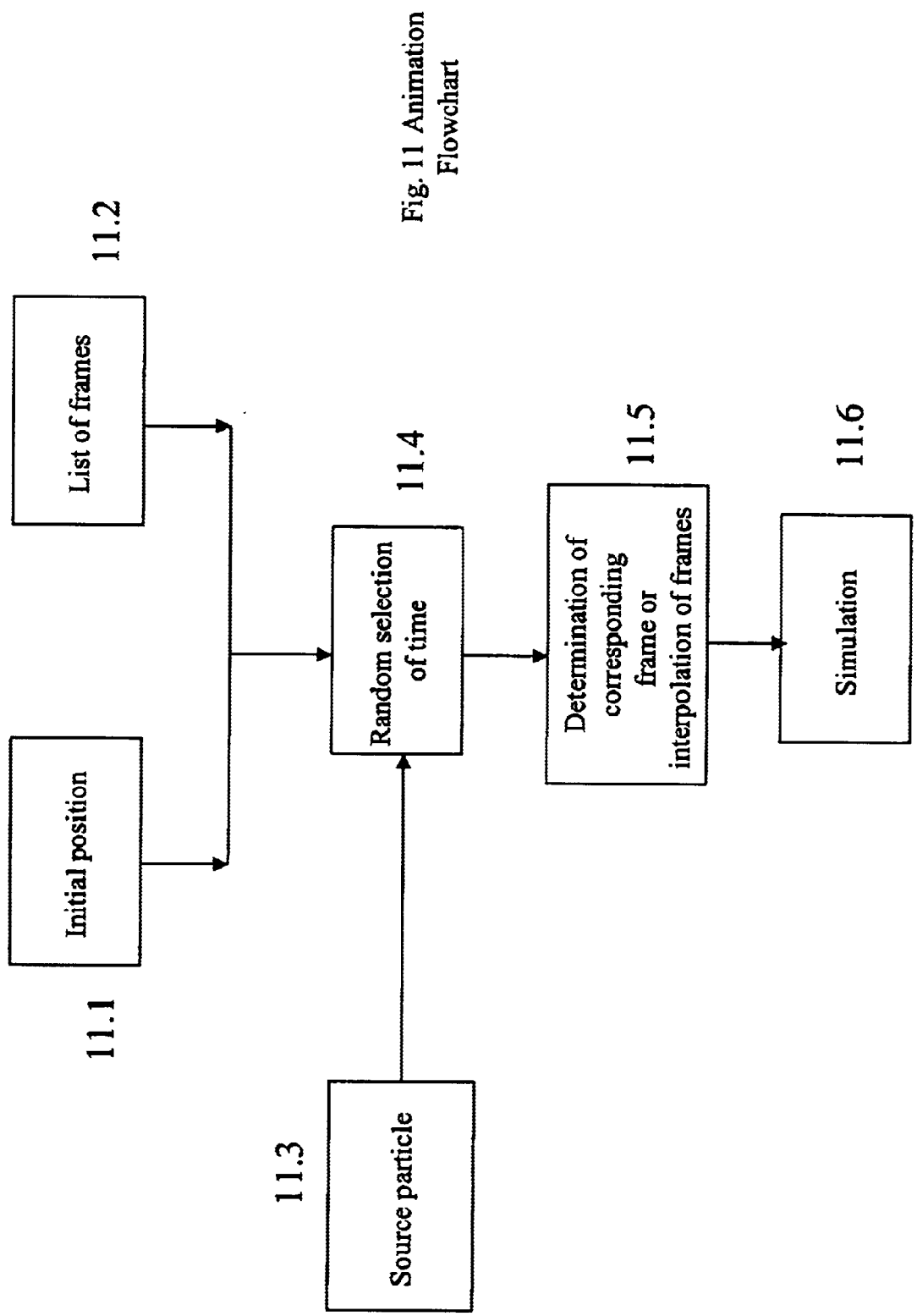
Fig. 11 Animation Flowchart

Beam Modifier Types
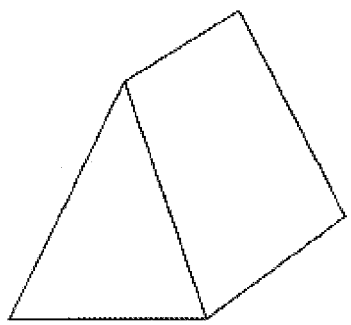
Fig. 12.1 Polyhedron
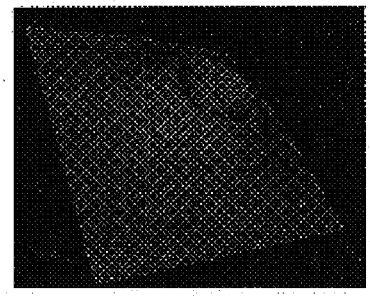
Fig. 12.2 Compensating filter
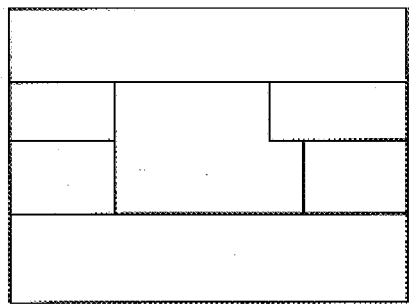
Fig. 12.3 MLC
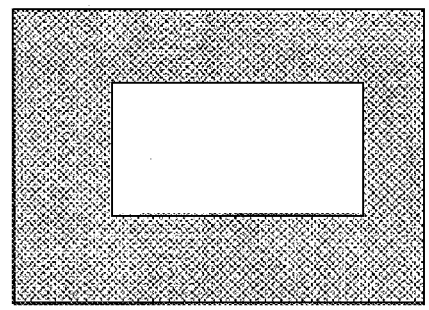
Fig. 12.4 Custom Port

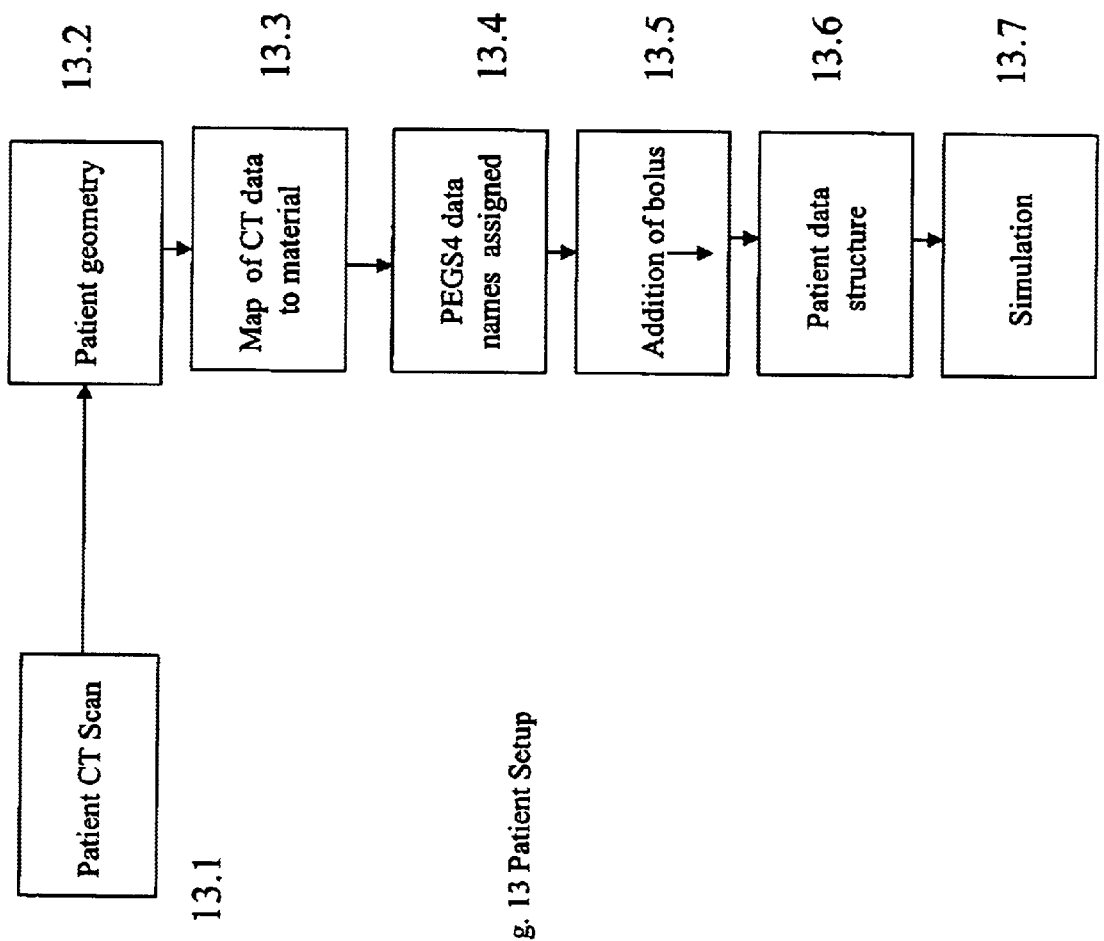
Fig. 13 Patient Setup

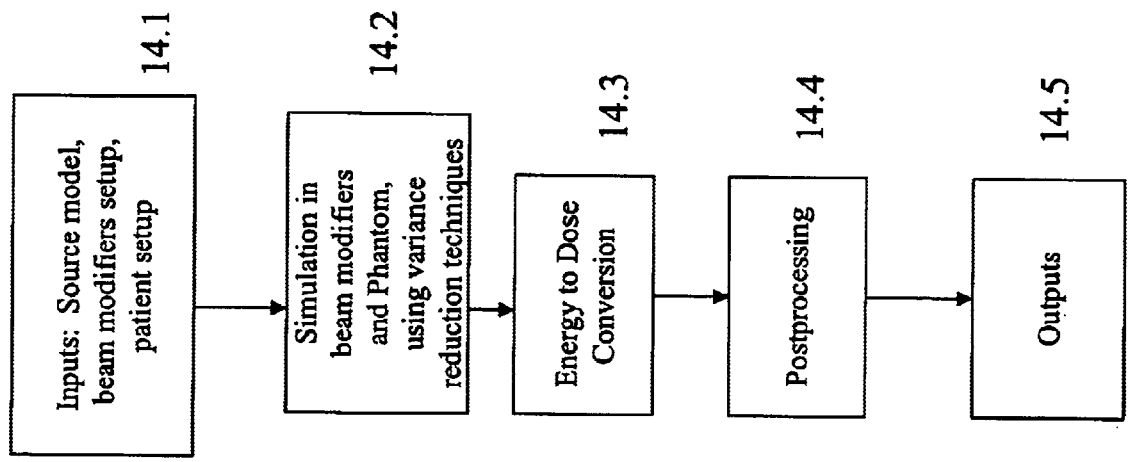
Fig. 14 NXEGS Simulation

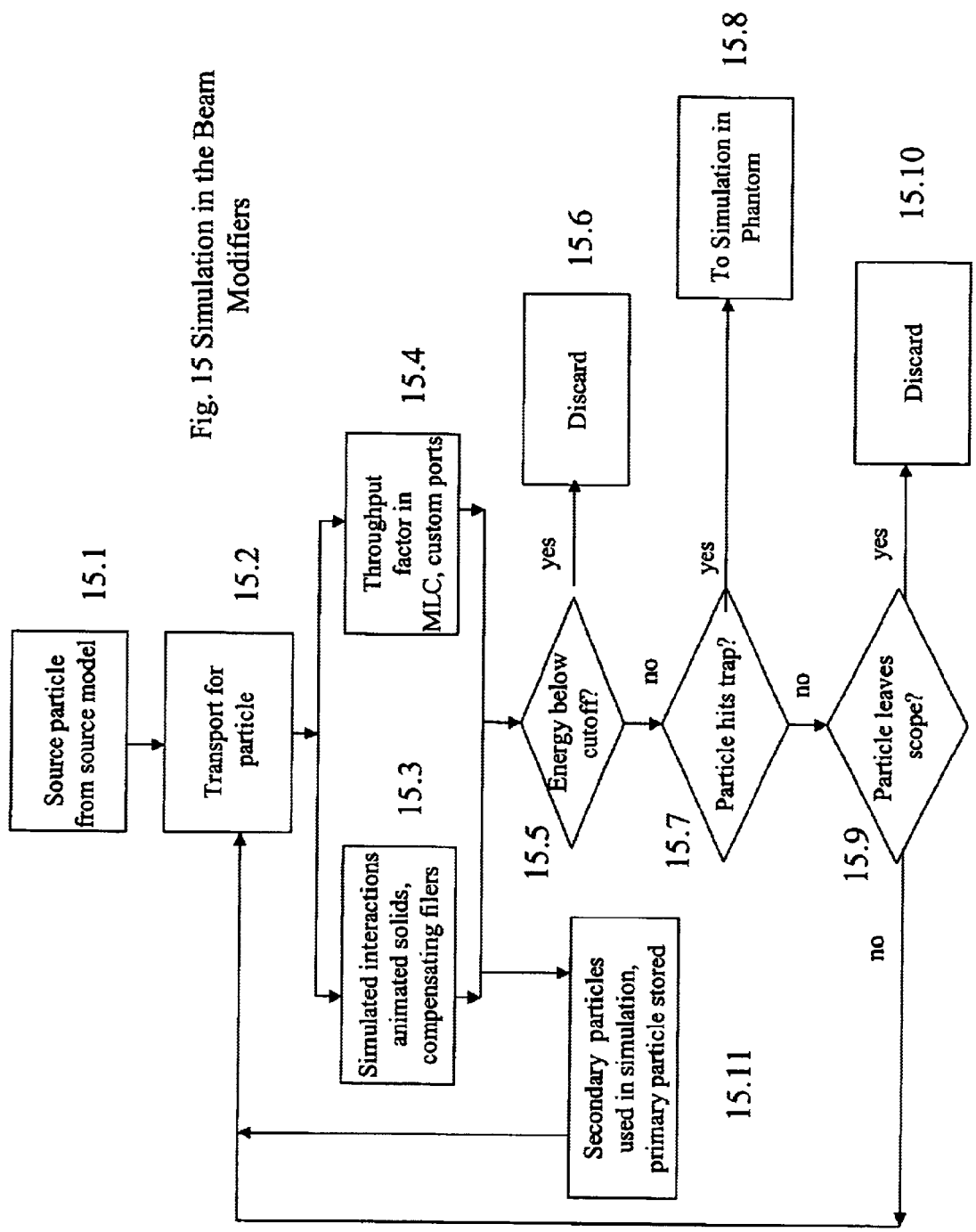
Fig. 15 Simulation in the Beam Modifiers

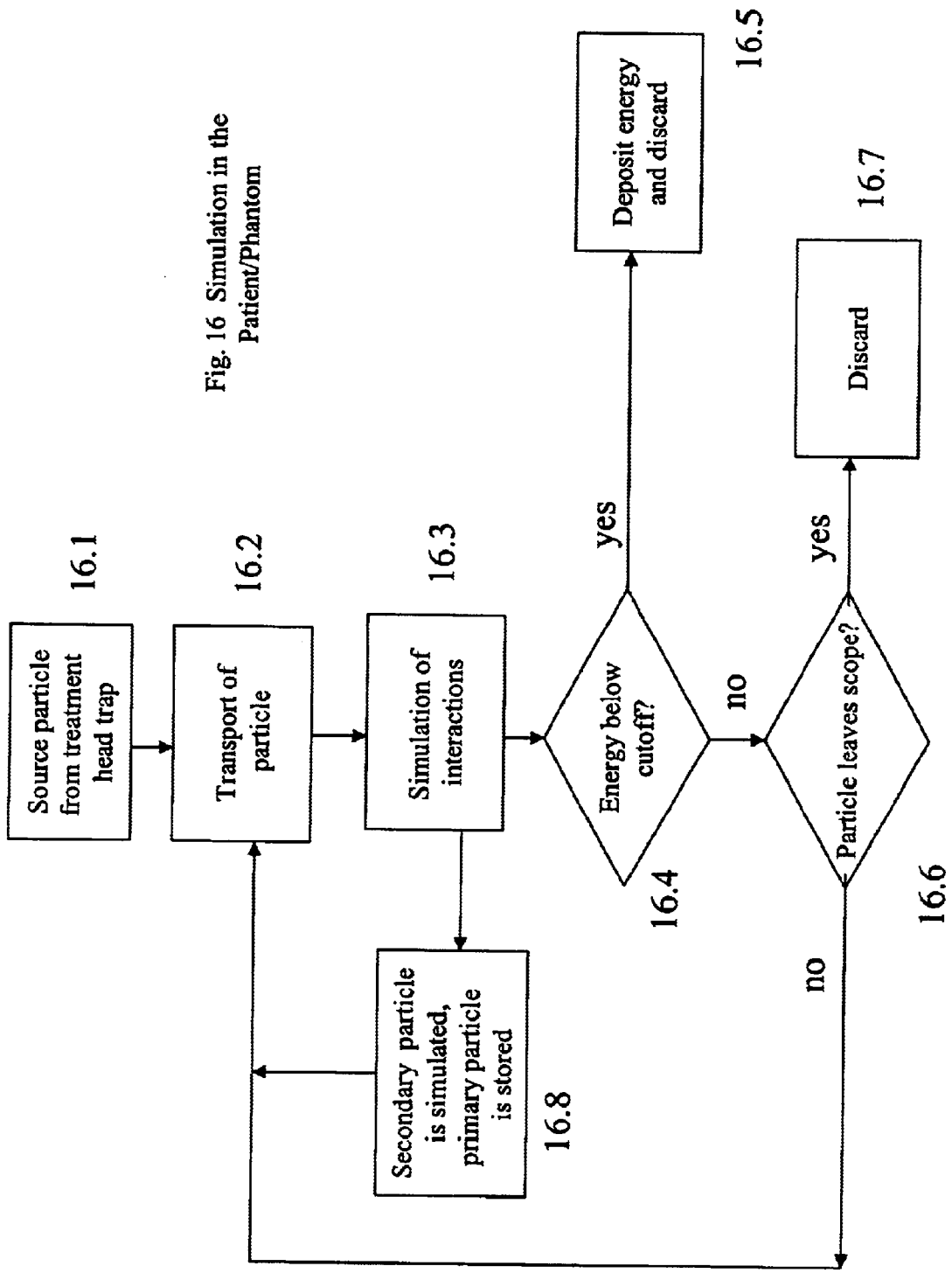
Fig. 16 Simulation in the Patient/Phantom

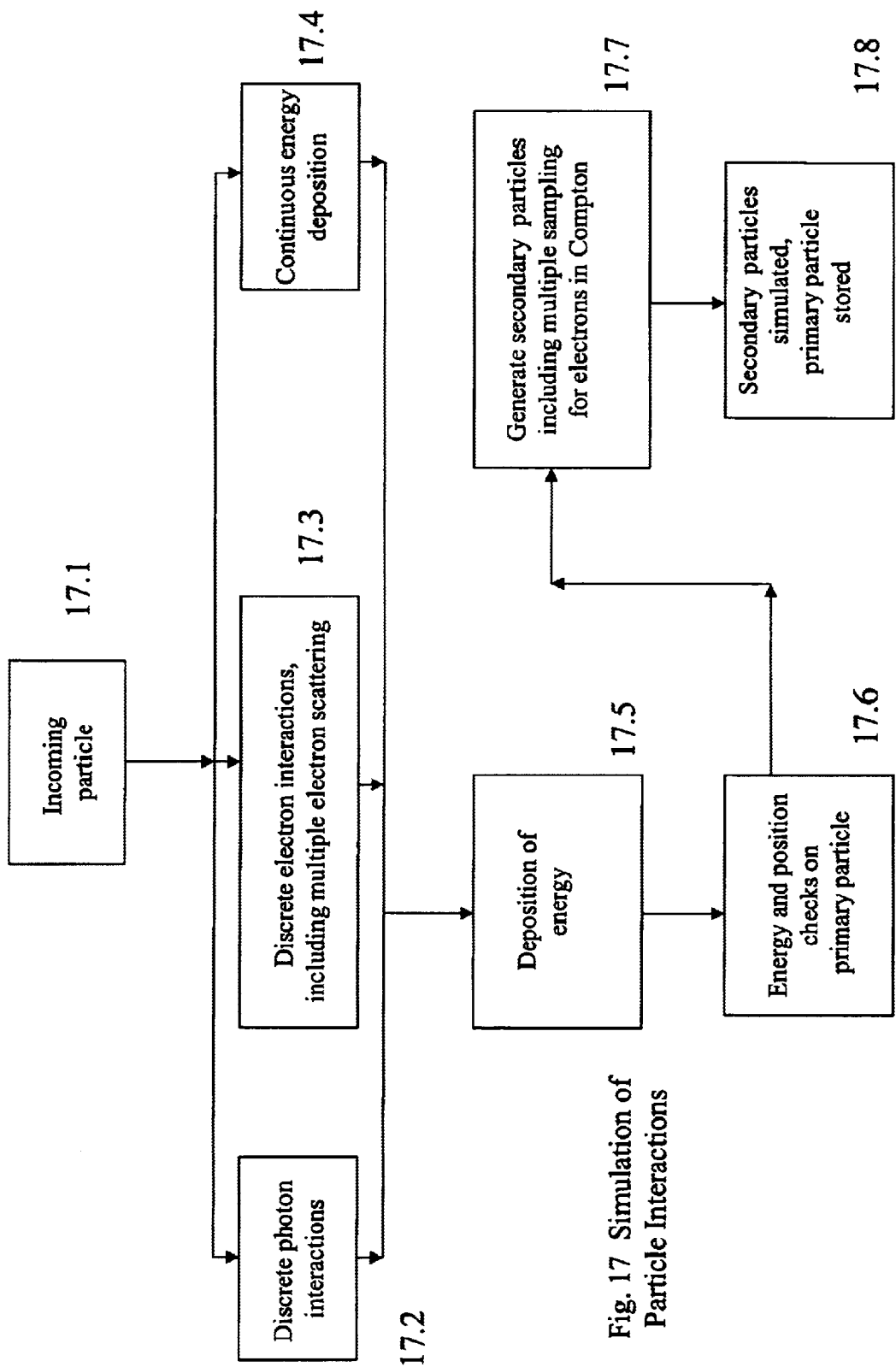
Fig. 17 Simulation of Particle Interactions

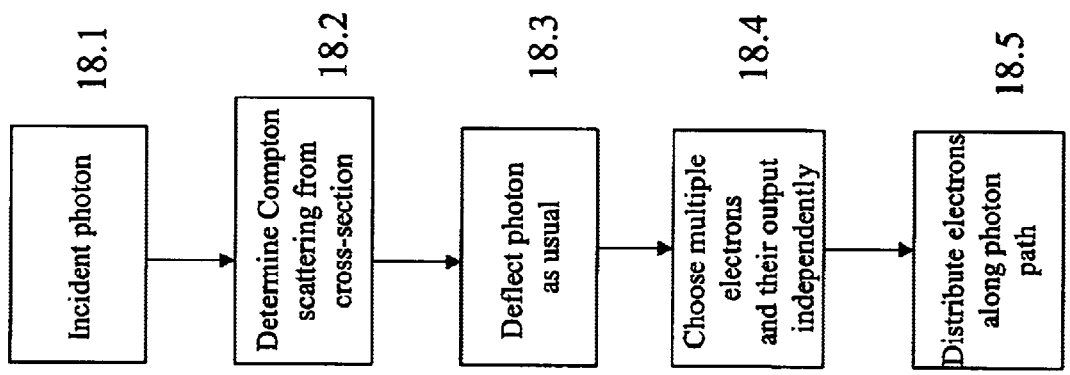
Fig. 18 Multiple Electron Sampling for Compton Scattering

Comparison of Coarse and Fine Grids
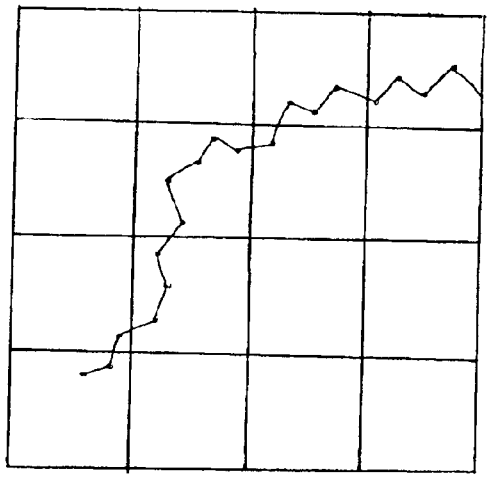
Fig 19.3 Simulation on fine grid
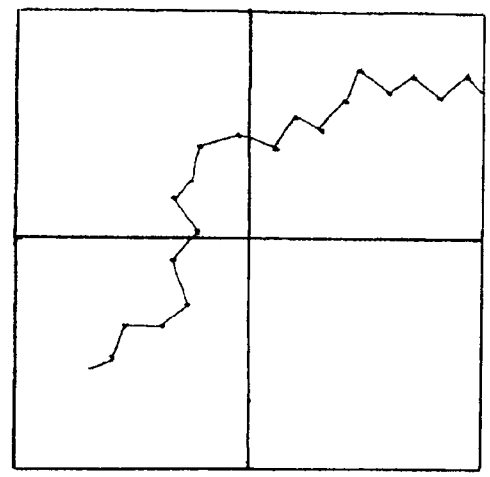
Fig 19.2 Simulation on coarse grid with short steps
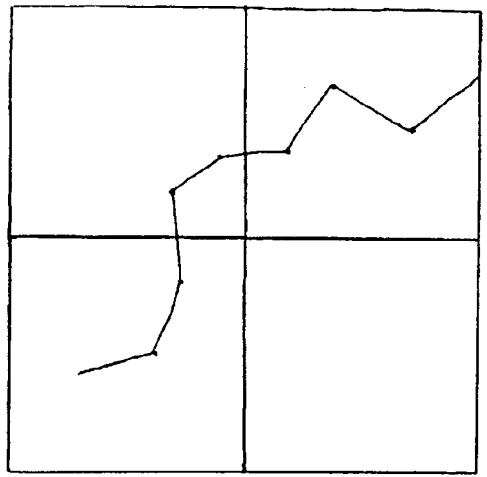
Fig 19.1 Simulation on coarse grid with long steps

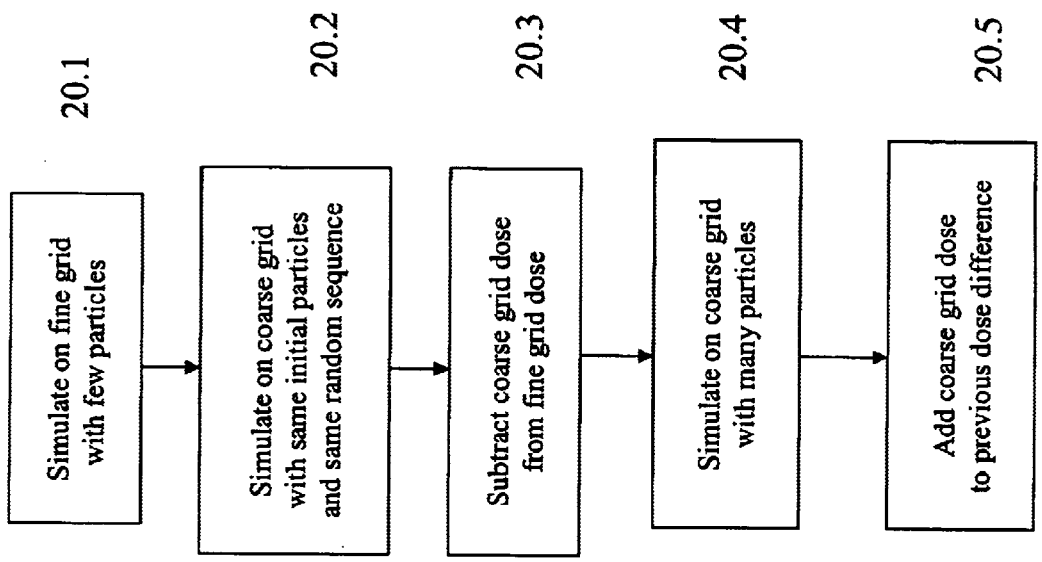
Fig. 20 Simulation on Coarse Grid as a Control Variate

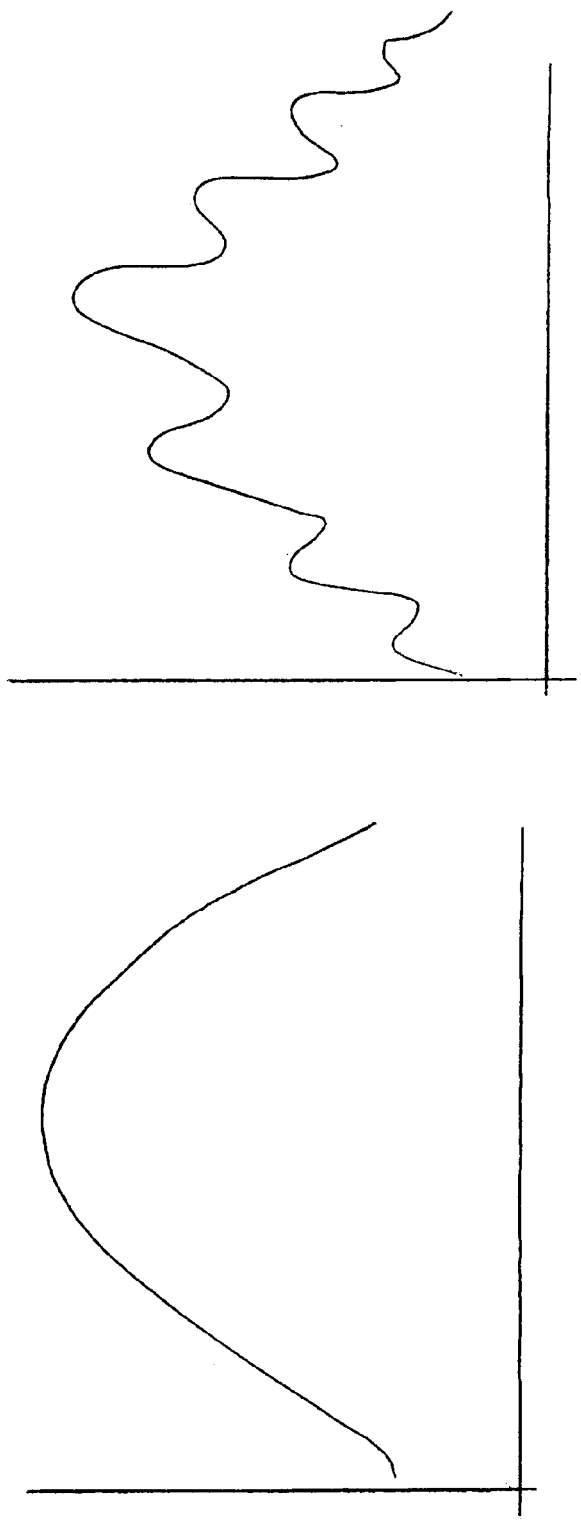

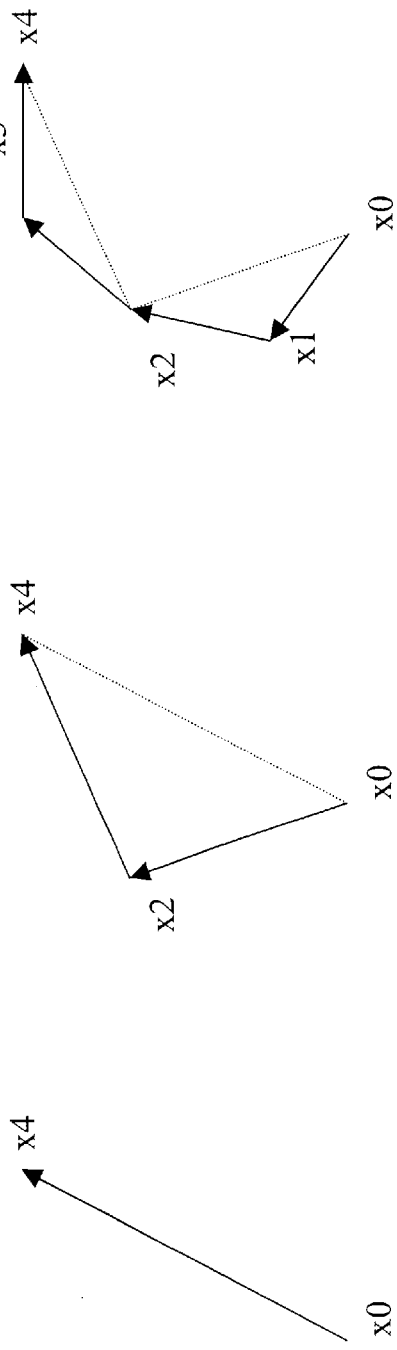

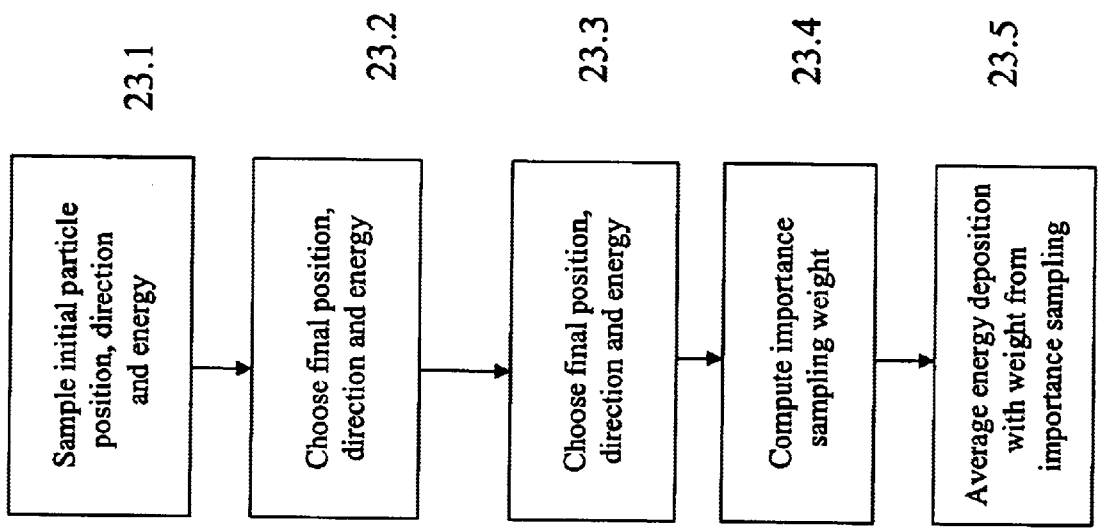
Fig. 23 Bidirectional Transport

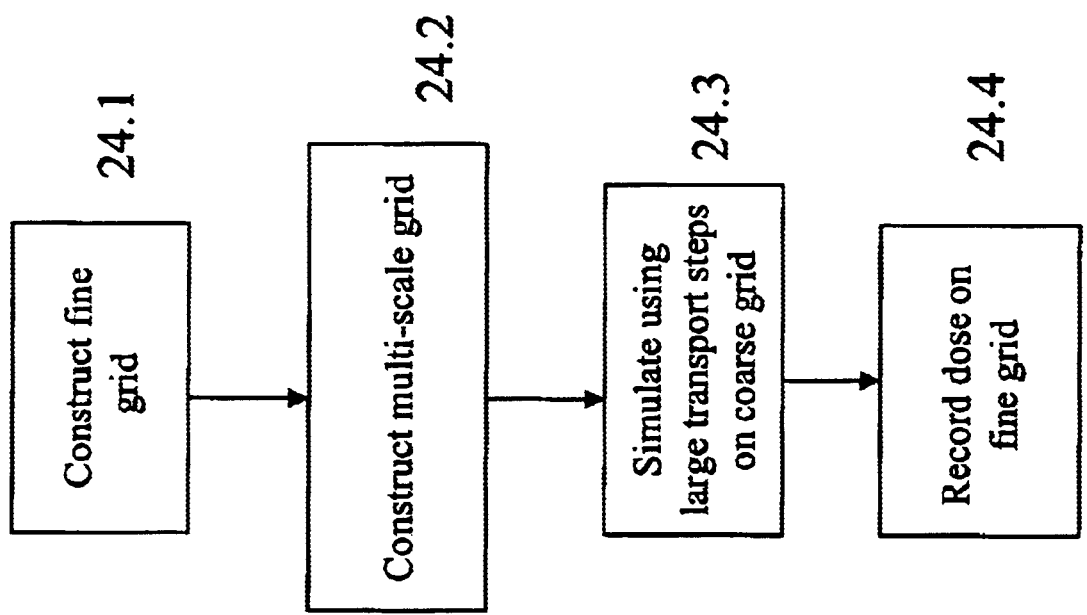
Fig. 24 Multiple Voxel Sizes

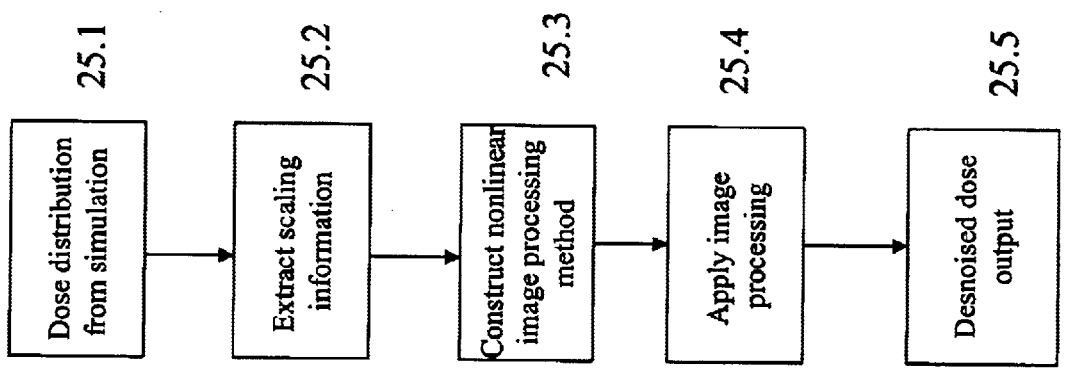
Fig. 25 Postprocessing

Comparison of Linear and Nonlinear Filter
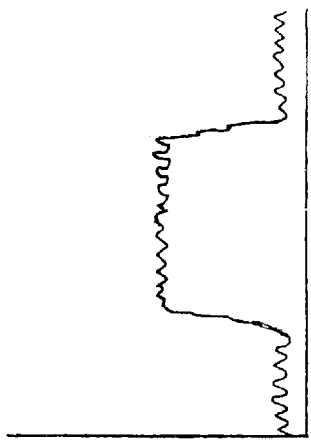
Fig. 26.1 Exact dose
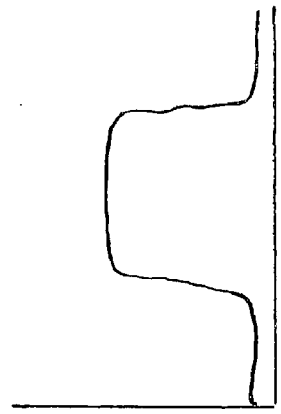
Fig. 26.2 Noisy dose
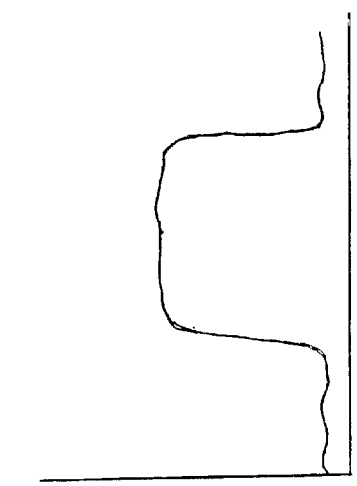
Fig. 26.3 Linear filter applied to noisy dose (arrows point to new oscillations)
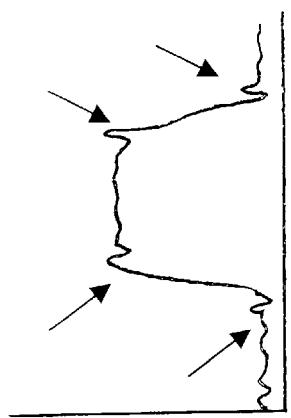
Fig. 26.4 Nonlinear filter applied to noisy dose

Comparison of Linear and Nonlinear Diffusion
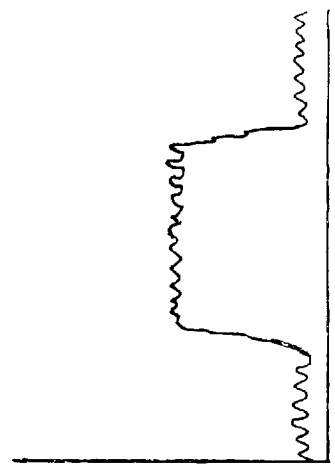
Fig. 27.1 Exact dose
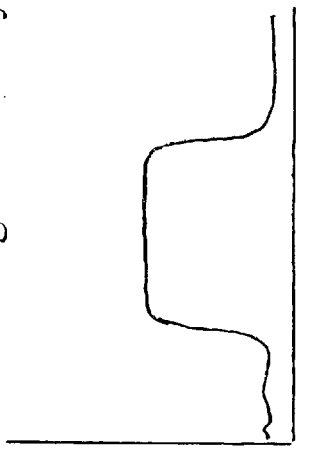
Fig. 27.2 Noisy dose
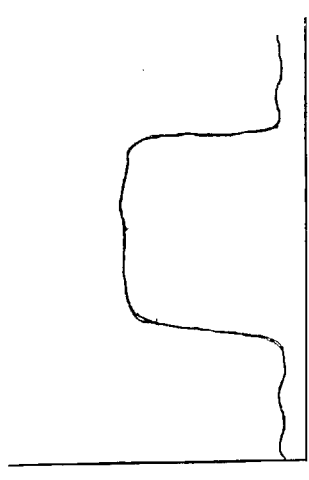
Fig. 27.3 Linear diffusion applied to noisy dose
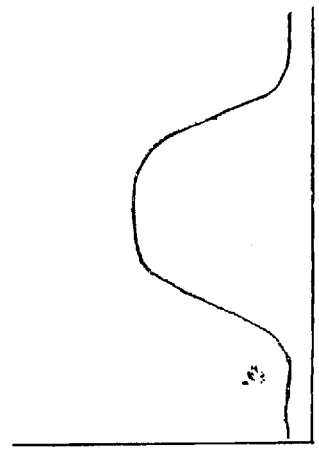
Fig. 27.4 Nonlinear diffusion applied to noisy dose

Fig. 28 Zombie Transport
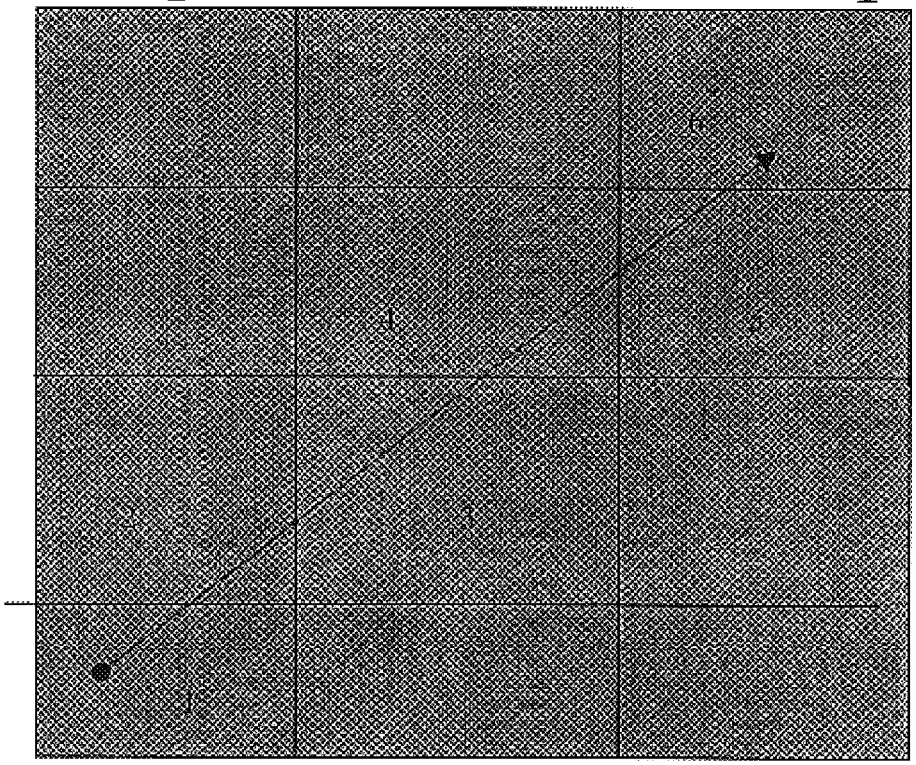
- Extended particle path starts from original dose deposition point
- EGS4 deposits energy only in zone 1
- Zombie transport deposits energy in zones labeled 1,2,3,4,5,6.

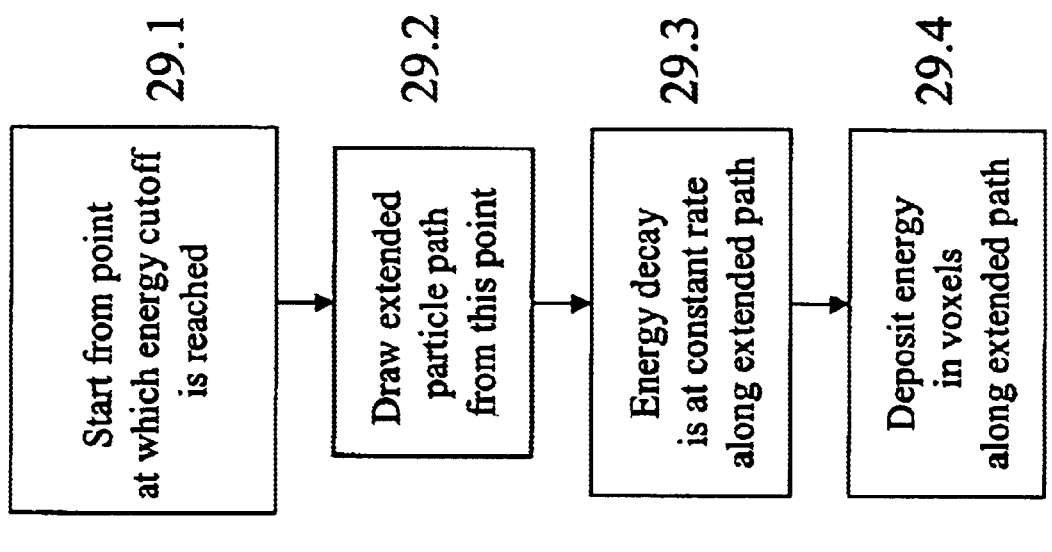
Fig. 29 Zombie Transport Algorithm

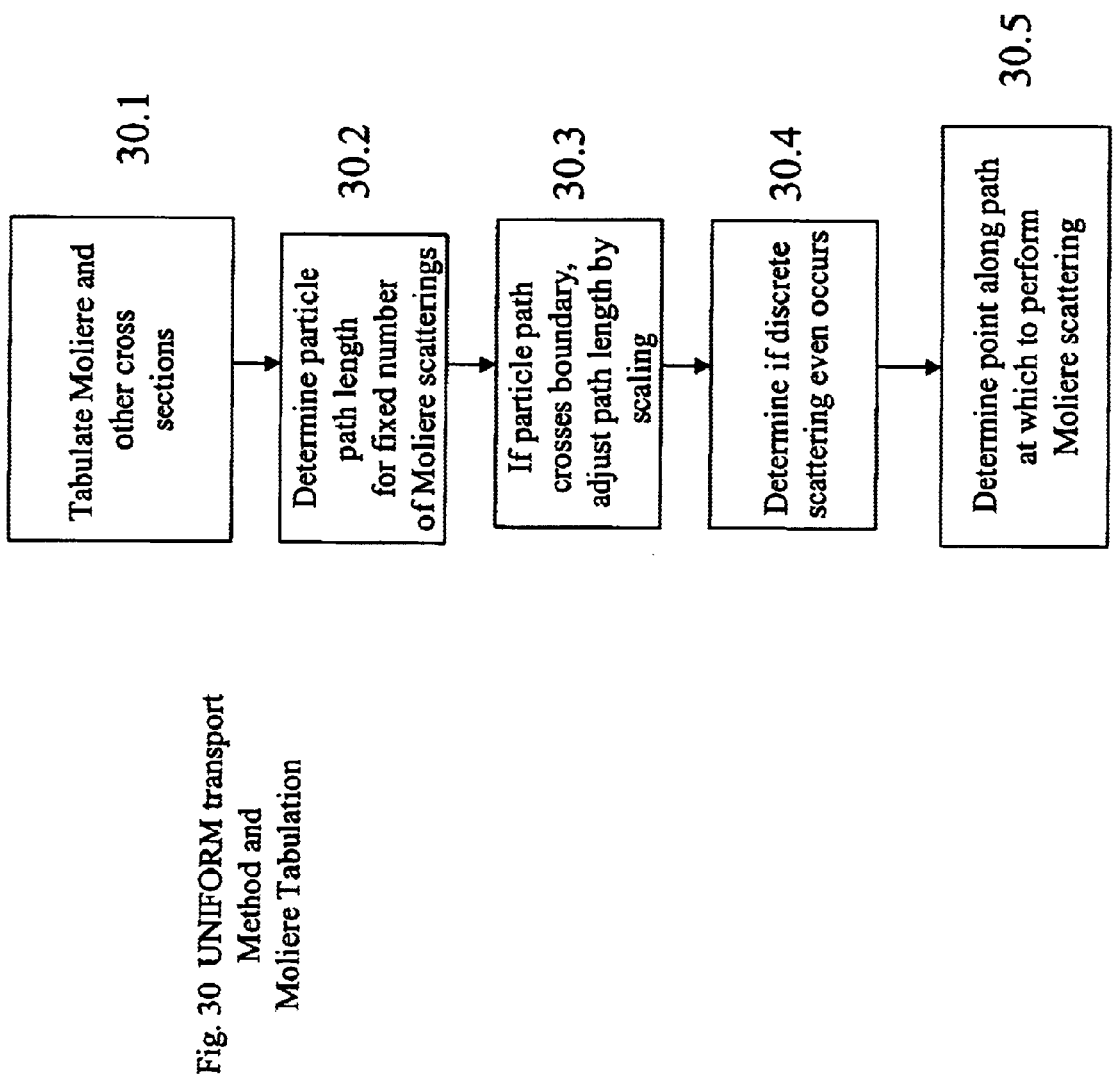
Fig. 30 UNIFORM transport Method and Moliere Tabulation

Scattering and Discrete Events for Moliere Tabulation

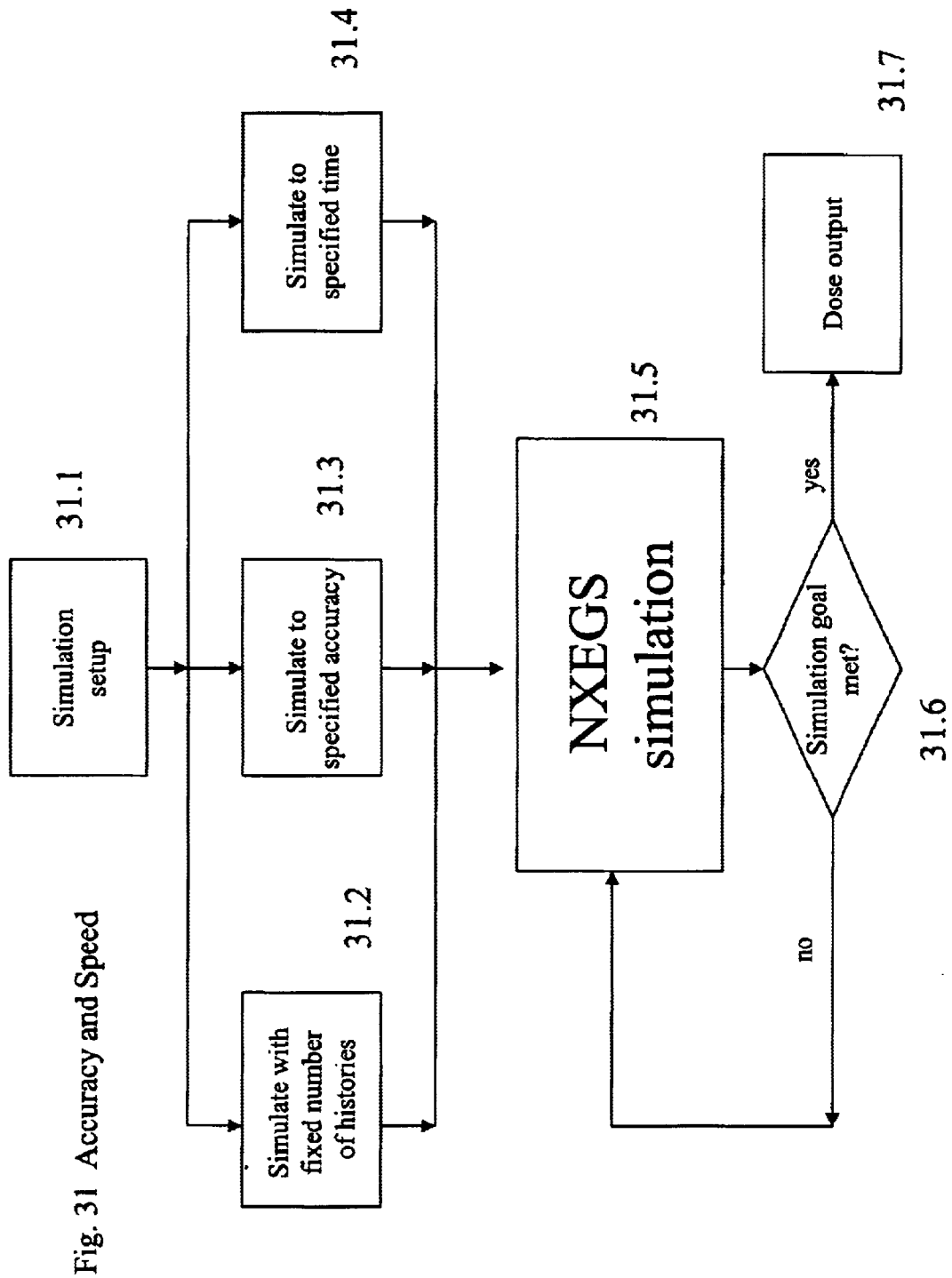
Fig. 31 Accuracy and Speed

RADIATION THERAPY TREATMENT METHOD

CROSS REFERENCE TO RELATED APPLICATION

The present application claims benefit of U.S. provisional application No. 60/234,538 filed Sep. 22, 2000 and U.S. provisional application Ser. No. 60/235,296 filed Sep. 26, 2001.

BACKGROUND OF THE INVENTION

1. Field of the Invention

This invention relates to radiation therapy. Embodiments of the invention are implemented as a software system, called NXEGS, that uses Monte Carlo simulation of radiation transport for radiotherapy treatment planning (RTP) and includes the following capabilities: commissioning of a linear accelerator to construct an equivalent source model, simulation of radiation transport through beam modifiers, and simulation of radiation transport in a patient or phantom to obtain the resulting dose distribution. Embodiments of the invention are implemented using a digital computer programmed to execute the NXEGS software and algorithms described herein.

2. Description of Related Art

The following background citations will be referred to by the references indicated in brackets. The entirety of all of these citations are incorporated herein by reference.

[1] W. R. Nelson and D. W. O. Rogers, "Structure and Operation of the EGS4 Code System" in *Monte Carlo Transport of Electrons and Photons*, T. M. Jenkins, W. R. Nelson and A. Rindi, eds., Plenum, 287–305, (1989).

[2] D. W. O. Rogers and A. F. Bielajew, "Code Accuracy" (Section III, pp. 492–522) in "Monte Carlo techniques of electron and photon transport for radiation dosimetry" in *The Dosimetry of Ionizing Radiation*, Vol. III, K. Kase, B. Bjangard and F. Attix, eds., Academic Press, 427–539, (1990).

[3] D. W. O. Rogers, B. A Faddegon, G. X. Ding, C. -M. Ma, J. We and T. R. Mackie, "BEAM: A Monte Carlo code to simulate radiotherapy treatment units" *Medical Physics* 22 (1995) 503–524.

[4] C. -M. Ma, B. A Faddegon, D. W. O. Rogers and T. R. Mackie, "Accurate characterization of Monte Carlo calculated electron beams for radiotherapy" *Medical Physics* 24 (1997) 401–416.

[5] J. J. DeMarco, T. D. Solberg and J. B. Smathers, "A CT-based Monte Carlo simulation tool for dosimetry planning and analysis" *Medical Physics* 25 (1998) 1–11.

[6] C. L. Hartmann Siantar, et al. "Lawrence Livermore National Laboratory's PEREGRINE Project" UCRL-JC-126732 and in 12th *International Conference on the Use of Computers in Radiation Therapy*. (1997).

[7] A. F. Bielajew and D. W. O. Rogers, "Variance-Reduction Techniques" in *Monte Carlo Transport of Electrons and Photons*, T. M. Jenkins, W. R. Nelson and A. Rindi, eds., Plenum, 407–419, 1989.

[8] D. L. Donoho "De-noising by soft-thresholding", *IEEE Transaction. Information Theory* 41 (1995) 613–627.

[9] L. Rudin and S. J. Osher "Total variation based image restoration with free local constraints" *Proceedings of 1st International Conference on Image Processing, Austin, Tex.*, IEEE Comput. Soc. Press, (1994), p.31–35.

[10] A. L. Ames, D. R. Nadeau and J. L. Moreland (1997) *VRML 2.0 Sourcebook* Wiley pp. 112–115.

[11] H. A. Bethe (1953) "Molière's theory of multiple scattering" Phys. Rev. 89, 1256–1266.

[12] W. H. Press, S. A. Teukolsky, W. T. Vetterling and B. P. Flannery. "Linear Regularization Methods" in *Numerical Recipes in C. The Art of Scientific Computing*. Cambridge Press (1992) pp. 309–315, 620–623, 808–815.

[13] "Evaluated Teletherapy Source Library" (2000) U.S. Pat. No. 6,029,079.

[14] "Calculation of Radiation Therapy Dose Using All Particle Monte Carlo Transport" (1999) U.S. Pat. No. 5,870,697.

[15] "Treatment Planning Method and Apparatus for Radiation Therapy" (1999) International Patent Application #WO99/40523

[16] J. O. Deasy. "Denoising of electron beam Monte Carlo dose distributions using digital filtering techniques" *Phys. Med. Biol.* 45 (2000) 1765–1779.

[17] I. Kawrakow and M. Fippel (2000) "Investigation of variance reduction techniques for Monte Carlo photon dose calculation using XVMC" *Phys. Med. Biol.* 45, 2163–2183.

[18] J. Sempau, S. J. Wilderman and A. F. Bielajew (2000) "DPM, a fast, accurate Monte Carlo code optimized for photon and electron radiotherapy treatment planning dose calculations" *Phys. Med. Biol.* 45, 2263–2291.

[19] T. Holmes and T. R. Mackie (1994) "A filtered back-projection dose calculation method for inverse treatment planning" *Med. Phys.* 21, 303–313.

[20] J. R. Cunningham (1972) "Scatter-air ratios" Phys. Med. Biol. 7, 42–51.

[21] T. R. Mackie, J. W. Scrimger and J. J. Battista (1985) "A convolution method of calculating dose for 15 MV x-rays" Med. Phys. 12, 188–196.

[22] M. Kalos and P. Whitlock (1986) *Monte Carlo Methods* Vol. 1. Wiley. pp. 92–103 and 107–109.

[23] E. Veach and L. J. Guibas (1995) "Optimally combining sampling techniques for Monte Carlo rendering" in *Computer Graphics Proceedings. SIGGRAPH* 95, R. Cook, ed., ACM, 1995. p.419–28.

[24] K. R. Hogstrom, M. D. Mills ad P. R. Almond (1981) "Electron beam dose calculations" Phys. Med. Biol. 26, 445.

[25] B. A. Faddegon and I. Blevis (2000) "Electron spectra derived from depth dose distributions" Med. Phys. 27, 514–526.

[26] A. F. Bielajew and D. W. O. Rogers (1987) "PRESTA: The Parameter Reduced Electron-Step Transport Algorithm for Electron Monte Carlo Transport" Nucl. Instr. Meth. Phys. Res. B18, 165–181.

About 1,400,000 people in the US are diagnosed with cancerous tumors each year. Every American has roughly a 50% chance of contracting some form of cancer during their lifetime, and the number of cases is anticipated to rise substantially in the years to come. Roughly 50% of those diagnosed are treated with radiation in the form of high energy electron beams or photon (X-ray) beams.

FIG. 1.1 shows a schematic drawing of the treatment setup. The radiation source is typically a linear accelerator (linac). After it is emitted from the linac, the radiation beam passes through a set of beam modifiers and then on to the patient or phantom. The treatment head, consisting of linac and beam modifiers, is contained in a moveable gantry, whose position and direction are variable. FIG. 1.2 shows more detail of the components within the treatment head. Following the linac, one finds four moveable jaws ("left" and "right", "up" and "down") that determine the width of the photon beam in the plane transverse to the central axis and one or more scrapers used to define the size of the electron beam. Then there are beam modifiers (such as the wedge and port shown in the FIG. 1.2) that are used to modify the intensity profile of the beam.

In order to make the treatment more effective, one must plan quantitatively the exposure to radiation in terms of dose amount, time duration and scheduling of treatments. This requires an accurate simulation of the way in which the radiation beams pass through the patient's tissue and interact with the tumor. Typically, multiple radiation beams are used on a patient, and their direction and intensity must be chosen carefully to apply adequate dose to the cancer without harming healthy tissues.

Intensity modulated radiation therapy (IMRT) and other new treatment modalities allow much more aggressive treatment therapies. These might prescribe a high dose to a target that is close to a critical tissue, so that relatively small errors in the dose calculation could be of great clinical significance. Monte Carlo simulation is the most accurate method for computation of radiation dose delivery, and so it is desired for radiotherapy treatment planning (RTP).

The Monte Carlo method for radiation therapy involves direct computational simulation of the physics of particle transport in the transport media (the beam modifiers and the patient). Particles interact with the transport media through atomistic processes, the outcomes of which are chosen randomly using scattering cross-sections. "Monte Carlo" refers to these random choices, which are made with the help of a computerized random number generator.

EGS4

The Monte Carlo computer code EGS4, developed at the Stanford Linear Accelerator (SLAC) and the National Research Council of Canada (NRCC) [1], simulates the radiation transport and deposition of dose within a general geometry, such as a patient or phantom. It has been carefully validated and shown to provide highly accurate dose distributions (e.g. see [2]).

The patient or phantom is divided into spatial cells, or voxels, using a rectangular or nonrectangular grid. A typical cell size is 5 mm in each direction. Within each cell the material properties of the patient are input from CT scan data.

Radiation transport in EGS4 includes three kinds of particles: photons (treated as particles as opposed to waves), electrons and positrons. Particles originate at a source and then travel through the phantom (or patient), interacting with the phantom (or patient) material. These interactions result in scattering of the primary particles and generation of new, secondary particles. Each interaction results in a change in the direction and energy of the scattered particle. The change in energy is due to energy imparted to the new particles and energy deposited in the material.

Each scattering process is described by a scattering cross section, which provides the probability or rate for scattering at a given angle. The relevant scattering processes in the Monte Carlo code, EGS4, are described below. As a particle undergoes scattering, the choice of angle and energy from the scattering cross section is a random choice, which is simulated using a computer generated random number (more correctly called a pseudo-random number).

For each source particle, the resulting trajectories of the primary and the resulting secondary particles is described in EGS4 as a shower. Each shower consists of a primary source particle (either a photon or electron) and all of the secondary particles (including particles generated from secondary particles) that are generated.

A photon moves through a material along a path consisting of straight line segments separated by discrete interactions. In EGS4, four interactions of photons with matter are included: pair production, Compton scattering, the photoelectric effect and Rayleigh scattering. In addition, new photons are produced by interactions of electrons and positrons with matter, including Bremstrahlung emission and annihilation.

The transport of electrons and positrons is more complicated than the transport of photons, because their interaction rate (i.e. cross-section) is much larger. EGS4 is a so-called "Class II" algorithm in which the energy loss and deflection of electrons is split into two components: discrete interactions and continuous energy loss. The continuous energy loss simulates the interactions that involve change of energy below an energy threshold. Interactions involving change of energy above this energy threshold are represented as discrete interactions. These latter include Bremstrahlung emission, Möller scattering, Bhabha scattering and annihilation, and elastic scattering. Along each segment of the path of an electron, the occurrence of one of these processes is determined by sampling from the appropriate cross-section. If a discrete interaction does occur, then the resulting deflection, energy loss and secondary particles are randomly chosen from appropriate cross-sections as well. Energy that is not transferred to the secondary particles is absorbed by the material. When a particle energy falls below a certain cutoff value (ecut and pcut, for electrons and photons respectively), the particle is discarded and all of its energy is deposited into the medium.

Of the electron interactions listed above, elastic scattering is treated differently from the others. It is represented by a multiple-scattering process, which groups many small elastic scatterings into a single multiple-scattering step, as described by Molière's theory [11]. This is applied at discrete increments along an electron path, with a change of angle in each increment. The transport step is modified to allow for larger steps and for steps that cross a material boundary using the PRESTA method [26]. Since each multiple-scattering interaction corresponds to many elastic scatterings, the energy deposition from multi-scattering is applied continuously along the electron path, according to the "Continuous Slowing Down Approximation" (CSDA). This is distinct from the continuous energy deposition used to represent interactions involving small energy change, as described in the previous paragraph.

Once the simulation has finished, then the accumulated energy deposition in each cell of the patient geometry is converted into a dose, which is the ratio of the deposited energy in the cell divided by the total mass in the cell. The resulting dose values have units of energy deposition per mass. The commonly used unit of dose is the gray (denoted Gy), which equals one Joule per kilogram, or the rad (also called a centi-gray or cGy) which is equal to one one-hundreth of a gray.

Accuracy of the computed dose distribution and time required for the computation are two crucial issues for any Monte Carlo method. In general terms, the accuracy level $\epsilon$ and the computational time $T_{comp}$ are given by $$\epsilon = c_1 N^{-1/2}$$
$$T_{comp} = c_2 N = c_2 c_1^2 \epsilon^{-2} \tag{1}$$

in which N is the number of particles, the constant $c_1$ is a measure of (the square root of) the variance and the constant $c_2$ is a measure of the computational time per history. This shows that the accuracy level and the computational time are closely related.

EGS4 includes a number of variance reduction methods that reduce the error $\epsilon$ for a given number N of particles by reducing the variance $c_1^2$ [7]. A variance reduction method consists of a change in the transport algorithm that reduces the statistical error (i.e. the variance) in the dose distribution in a way that is unbiased, i.e. that does not change the average value of dose in each voxel. For a prescribed level of accuracy $\epsilon$, variance reduction has the effect of lowering the computational time $T_{comp}$. Conversely, a variance reduction method allows a better (i.e. smaller) accuracy level $\epsilon$, for the same computational time $T_{comp}$.

Some of these variance reduction methods work by splitting particles into multiple representative particles at certain points in the transport simulation. The increase in the number of particles is balanced by assignment of a weight to each of the particles. The reason for employing particle splitting and weights is to optimize the use of the particles. For simple interactions (i.e. cross sections with little variation), relatively few particles are needed to get an accurate sample of the effect of the interaction. For complex interactions (i.e. cross sections with a lot of variation) many particles are needed to adequately sample the interaction. So the simulation is performed most efficiently if few particles are used for the simple interactions, but the few particles are split into many when a complicated interaction occurs.

In spite of its accuracy, EGS4 has not been widely implemented in clinical applications, because it may take as long as 20 or more hours for a single dose computation on a modern workstation, even with use of the variance reduction methods in [7]. In a typical cancer center, however, the dosimetrist who is responsible for creating the treatment plan can only spend about an hour or so with each patient, and creation of the treatment plan requires at least several dose computations. Embodiments of the present invention, NXEGS, remove this obstacle by acceleration of the Monte Carlo code to clinically acceptable speeds.

In addition to simulation of particle transport and dose deposition within a patient or phantom, the radiotherapy treatment planning also requires determination of the radiation emitted from the linear accelerator and its modification by the beam modifiers. The beam modifiers, shown in FIG. 1.2, are adjacent to the linear accelerator's exit plane (located at the exit of the linac) and modify the radiation beam emitted from the linear accelerator.

BEAM

The program BEAM, developed at NRCC [3], is an EGS4 user's code for simulation of linac output and its modification by the beam modifiers. It uses methods similar to those in EGS4, and for a number of linear accelerators, BEAM has been shown to reproduce the beam output quite faithfully (e.g. see [4]). On the other hand, BEAM requires complete and accurate knowledge of the components of the linear accelerator (e.g. geometry and constitutive materials), which is not readily available from the manufacturer. In contrast, embodiments of the present invention, NXEGS, includes a beam commissioning tool that uses dosimetry calibration data, rather than manufacturer specifications, to construct a source model that faithfully represents the output of the linac.

BEAM also simulates the radiation transport through the beam modifiers. The current implementation is incomplete, however, in that it does not include dynamic treatment modifiers, such as dynamic wedges and multi-leaf collimators (MLC), and it does not include compensating filters. In addition, simulation through the beam modifiers in BEAM is not directly connected to a simulation method for the patient and phantom. Also, BEAM may take many hours to simulate transport through a set of realistic beam modifiers. Embodiments of the present invention, as implemented in the computer code NXEGS, include the full range of available beam modifiers, including dynamic wedges, MLC and compensating filters. Moreover, NXEGS is directly connected to transport simulation and dose computation in the patient/phantom, and it performs computations of transport through the beam modifiers in a clinically acceptable time.

Other Programs

Other related methods include MCNP and Peregrine. Similar to EGS4, MCNP is a general method for Monte Carlo simulation of particle transport. It has been applied to radiation therapy, e.g. [5], with results that are similar to those of EGS4, but its use is not as widespread as that of EGS4.

Peregrine refers to a project at the Lawrence Livermore National Laboratory (LLNL) on Monte Carlo simulation for radiotherapy [6]. It includes a wider range of particle types [14] than EGS4, and uses updated collision cross sections. Its beam commissioning approach [13] is similar to that of BEAM, in that it performs direct simulation of the linac and requires full specification of the internal components of a linac. Peregrine applies parallel computation to accelerate the simulation of particle transport in the beam modifiers and patient.

Several other techniques have been developed for acceleration of Monte Carlo simulations for particle transport. These methods reduce the statistical error (variance) in the dose distribution produced from simulation of N source particles in the radiation beam. This reduces the value of N that is required to meet a given accuracy goal, and so it accelerates the computation.

The Voxel Monte Carlo (VMC) method of [17] and the Dose Planning Method (DPM) of [18] completely change the basic particle transport method in EGS4 in order to accelerate the computation. The VMC method uses precomputed transport steps to increase the size of the steps. The DPM method reorders the combination of particle motion and particle interactions.

Linear digital filtering techniques have been proposed in [15] and implemented in [16] for reducing the statistical error in the dose distribution after completion of the transport simulation. These filtering techniques remove any high wavenumber components in the dose distribution. Earlier application of filtering to inverse dose calculation for radiation therapy appeared in [19].

The new acceleration methods of embodiments of the present invention are distinct from these earlier methods. Embodiments of the present invention use new variance reduction methods and a new nonlinear image processing method, which are unrelated to the parallel computing, modified transport and linear filtering methods described above.

SUMMARY OF THE INVENTION

An embodiment of the invention is implemented as two software tools: a beam commissioning tool and a Monte Carlo dose calculation tool collectively referred to as NXEGS.

Beam commissioning is the process of obtaining a radiation source model to represent a specific linear accelerator in the clinic. The radiation source model is then used as input for the Monte Carlo dose calculation tool.

Linear accelerators can be run as either electron beams or photon beams; the calibration is performed separately for these two modalities. The energy (MeV) of the beam must also be specified.

For each beam type (electron or photon; both treated as particles) a large data set is obtained by measurement of dose deposition in a target (the "phantom") consisting usually of water. The required data set consists of scanning data and non-scanning data for a plurality of values of beam energy and beam width. Scanning data consists of dose values along the central axis of the beam or along a line in a cross section of the beam. Non-scanning data consists of dose values at specified points on the central axis of the radiation beam. Each of these is performed for beams of various widths and energies. Dose deposition values are typically measured in the phantom with a small ion chamber. This data collection requirement is similar to that required for existing commercial RTP systems, which are non-Monte Carlo implementations, such as FOCUS, sold by Computerized Medical Systems, St. Louis, Mo.

From the measured data, the commissioning process produces a source model that accurately represents the output of the actual linac. The source usually represent the phase space in terms of particles originating from several independent subsources; e.g. a focal point source at the beam center, extra-focal sources, and contamination sources. The radiation beam from the linear accelerator is simulated in the Monte Carlo transport computation by sampling particles from the subsources. For each such particle, the initial position, direction and energy of the particle is chosen at random by sampling from the subsources, which can be described as a phase space distribution (PSD) for the particles. The PSD consists of the probabilities for each combination of values of the initial positions, direction and energy for emitted particles. The initial position may be specified as a point on a sampling plane. For example, it may be taken to be at a source point within the linear accelerator, at a point on the exit plane of the linear accelerator, or in a plane at the top of the scrapers. This PSD can be sampled to obtain an arbitrary number of distinct particles which can then be used in an RTP simulation.

The first step in the dose calculation is to setup the geometry and material properties of the phantom or patient and beam modifiers. The patient geometry includes both the patient and any bolus (a treatment aid placed on the patient to minimize the effects of body curvature). A geometric grid is setup with a prescribed spacing (e.g., 5 mm). The outer boundary of the grid is its "scope." Once a particle leaves scope, it is no longer followed. Material properties of the patient are input as CT scan values, which are converted into material identification. The properties (e.g., interaction cross sections) of the identified material are, in turn, described through the PEGS4 (Preprocessor for EGS4) data set [1]. The PEGS4 data set consists of cross-section data that describes the statistics of the outcome for each of the interactions included in the EGS4 simulation method, for each energy of the incident particles, for each of the materials found in radiotherapy, and for each density of those materials.

The beam modifiers are used to shape the intensity profile of the radiation beam that is emitted from the linac. These include wedges, cutouts, ports, blocks, multi-leaf collimators (MLC) and compensating filters. For a given source model, particles are emitted from the linac exit plane or some other sampling plane, then transported through the beam modifiers. Transport through MLCs and custom ports is handled through modeling; transport through the other beam modifiers is simulated by Monte Carlo. Exiting particles from the beam modifiers are collected on a "trap" from which they are then emitted into the patient geometry. The geometry of the phantom and that of the beam modifiers have different centers and coordinate axes.

The basic transport simulation and dose deposition algorithm in NXEGS is the same as that of EGS4. However, NXEGS includes a new implementation of the EGS4 algorithms as a C++, object-oriented software system and with new features and improvements described herein.

Acceleration of the RTP simulation to clinically acceptable speeds is achieved in NXEGS through new transport methods, variance reduction and postprocessing methods. These methods reduce the statistical noise for a fixed number of source particles; equivalently they reduce the number of particles required for a prescribed accuracy level. Since computational time remains roughly proportional to the number of particles, this speeds up the computational time.

Variance reduction methods change the transport algorithm in order to reduce the generation of statistical noise. EGS4 employs a number of variance reduction techniques, including range rejection, interaction forcing, particle splitting and Russian roulette [7]. NXEGS uses a new particle splitting technique for the electrons affected in Compton scattering. One more useful addition is the distributed deposition from the "dead" electrons (those electrons whose energy falls below the cutoff), which we refer to as "zombie" transport.

Postprocessing in NXEGS is applied after the transport simulation is completed to reduce the statistical noise in the resulting dose distribution, without changing the algorithm for particle transport. This postprocessing is a form of image processing, in which the dose distribution values define the image. It is a new method for Monte Carlo acceleration. It is nonlinear, in that it first extracts information on the statistical error; then uses that information to eliminate some of this error from the distribution.

In summary, NXEGS provides a complete solution to beam commissioning and dose computation for RTP applications. Using standard dosimetry data, it produces a source model to match the radiation output from a given linac. For the beam modifiers, NXEGS handles the full range of beam modifiers, including dynamic beam modifiers, MLC and compensating filters. While the basic transport and dose deposition method is effectively identical to that of EGS4, novel acceleration methods in NXEGS greatly speedup the Monte Carlo simulation to achieve clinically acceptable computation times with high accuracy in the dose distribution.

Embodiments of the invention include a method of commissioning a radiation source which inputs measured dose data into a data processor. The measured dose data is derived from exposing a phantom to radiation from the source; and measuring the radiation dose to obtain a measured dose in the phantom resulting from the exposing step. The measured dose is measured at a plurality of points within the phantom. At least some of these points are axial points located at positions along a substantially central axis of the radiation source and others of these points are transverse points located at positions along an axis transverse to the central axis. After inputting he measured dose data, one performs a Monte Carlo simulation of the radiation source to determine a simulated dose at the plurality of points; and then models the radiation source using the simulated dose and the measured dose.

The dose data is obtained from positioning a phantom to receive radiation from the source, exposing the phantom to radiation from the source, and measuring the radiation dose in the phantom resulting from the exposing step. The number of dose measurement points may be 10 or greater and is preferably 50 and most preferably is a large number of dose measurements on the order of 100 points. The above described method has direct application to for use in radiation therapy planning.

According to other embodiments of the invention, there is described a method of modeling a radiation source which emits radiation in the form of particles. One step of the method includes defining at least one simulated sub-source comprising one of a focal source and an extra focal source; each simulated sub-source having a relatively small interval of energy values and a relatively small interval of angular values. Further, one performs a Monte Carlo simulation of particles leaving the at least one simulated sub-source to determine a simulated dose distribution; and then determines a phase space distribution of radiation leaving the at least one simulated sub-source using said simulated dose distribution and actual dose measurements.

According to other embodiments of the invention, there is described a method of performing radiation planning therapy in which one performs a CT scan of a patient to provide patient-dependent information in a region of the patient to be treated; utilizes a source model based on dosimetry data which includes at least 10 dosimetry points, and typically about 100 points, provides treatment head information concerning the characteristics and geometry of a treatment head; and simulates a dose distribution using a Monte Carlo calculation based on a source model, the patient-dependent information and the treatment head information.

Embodiments of the invention are characterized by a method of defining a source model of an accelerator emitting radiation. This method measures the actual radiation dose distribution from the accelerator over a spatial volume defined within a phantom and for a plurality of accelerator energies; uses a Monte Carlo simulation to calculate a transport matrix which relates the actual radiation dose distribution to a source phase space distribution, where the source phase space distribution is defined as the probability distribution of the position, energy and direction of radiation from the accelerator. Finally, the method calculates the phase space distribution using the transport matrix and the actual radiation dose distribution.

Yet other embodiments of the invention use a method of simulating radiation transport through a treatment head of a linear accelerator in which the treatment head has at least one beam modifier. The method employs inputting into a data processor, parameters corresponding to a physical description of the treatment head and the at least one beam modifier included in the treatment head; simulating the introduction of particles from a source into the treatment head; and performing simulated transport of particles through the at least one beam modifier in the treatment head through at least one of a Monte Carlo method or a throughput function.

There is further described according to other embodiments of the invention, a method of radiation treatment planning which includes performing one of (1) commissioning a linear accelerator to obtain a source model or (2) using a source model from a linear accelerator that has already been commissioned, wherein the commissioning includes utilizing at least 10 dosimetry points; simulating one or more beams based on a source model; specifying a simulated treatment head, including (1) geometry and (2) material properties of at least one beam modifier for each beam; setting up a simulated patient or a simulated phantom; simulating particle transport through the simulated treatment head using at least one of a Monte Carlo method or a throughput function for each beam; simulating particle transport through the simulated patient or simulated phantom using the Monte Carlo method; calculating a radiation dose in the simulated patient or simulated phantom; and providing an output of the calculated dose. In addition to specifying a simulated treatment head, including (1) geometry and (2) material properties, one may also specify motion of the at least one beam modifier.

Embodiments of the invention are further described as a method of specifying at least one beam modifier for use in Monte Carlo simulation of a particle motion through a treatment head which includes a radiation source and at least one beam modifier in which the method includes inputting into a data processor a geometry specifying said at least one beam modifier by performing at least one of the following three steps: (i) for a beam modifier in the shape of a polyhedron, inputting the coordinates of each vertex of the polyhedron and specifying the edges of connecting vertices, and inputting the position and orientation of the polyhedron; (ii) for a beam modifier in the form of a multi-leaf collimator, inputting the number and size of each leaf; and (iii) for a beam modifier in the shape of a compensating filter, consisting of a flat side and a curved shape of arbitrary complexity opposite the flat side, inputting the height of the curved shape above each point of the flat side, and specifying whether the flat side points toward or away from the radiation source. Finally, the method includes inputting a type and density of material that constitutes the at least one beam modifier.

The above method may include movement of the at least one beam modifier. In such a case, one further specifies movement of the at least one beam modifier by inputting a series of frames defined by specifying at least one of (1) positions and (2) orientations of the at least one beam modifier and a particle weight corresponding to each of the at least one of the frames; randomly selecting a frame for each of a plurality of simulated particles emitted from the radiation source; and applying the corresponding particle weight to each of the plurality of simulated emitted particle for use in the Monte Carlo simulation. In this manner, utilizing the particle weight simulates a time interval for each of the frames, and thus simulates the change of the at least one of the position and orientation of the at least one beam modifier so as to simulate moving the at least one beam modifier during the Monte Carlo simulation.

According to other embodiments of the invention, there is described a method for computing the dose deposition due to particles whose energy is below a cutoff, as part of a Monte Carlo simulation. The method comprising the steps of determining that a given particle has reached a cutoff energy within a given voxel; and for particles below the cutoff energy, performing the steps of: extending the particle path in a straight path from the point at which the cutoff was reached in the direction of the particle motion at said point; and simulating a constant energy deposition rate using a rate constant along the straight path .

Other embodiments of the invention are directed toward a method of simulating the transport of electrons using a Monte Carlo calculation. For a given energy of a simulated particle, one determines a step size in the Monte Carlo calculation to correspond to a fixed number of elastic scatterings wherein said step size is between an initial and end position and the particle path is a straight path between said initial and end positions. One further determines whether a discrete event occurs along said particle path based on the cross section of the particle within the material through which the particle path traverses. If a discrete event does not occur along the particle path, then the method utilizes the steps of: randomly selecting a first intermediate point between the initial position and the end position along said particle path; determining a scattering angle at the first intermediate point based on a tabulated cross section of the material existing at the first intermediate point; and simulating a Molière scattering event at the first intermediate point with the determined scattering angle wherein the Molière scattering corresponds to the fixed number of elastic scatterings. The scattering angle determines a new end point for the particle path.

Still further embodiments of the invention are directed toward a method for commissioning a source model for an electron beam wherein the source model includes a focal electron subsource and a focal photon subsource, both lying on the central axis of a linear accelerator, wherein said source model includes a sampling plane perpendicular to the central axis in which simulated electrons and photons are specified by their position r from the central axis and their energy E, wherein the position r defines an angle theta, and the position r is randomly selected and the particle is assigned a weight through fluence functions for the electron and photon subsources and the energy E is determined through energy spectra for the electron and photon subsources. The method comprising the steps of: selecting an initial estimate for (1) positions of the electron and photon subsource along the central axis, (2) parameters defining the energy spectra for the electrons and photons; and (3) parameters defining the fluence functions for the electrons and photons. One then uses the initial estimate and simulates a plurality of dose distributions, including output factors, percentage depth dose (PDD) curves, and dose profiles. One then compares the simulated output factors to the measured output factors and determines an improved estimate for the positions of the electron and photon subsource along the central axis; compares the simulated PDD curves to the measured PDD curves and determines an improved estimate for the parameters defining the energy spectra for the electrons and photons; and compares the simulated dose profiles to the measured dose profiles and determines an improved estimate for the parameters defining the fluence functions for the electrons and photons.

Another embodiment of the invention concerns a method for defining a source model for an electron beam wherein the source model includes the following: (a) defining a focal electron subsource lying on the central axis of a linear accelerator; (b) defining focal photon subsource lying on the central axis of the linear accelerator; (c) defining a sampling plane perpendicular to the central axis ; (d) specifying fluence functions, which are functions of the position r from the central axis, for each of electrons and photons; (e) specifying energy spectra for each of the electrons and photons; (f) determining the direction of each of the electrons and photons by the straight line direction from the respective focal subsource location to a point in the sampling plane; and (g) specifying a scattering of electrons by varying the direction of the electrons from the determined direction from step f).

Another embodiment of the invention is directed toward a method for commissioning a source model for a photon beam wherein the source model includes a focal photon subsource and a focal electron subsource, both lying on the central axis of a linear accelerator, and an extrafocal photon subsource lying on a plane perpendicular to the central axis, wherein said source model includes a sampling plane perpendicular to the central axis in which simulated electrons and photons are specified by their position r from the central axis and their energy E, wherein the position r defines an angle theta, and the position r is randomly selected and the particle is assigned a weight through fluence functions for the electron and photon subsources and the energy E is determined through energy spectra for the electron and photon subsources, The method comprising the steps of: (a) determining the spatial distribution of said extrafocal photon subsource to fit output factors in air; (b) performing Monte Carlo simulation of radiation transport for a plurality of beamlets, each of which corresponds to subset of energies and angles for said focal photon subsource or the focal electron subsource, and obtaining simulated dose values at each point of a phantom for which there are measured dose values; and (c) using a matrix of said simulated dose values in determining the spectrum and fluence for the focal photon subsource or the focal electron subsource to fit the measured dose values.

According to further embodiments of the invention there is disclosed a method for defining a source model for a photon beam wherein the source model includes the following: (a) defining a focal photon subsource lying on the central axis of a linear accelerator; (b) defining a focal electron subsource lying on the central axis of the linear accelerator; (c) defining an extrafocal photon subsource lying on a plane perpendicular to the central axis of the linear accelerator; (d) defining a sampling plane perpendicular to the central axis; (e) specifying fluence functions, which are functions of the position r from the central axis, for each of the electron and photon subsources; (f) specifying energy spectra for each of the electron and photon subsources; (g) selecting a point in the sampling plane for each electron from the focal electron subsource, each photon from the focal photon subsource and each photon from the extrafocal photon subsource; (h) selecting a point on the plane of the extrafocal photon subsource; (i) determining the direction of the photon from the focal photon subsource and the electron from the focal electron subsource by the straight line direction from the respective focal subsource location to the respective point in the sampling plane; (j) determining the direction of the photon from the extrafocal photon subsource by the straight line direction from the point on the plane of the extrafocal photon subsource to the respective point in the sampling plane; and (k) specifying a scattering of electrons by varying the direction of the electrons from the determined direction from step i).

Yet another embodiment of the invention is directed toward a method of error reduction of Monte Carlo simulation radiation transport. This method comprising the steps of: (a) calculating a dose distribution $f_S(x)$ using a first Monte Carlo simulation using a number, n, of particles and a random number sequence; (b) calculating a dose distribution $g_S(x)$ based on a simplified representation of the radiation transport using a second Monte Carlo simulation with said number of particles n and said random sequence; (c) calculating a dose distribution $g_L(x)$ based on said simplified representation using a third Monte Carlo simulation with a number of particles m where m is greater than n; and (d) reducing the error in the dose distribution $f_S(x)$ by using $f_S(x)-g_S(x)+g_L(x)$ as the error reduced dose distribution.

More generally, the above described embodiment concerns a method of error reduction in radiation transport which performs a Monte Carlo simulation transport calculation to determine a dose distribution in a region of interest; and reduces the error of the dose distribution using control variates.

According to another embodiment of the invention, there is taught a method of accelerating computation of dose distributions in a target area using the steps of: (a) mathematically constructing a fine grid throughout regions of the target area where the density of the target area is non-uniform; (b) mathematically constructing a coarse grid throughout regions of the target area where the density of the target area is uniform; and (c) performing a Monte Carlo simulation of the dose distribution using transport steps defined within the coarse and fine grids wherein in the coarse grid, larger transport steps are used relative to transports steps used in the fine grid.

Yet another embodiment of the invention involves a method of improving the accuracy of a Monte Carlo simulation in radiation treatment planning for particle transport within a target region of interest. This method comprising the steps of: (a) selecting an end point position within the target region of interest; (b) selecting an initial position outside of the target region; (c) selecting at least one intermediate point on a particle path connecting the initial and end positions randomly chosen using a bi-directional probability distribution; (d) repeating step c) for multiple particle paths having different intermediate points; and (e) calculation the total dose within the target region resulting from the summation or average of the doses of the multiple paths.

Embodiments of the invention are further described as a method of improving the simulation of a Compton scattering event in computing dose distributions of radiation resulting from Compton scattering events. This method comprising performing a Monte Carlo transport simulation using an electromagnetic source; determining Compton scattering events along a simulated transport path of the radiation in a treatment region of interest; and at each Compton scattering event, simulating the generation of a plurality of electrons distributed along the transport path.

Another embodiment of the invention includes a method for error reduction of Monte Carlo simulation for radiation transport by postprocessing the resulting energy or dose distribution using at least one of nonlinear filtering or image processing techniques. The radiation transport may be applied to radiation therapy and the may utilize one of the following techniques: (a) a Donoho-Johnstone soft thresholding; (b) a Osher-Rudin equation; and (c) a local cosine method.

BRIEF DESCRIPTION OF THE DRAWINGS

FIGS. 1.1 and 1.2 shows schematic drawings of the treatment setup and the components of the treatment head.

FIG. 2 shows an overall design of the RTP system.

FIG. 3 shows the inputs and outputs for the commissioning process.

FIGS. 4.1–4.3 shows the calibration data used in the commissioning process.

FIG. 5 shows the steps of the commissioning process.

FIGS. 6.1–6.3 show the use of pencil beams.

FIGS. 7.1 and 7.2 show the various source models generated by the commissioning process.

FIG. 7a shows an alternative commissioning process for electron beams.

FIG. 7b shows an alternative photon commissioning method.

FIG. 8 shows the inputs and outputs for the simulation tool.

FIG. 9 shows the overall design of the setup process, including both beam modifiers and patient/phantom setup, for the simulation.

FIG. 10 shows the beam modifiers setup process

FIG. 11 shows details of the animation procedure.

FIGS. 12.1–12.4 show the four kinds of treatment modifiers.

FIG. 13 shows the steps required in the patient setup.

FIG. 14 shows an overall flowchart of the simulation process.

FIG. 15 shows details of simulation in the beam modifiers.

FIG. 16 shows details of simulation in the patient/phantom.

FIG. 17 shows details of the simulation of particle interactions in the beam modifiers and the patient/phantom.

FIG. 18 shows the variance reduction method used in multiple sampling for electrons in Compton scattering.

FIGS. 19.1–19.3 show a comparison of the use of coarse and fine grids for simulation.

FIG. 20 illustrates the use of simulation on a coarse grid as a control variate for simulation on a fine grid.

FIGS. 21.1 and 21.2 show a comparison of the use of simple and complex cross-sections for simulation.

FIGS. 22.1 and 22.2a–22.2c show the details of the bidirectional construction of particle paths.

FIG. 23 shows the steps in use of the bidirectional construction for transport simulation.

FIG. 24 describes the use of multiple voxel sizes.

FIG. 25 shows steps of the postprocessing method.

FIGS. 26.1–26.4 show a comparison of an exact dose profile, a noisy dose profile (as produced by Monte Carlo simulation), the result of linear filtering applied to the noisy profile, and the result of nonlinear filtering applied to the noisy profile.

FIGS. 27.1–27.4 show a comparison of an exact dose profile, a noisy dose profile (as produced by Monte Carlo simulation), the result of linear diffusion applied to the noisy profile, and the result of nonlinear diffusion applied to the noisy profile.

FIG. 28 illustrates the zombie transport method.

FIG. 29 describes the steps in the zombie transport method.

FIG. 30 describes the steps in the uniform transport method, using the Molière tabulation.

FIG. 31 is a diagram showing how accuracy and speed are traded off against each other.

APPENDIX 1 DATA USED BY COMMISSIONING SYSTEM

Figure 30A:
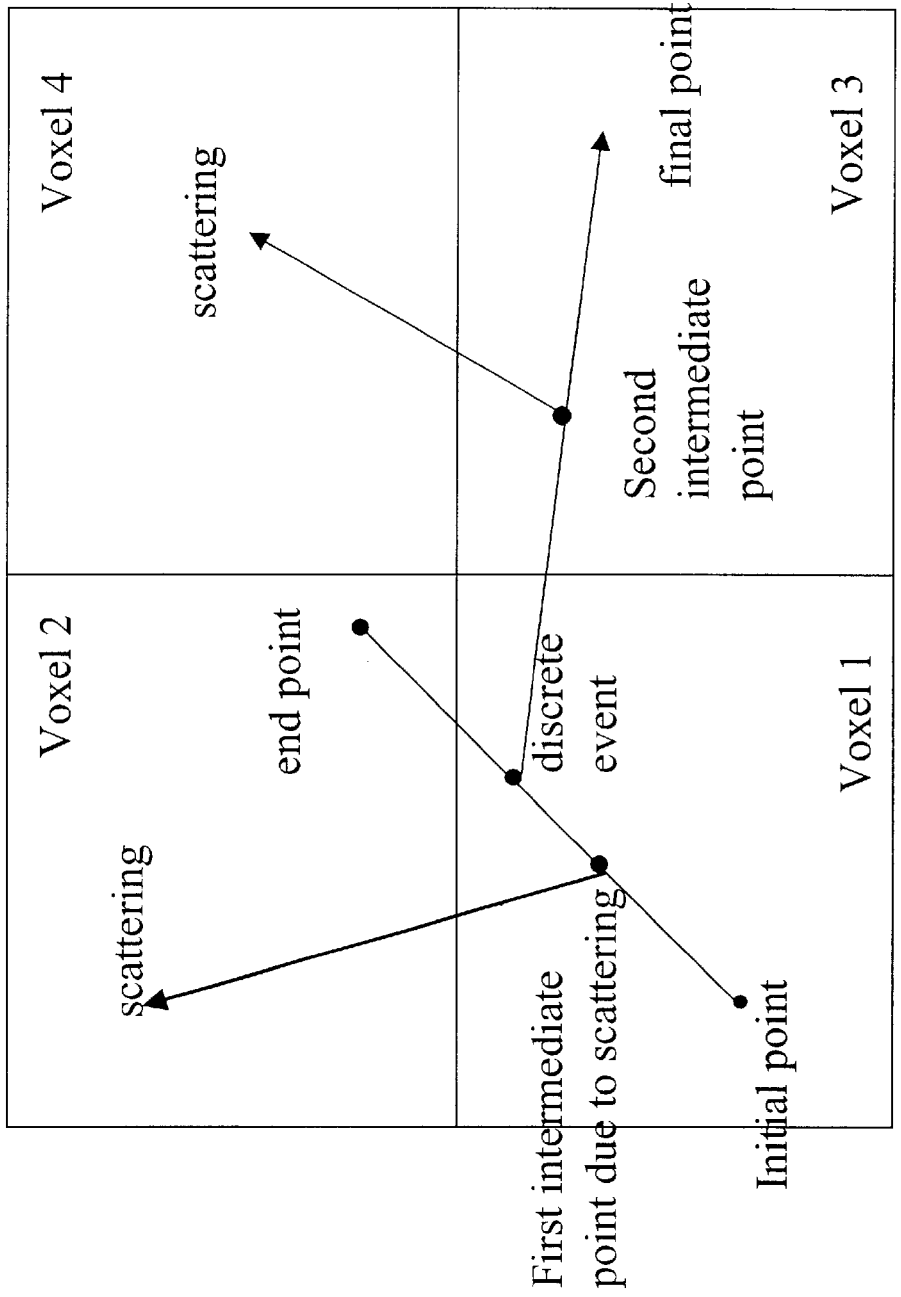
FIG. 30a illustrates the particle scatterings and discrete events in several voxels for the uniform transport method, using the Molière tabulation.

Appendix 1 lists the data required for commissioning of both the electron and photon beams.

DETAILED DESCRIPTION OF THE INVENTION

Overview

An embodiment of the invention is implemented as a software system that performs Monte Carlo dose calculation for radiotherapy treatment planning (RTP). The software system consists of two tools: a beam commissioning tool and a Monte Carlo dose calculation tool. The beam commissioning tool determines the parameters in a source model so that it mimics the radiation output from a clinical linear accelerator starting from a specific set of dosimetry calibration measurements from the linac. The Monte Carlo dose calculation tool simulates the transport of the radiation from the source model through the beam modifiers and then in the patient/phantom. It produces a dose distribution that can be used for dose planning. An overview of the operation of this system is given in FIG. 2.

Before any clinical treatment planning is performed, each linear accelerator must be commissioning by the NXEGS beam commissioning tool. In step 2.1 the calibration data and linear accelerator information are input to the beam commissioning tool. Dose deposition measurements are obtained using a water phantom and in air. A large number of dose deposition values are measure using, for example, a small ion chamber to obtain both scanning and non-scanning data.

In step 2.2, the beam commissioning process is performed; i.e., the dose deposition measurements are used to obtain a linac source model (the commissioning process is further described in FIG. 3). The source model, in step 2.3, is the output of the commissioning process. It consists of a set of subsources, including point subsources, extra-focal subsources, and contamination subsources, which contain secondary particles (e.g., electrons in a photon beam or photons in an electron beam). Additional scattering of a point source may also be used instead of an extra-focal source. For each source, the model may be used to generate a distribution of particle positions, directions and energies; i.e., sampling of the source model produces a set of particles with various energies, directions and positions. The location of the subsources within the treatment head is an adjustable parameter that is used in fitting the measured data.

Once the beam commissioning has been completed, then the NXEGS source model can describe the particular beam in any radiation treatment planning (RTP) simulation. In combination with the NXEGS dose computation tool, it is ready for clinical use by a RTP system for computation of dose to a patient. In step 2.4, a radiation treatment planning (RTP) system connects to the NXEGS system through the application programming interface (API) of NXEGS which serves as an overall system I/O interface. For example, patient CT scan data, previously obtained in input into the system. In step 2.5, patient inputs, including CT scan data and beam modifiers inputs are used as input data to step 2.6 for the setup process. With respect to the patient and bolus, a geometric grid, e.g. 5 mm, is set up, whose outer boundary is the scope. Once a particle leaves the scope it is no longer of interest. Material properties of the patient are input as CT scan values, which are converted into material identification. The properties of the identified material, for example interaction cross sections, are described through the PEGS4 data set.

The beam modifiers include all modifiers that are applied to the radiation beam after it is emitted from the linac. These modifiers may include wedges, cutouts, blocks, MLCs and compensating filters. Details of the setup procedure are given in FIGS. 9, 10 and 13.

In step 2.7 the simulation takes place using the Monte Carlo NXEGS C++ software to calculate particle interactions by the EGS4 algorithm, which provides a dose distribution. In an embodiment of the invention, the EGS4 method is modified by inclusion of a new variance reduction method, i.e. multiple sampling of electrons in Compton scattering. Variance reduction changes the transport algorithm to reduce statistical noise, without introducing a systematic deviation. Other embodiments of the invention utilize new transport methods (zombie transport, the uni-form method and Molière tabulation) to make the transport step more accurate.

In step 2.8, postprocessing is applied to the dose distribution obtained from step 2.7. The postprocessing, a form of nonlinear image processing, extracts information on the statistical error in the computed dose and then uses this information to eliminate some of the error from the distribution.

Finally, in step 2.9, the output is a dose distribution, measured in units of energy deposited per unit mass (Grays), with reduced statistical error. This dose distribution is then output to the RTP system through the API of NXEGS in step 2.10, from which it is then normalized, displayed and analyzed by a dosimetrist in step 2.11.

The Commissioning Tool

The NXEGS beam commissioning system is designed to commission clinical radiation beams for use in the NXEGS Monte Carlo dose simulation system. An overview of the commissioning system and its inputs and outputs is given in FIG. 3.

Commissioning Inputs

In step 3.1, model information on the linear accelerator (linac) is input to the commissioning system. This information includes the manufacturer, the model number and other identifying information, described more fully in Appendix 1. If the treatment head contains any beam modifiers, their description is also needed. Some of the dosimetry measurements are to be taken with a wedge in place in the treatment head.

In step 3.2, information on the linac setup is input to the commissioning system. This information includes the beam modality (i.e. photon or electron beam), the size of the beam, and other characteristics, described more fully in Appendix 1.

In step 3.3, dosimetry data is input to the commissioning system. The dosimetry data consists of actual dose values measured, for example, in a water phantom. The dosimetry data required for the NXEGS beam commissioning is similar to that used by non-Monte Carlo methods, such as Clarkson [20] or convolution methods [21]. As shown in FIGS. 4.1–4.3, this data is of two types: scanning dose data and non-scanning dose data. In accordance with embodiments of the invention, dosimetry data are more reliable (and sometimes more readily available) than manufacturing data specifications. The number of dosimetry data points utilized is selected to be at least 10 points and is preferably about 50 points and most preferably about 100 points or even larger.

In FIG. 4.1, the scanning data (also called the dose profiles) is shown to consist of dose measurements at points along an axis (the x-axis, the y-axis or the diagonal x=y) in the plane perpendicular to the central axis of the beam. Additional scanning data is required at points along the central axis, as shown in FIG. 4.2. In FIG. 4.3, the non-scanning data is shown to be dose measurements at points along the central axis, which is referred to as the Percentage Depth Dose (PDD) data. The dose values at some specified points, both in water and in air, are called the output factors. The set of spatial points within the phantom at which dose values are measured (i.e., the calibration points) will be denoted as $\{x_i\}$, and the dose value at $x_i$ will be denoted as $d_i$. The index i runs from 1 to $N_{dose}$, in which $N_{dose}$ is the number of calibration points. This data is collected for each modality (i.e. photon or electron beam) of the beam, as well as for a plurality of beam energies and beam widths. The more complete specification of the required data is detailed in Appendix 1. Note that although the calibration point for non-scanning data is on the central axis, the set of non-scanning data need not be contained in the set of scanning data. Non-scanning data is required for more values of the energy and width parameters.

Returning to FIG. 3, the NXEGS runs the commissioning process in step 3.4. As described in FIG. 5, it uses Monte Carlo simulation to calculate dose values at the spatial points, beam energies and beam widths that are used in calibration dose measurements. It then compares the simulated dose values and the measured dose values to determine the phase space distribution (PSD) or a sampling method for each of the subsources in the source model.

Step 3.5 shows the source model that is the output of the commissioning system. This source model provides a PSD or a sampling method (cf see the sections on Simplified Procedures for Electron/Photon Beam Commissioning) for the subsources contained in the source model. From this PSD or sampling method, an arbitrarily large number of particles can be sampled for use in simulation of a radiotherapy application. The sampled particles are independent and have initial positions, directions and energies that occur with the correct (non-uniform) probability. The sampled particles provide an accurate representation of the particles emitted from the radiation beam at the exit plane of the linac or some other sampling plane. The subsource types include focal sources, extra-focal sources and contamination sources, as illustrated in FIGS. 7.1 and 7.2. The extra-focal source may be positioned at the scapers. A contamination source may be either or both of a focal source and an extra-focal source.

Subsources and Beamlets

The commissioning process of step 3.4 is described in more detail in FIG. 5. This process starts with dosimetry data, and then uses Monte Carlo simulation to produce a source model that accurately represents the linear accelerator.

In step 5.1, the dosimetry data is input to the commissioning system. The dosimetry data is shown in FIGS. 4.1–4.3.

In step 5.2, the source model is specified as a set of subsources; i.e., a focal source, an extra-focal source and contamination sources. At this step the PSD for each of these subsources is unknown. A particle from one of the subsources is described by its initial position x, direction u and energy e. The initial position is represented by a 3 dimensional coordinate vector x, the direction u is a three-dimensional vector of length 1 (i.e., $|u|=1$), and the energy e is a positive number. Together the phase space value is $w=(x,u,e)$, which is a 7-dimensional vector. Denote the subsource as S, and denote W to be the set of allowable values of w for the subsource S. Due to the constraint $|u|=1$, as well as other possible constraints, the set W is typically a surface of dimension 6 or less within the full 7-dimensional space. For a focal subsource at a point $x_0$, for example, each of the particles has initial position $x=x_0$. The initial positions of an extra-focal subsource are distributed over a spatial region in the linac. A contamination subsource consists of photons for an electron beam or electrons for a photon beam, distributed as a focal source, an extra-focal source or a combination of the two.

In step 5.3, each of these subsources is divided into "beamlets." Each beamlet consists of a small range of the possible values of the phase space vector $w=(x,u,e)$. For each subsource S with phase space set W, the set W is divided into a large number of small, non-overlapping subsets $W_j$, the union of which is W. The beamlet corresponding to $W_j$ is denoted as $S_j$. For each beamlet, the probability density for the choice of initial position, direction and energy of a particle is uniform. This means that every allowable value of $w=(x,u,e)$ in the phase space set $W_j$ for beamlet $S_j$ is equally likely. The set of all beamlets and corresponding phase space sets for the source (i.e. for all of the subsources) is $S_j$ and $W_j$ for j running from 1 to $N_{beamlet}$, in which $N_{beamlet}$ is the number of beamlets.

With this decomposition into beamlets, the source model will be completely described once the amplitude of each beamlet is found. The amplitude $a_j$ for beamlet $S_j$ is a nonnegative number that measures the relative number of particles coming from that beamlet. When a particle is sampled from the source, the probability that it comes from beamlet $S_j$ is the ratio $a_j/A$, in which $A=a_1+a_2+\ldots+a_{Nbeamlet}$. At this point the amplitudes $a_j$ are unknown; they are determined from the dose calibration values using Monte Carlo simulation.

For each beamlet $S_j$, a Monte Carlo simulation is started in step 5.4. First, particles are sampled from the appropriate phase space set $W_j$ in step 5.5. This is performed, using a standard method, by first selecting a vector of random numbers from a random number generator and then mapping the random vector to a phase space point w within $W_j$.

Perform Simulation

In step 5.6, the set of sample points for beamlet $S_j$ is transported through the beam modifiers of the linear accelerator and into the phantom using the NXEGS Monte Carlo simulation system (described in FIG. 8) or a pencil beam algorithm (described in FIG. 6). The output from this dose computation, in step 5.7 is a set of dose deposition values at the calibration points of the measured dosimetry data. More precisely, the dosimetry measurements are an average over the small volume of an ion chamber around the calibration point, and the computed dose deposition values are averaged over a small voxel around the same calibration point.

For a given beamlet $S_j$, denote the computed dose value at calibration point $x_i$ as $m_{ij}$. In step 5.8, this set of dose deposition values $m_{ij}$ from the simulation is collected into a vertical vector $M_j=(m_{ij})$, for fixed j, i.e. for fixed beamlet. This vector is the response of the system, i.e. the set of dose values at the specified points in the phantom, to a unit amount of radiation from the beamlet $S_j$. It forms a column of the "dose transfer matrix" M in equation (3) below.

In step 5.9, the dose computation is repeated for any remaining beamlets, or ended if all the beamlet doses have been computed.

At this point, the matrix M is complete. The matrix M consists of dose values $m_{ij}$, in which i runs from 1 to $N_{dose}$ and j runs from 1 to $N_{beamlet}$. The value $m_{ij}$ lies on the ith row and jth column of M, and it is the value of the dose at the ith point ($x_i$) in the phantom, due to beamlet $S_j$ with unit amplitude. The actual amplitude $a_j$ for beamlet $S_j$ is unknown at this point. Denote the vector of amplitude values as a and the vector of measured dose values as d, given by $$a=(a_1, \ldots a_{Nbeamlet})^\dagger$$

$$d=(d_1, \ldots d_{Ndose})^\dagger. \qquad (2)$$

In equation (2), $a_j$ is the amplitude of beamlet $S_j$ and $d_i$ is the dose at calibration point $x_i$, and the superscript "†" signifies that a and d are column vectors. They satisfy the dose transfer equation $$d=Ma \qquad (3)$$

in which M is the transfer matrix. Equation (3) is solved to obtain the beamlet amplitude vector a in step 5.10, using the measured value of d and computed values of M.

Constraints

A constraint is desirable in order to smooth the effect of statistical noise from the Monte Carlo simulation, discretization error from the pencil beam computation or measurement error in the calibration data. Without the constraint, these errors can be magnified in the commissioning process. Constraints are applied to the dose transfer equation in step 5.11. Two examples for how to apply a constraint are outlined here. A detailed description of the general use of constraints when solving linear equations (not applied to the Monte Carlo problem) can be found in any standard reference on numerical application of constraints, such as [12].

The first example is a (linear) penalization method, in which the transfer equation (3) is modified to $$d = Ma + La \tag{4}$$

in which L is a matrix that expresses the constraint. This equation is then solved for a as $$a = (M+L)^{-1} d \tag{5}$$

in which $(M+L)^{-1}$ is the inverse if M and L are square matrices or the pseudo-inverse if M and L are not square. Another possibility is a nonlinear penalization method in which the term La is replaced by a nonlinear term f(a), and then the resulting nonlinear equation is solved for d:

$$d = Ma + f(a). \tag{6}$$

The second example of a method for applying the constraint is by a projection technique. One first solves the dose transfer equation as $$b = M^{-1} d \tag{7}$$

for a preliminary amplitude vector b, in which $M^{-1}$ is the inverse if M is a square matrix or the pseudo-inverse if M is not square. Then apply the constraint by solving the following (linear or nonlinear) equation:

$$a = g(b). \tag{8}$$

The resulting equations, either linear or nonlinear, are solved for the vector a of beamlet amplitudes in step 5.12. This vector contains the amplitude for each beamlet.

As a specific example of the linear penalization method, consider a constraint that the mean square of the amplitude vector a is not too large. For this constraint, the matrix L in equation (4) is a multiple of the identity matix I, so that equation (5) becomes $$a = (M + \lambda I)^{-1} d. \tag{9}$$

The constraint penalizes (i.e. prevents) large values of the beamlet amplitude $a_j$. In this equation, the constant parameter $\lambda$, which is called a Lagrange multiplier, is chosen based on computational experience to maintain the accuracy of the solution, while preventing beamlet amplitudes that are anomalously large.

As a specific example of the nonlinear projection method, consider a focal source that is constrained to be isotropic and gaussian in energy; i.e. for a beamlet with energy e (i.e. in a small interval around e), the amplitude is $$a_{gauss}(e) = a_0 \exp(-(e-e_0)^2 / \gamma^2) \tag{10}$$

independent of the direction of the beamlet, in which $a_0$, $e_0$ and $\gamma$ are constant parameters that describe the amplitude, center and width of the gaussian energy distribution, respectively. These parameters are chosen to give the best gaussian approximation for the source, as follows: First solve equation (7) for a set of beamlet amplitudes b. Second, choose $a_0$, $e_0$ and $\gamma$ to minimize the following sum $$\Sigma (b_j - a_{gauss}(e_j))^2 \tag{11}$$

in which the sum is for j running from 1 to $N_{beamlet}$, and $e_j$ is the energy of the j-th beamlet. This is an implicit definition of the function g(b) in equation (8). The values $a_j = a_{gauss}(e_j)$ are the final values for the beamlet amplitudes.

Monitor Units

Monitor Units (MUs) for a linac are measured by an ion chamber in the linac. They provide a measurement of the total radiation energy emitted by the linac and its relation to the total dose to the patient. For example, an application of two MUs would result in a dose that is twice that from the application of one MU. Correct matching between the simulated dose and the actual dose for a certain number of monitor units is performed by a normalization factor. This factor, which is determined as part of the commissioning process in order to match the measured output factors in step 5.13, multiplies the dose per particle. The resulting dose is determined in units of cGy per MU. This means that the reported dose is the correct dose for one Monitor Unit, and for a number m of Monitor Units, the reported dose should be multiplied by m, as in step 2.11.

Finally, the source model for the radiation beam is obtained in step 5.14 by normalizing the amplitude vector a so that its sum A is 1. These coefficients then define the PSD, which completely specifies the source model.

Pencil Beam Method

As described above, the pencil beam method [24], which is not a Monte Carlo method, may be used in the commissioning process in order to generate the computed dose matrix M. This process is a useful approximation for electron beams and is illustrated in FIGS. 6.1–6.3. It starts with a continuous beam, as in FIG. 6.1, which is then discretized into a collection of pencil beams in FIG. 6.2. Each of these pencil beams has a dose distribution, indicated by FIG. 6.3. The dose distribution at a point x due to a single pencil beam starting at point $x_0$ in direction u (with $|u|=1$) is the function $f(r, \alpha)$, in which $r = |x - x_0|$ is the distance from $x_0$ to x and $\alpha$ is the cosine of the angle between the vector u and the vector $x - x_0$, i.e., $\alpha = ((x - x_0) \cdot u)/r$. The beamlet dose distribution f is computed as an approximate solution of the Boltzmann transport equations using the Fermi-Eyges theory, as described in [24] or by direct Monte Carlo evaluation. The dose value $m_{ij}$ at point $x_i$ due to the jth beamlet is $$m_{ij} = f(r_{ij}, \alpha_{ij})$$

in which $r_{ij} = |x_i - x_0^{(j)}|$, $\alpha_i = ((x_i - x_0^{(j)}) \cdot u_j)/r_{ij}$, in which $x_0^{(j)}$ is the initial point and $u_j$ is the initial direction for the jth beamlet. The utilization of the above equation for dose computation is known (e.g., [24]), but its application to beam commissioning is a novel embodiment of the invention.

Source Types

The source model types are described in FIGS. 7.1 and 7.2. The focal source, in 7.1, consists of particles that start from a given point with a specified distribution of directions and energies. An extra-focal source, in FIG. 7.2, consists of particles whose initial positions are distributed over a spatial region within the linac, and with a distribution of directions and energies at each point.

For either the focal source or the extra-focal source, an alternative description is to use the exit plane of the linac or some other sampling plane. For each initial position and direction, compute the particle position when it crosses the exit plane. Then use this position as the initial position to obtain the alternative description of the source. Note that on the exit plane or sampling plane the focal source is not concentrated at a point, so that it could be considered as an extra-focal source. On the other hand, it is more convenient to still describe it as a focal source in a different representation. Use of this representation does not change the commissioning procedure.

Note that the source model describes the radiation particles that leave the exit plane of the linac or some other sampling plane. In the commissioning process, a wedge may be present in the beam modifiers. While other beam modifiers may be treated in the commissioning computations, it is generally preferable to treat them in the actual dose simulation (FIG. 8), since they vary from patient to patient. Beam modifiers will affect the resulting dose distribution and the commissioning computations, but the resulting source model is unchanged (within the numerical accuracy of the simulation); i.e., the vector d and the matrix M in equation (2) are changed in a consistent way so that the vector a is unchanged.

A Simplified Procedure for Electron Beam Commissioning

As an alternative to the general commissioning method described above, a simplified procedure for electron beams is developed as part of NXEGS as shown in FIG. 7a.

Source Model

In this simplified method, the source model for an electron beam consists of two subsources, a photon subsource and an electron subsource. See steps 7a.1 and 7a.2 of FIG. 7a. Both subsources are focal sources placed at a point on the central axis of the linac in step 7a.3. There are no extra-focal sources; instead some scattering is applied to the electrons. Particles from the source are sampled at a sampling plane which lies at the top of the first scraper.

The additional scattering of the electrons is a change in direction only. The angular change is chosen from a gaussian distribution, depending on electron energy and distance to the focal point from the point in the sampling plane.

Both photons and electrons have a variable spectrum and fluence as in steps 7a.4 and 7a.5 respectively. The spectrum is the distribution of particle energy. It is represented by a histogram in energy, including a number of peaks, and depending on a small number of parameters, such as the widths and positions of gaussian distributions in energy.

The fluence is the density of particles passing through each point of the sampling plane. Since the particles are all emitted from a point source, the choice of location on the sampling plane is equivalent to the choice of particle direction from the point source; i.e., the particle direction is the direction from the point source to the sampled point on the sampling plane. Particle positions in the sampling plane are chosen at random with a uniform density; the fluence is accounted for by assigning a weight to each particle that is proportional to the fluence (density) at that point. The fluence is taken to be a polynomial function of the radius r (i.e., the distance in the sampling plane from the central axis). The scattering of the electron source is determined by the in-air scattering function.

Calibration of the Source Model

The parameters in the source model are each determined by matching to specific commissioning data as in step 7a.6. The position of the subsources on the beam axis is determined by fitting to the set of output factors from a simulation (step 7a.7). The spectra of the photon and electron subsources are determined by fitting the simulated PDD values to the measured PDD values; i.e. the dose values on the central axis. The fluence of the photon subsource is determined by fitting the simulated dose profile to the measured dose profile at large depths, at which there are no electrons. The resulting simulated dose from the photon subsource alone is then subtracted from the measured dose profiles at smaller depths to extract dose profiles due to electrons alone. Then the fluence of the electron subsource is determined by fitting the simulated dose profiles due to only the electron subsource to these extracted dose profiles. A correction to this method is made to account for photons that reach large depths after being generated by scattering of electrons to obtain the does distribution (step 7a.8).

Numerical Algorithm

The algorithm for performing the fitting is iterative, since the parameters for the fluence and spectrum are nearly, but not completely independent. First the spectrum is determined for each subsource, then the fluence is determined for each subsource, then the normalization factor and the subsource positions are determined. This process is repeated several times. For each step in the process a nonlinear fitting is used to determine the parameters in the source model. This uses a simple search method to find the choice of parameter that minimizes a chi-square fit to the data as, for example, described in [12].

In order to perform this fit, determination of the simulated dose is required. This simulation uses Monte Carlo transport of photon and electrons in the treatment head, followed by a pencil beam computation in the phantom.

In sampling a particle from either the photon or electron subsources, selection of the particle position in the sampling plane and the particle energy, as well as the scattering angle if the particle is an electron, must be performed by sampling from the corresponding distribution. This sampling may be performed using a standard random number generator. To reduce statistical errors, an alternative is to perform the sampling using a quasi-random sequence, such as the Sobol or Halton sequence [12]. A quasi-random sequence is a sequence of points that is more uniformly distributed than a random sequence. The n-th entry in a Halton sequence is obtained by reverting the digits in the base p representation of n around the decimal point for some prime number p. A Sobol sequence is obtained by selecting the best points from a lattice consisting of multiples of inverse powers of 2.

A Simplified Procedure for Photon Beam Commissioning

As an alternative to the general commissioning method described above, a simplified procedure for photon beams is developed as part of NXEGS and illustrated in FIG. 7b.

For a given energy, the photon beam commissioning process produces a beam model that includes the effect of variable field size, which is specified at the time of simulation through the opening of the collimator jaws. This is in contrast to the electron commissioning process, in which a separate beam model is produced for every combination of energy and field size.

Source Model

In this simplified method, as shown in FIG. 7b, the source model for a photon beam consists of three subsources, a primary (focal) photon subsource in step 7b.1, an extrafocal photon subsource in step 7b.2 and one electron subsource in step 7b.3. The focal photon subsource and the electron subsource are point sources lying at the center of the target. The extrafocal photon subsource is distributed on the flattening filter, with a spatial distribution that consists of one or more gaussian distributions. Particles from the source are sampled at a sampling plane. The position of the sampling plane is on the lower surface of the lower jaws.

The energy spectrum for each of the three subsources is taken to be piecewise constant functions, the values of which are determined as part of the commissioning. For the primary photon subsource, the spectrum also depends on the angle between the photon direction and the beam axis, while the other two subsources each have a single spectrum.

The fluence is the density of particles passing through each point of the sampling plane. Since the particles from the primary photon subsource and the electron subsource are emitted from point sources, the choice of location on the sampling plane is equivalent to the choice of particle direction from the point source; i.e., the particle direction is the direction from the point source to the sampled point on the sampling plane. Particle positions in the sampling plane are chosen at random with a uniform density; the fluence is accounted for by assigning a weight to each particle that is proportional to the fluence at that point. The fluence is taken to be a piecewise constant function of the radius r (i.e., the distance in the sampling plane from the central axis). For the extrafocal photon subsource, the sampling at the sampling plane is done in the same way as for the primary subsource. In addition, a point on the subsource itself is sampled, using the gaussian distributions describing the extrafocal subsource. The direction between these two points is then used for the particle direction.

When sampling the primary and extrafocal subsources, weights are applied based on the distances from the subsource to the sampling plane and the solid angles determined by the jaw opening.

Simple scattering in air is performed for the electrons from the electron subsource. Effects of backscatter from the collimator are accounted for by a weight factor that is bilinear in the jaw opening.

Calibration of the Source Model

The width and weight of the gaussian distribution for the spatial location of the extra focal subsource and the collimator back scatter coefficients are determined to fit the output factors measures in air at some point on the beam axis at different field sizes in 7*b*.4. This is a nonlinear fit that is performed iteratively.

The remaining beam model parameters are determined using simulated values of the dose in a water phantom at all of the points for which there is measured data. This simulation uses Monte Carlo transport of photon and electrons in the treatment head and the phantom. At every field size and source-surface distance (SSD), the energy deposition at each of the in-water measured points is computed by simulation for every energy-angle bin of the primary subsource (along with the associated extrafocal sub-source) and for every energy bin of the electron subsource in 7*b*.5. These resulting simulated values form a dose transfer matrix that is used to determine the remaining parameters of the beam model. The amplitude of the source in each of these bins depends nonlinearly on the parameters of the spectra and energy, but the resulting dose distribution in the phantom depends linearly on the bin amplitudes with coefficients that come from the dose transfer matrix. Using this relationship, the remaining parameters of the spectra and fluence are determined in 7*b*.6 to give the best fit to the measured data.

Simulation

An overview of the dose computation system (e.g. simulation) and its inputs and outputs is given in FIG. 8. FIG. 8 represents details of steps 2.6 and 2.7 of FIG. 3. The inputs are patient CT scan data in 8.1, the linac source model as produced through the commissioning process (cf. FIG. 5) in 8.2, and the beam modifiers description in 8.3. These are used in step 8.4 to setup the simulation, as described in FIG. 9. After the simulation is applied in 8.5, the output is the radiation dose in 8.6 corresponding to step 2.9 in FIG. 2. The source model may be found by the commissioning process or may be input from a linac that has already been commissioned.

Setup

Before the actual particle transport can be performed, the patient and beam modifiers setup must be completed. This is described schematically in FIG. 9.

First in step 9.1, the source model is determined to match the parameters of the radiation beam that is employed in the radiotherapy exercise. The source model depends on the modality, energy and beam width of the linac. In addition, the monitor units (MUs) are adjusted to account for variations in the jaw width, for simulation of a dynamic wedge.

In step 9.2, the details of the beam modifiers are input. This includes the geometric configuration of the beam modifiers, the material composition of all of the components and a description of the dynamics (animation) of the beam modifiers, if they are moved during the planned therapy. In step 9.3, the description of the beam modifiers is used to setup the beam modifiers. The setup provides data on the beam modifiers in a form used by the simulation.

Note that the components of the beam modifiers differ for different patients and may vary as a function of time (in dynamic treatment) during treatment, so that setup and transport through the beam modifiers must be performed as part of each dose planning exercise. In contrast, the linac does not change, except through a few parameters (modality, energy, beam width and jaw openings), so that the beam model is the same for each dose planning exercise.

In step 9.4, the CT data, which are obtained from a conventional CT scan, are input. The CT data describe the density of the patient at each point (actually at each of a set of small, three dimensional cubes called grid cells). In step 9.5, a geometric grid is created for the simulation. Then the CT data for each grid cell (or voxel) is converted into material properties and related to standard materials in the PEGS4 data set. In addition, the bolus, if used, is inserted into the grid. This completes the patient setup.

Finally in step 9.6, the setup serves as input to the simulation system (step 8.5), which then computes the particle transport and dose deposition.

Setup for Beam Modifiers

Next the input and setup for the beam modifiers are described, as illustrated in FIG. 10 and as corresponding to steps 9.2 and 9.3 of FIG. 9. Within the beam modifiers, NXEGS groups the different beam modifiers into four types: an animated solid (polyhedron in FIG. 12.1), an elevation grid (a compensating filter in FIG. 12.2), a multi-leaf collimator (MLC in FIG. 12.3), and a custom port (FIG. 12.4). A fifth type of modifier, called a "soft wedge", is used to describe moving jaws. These components are listed in a beam modifiers component list, in step 10.1

For each of the 5 types of beam modifiers, geometry and material properties are required for the setup. In addition, dynamics (i.e. motion) of the beam modifiers is described through animation. Animation can occur for the animated solid, MLC and soft wedge, as well as for the beam modifiers as a whole. This is put together to get animation frames for description of the beam modifiers (cf. FIG. 11).

Simulation of transport in the treatment head uses a computational "scope" and a "trap". The scope is a finite volume bounded by a single polyhedral shape that contains the entire beam modifiers. The particle source should be entirely contained within the scope. Particles that leave the scope are discarded. The scope contains a trap, which is a planar surface on which particles are "collected" within the simulation. The traps serve to pass the particles from the beam modifiers assembly scope to another finite volume bounded polyhedral shape containing the patient or phantom. The trap is chosen so that it captures all of the particles from the beam modifiers that would hit the patient/phantom scope. All particles of interest pass through the traps, so that the PSD from the treatment need only be determined on the traps.

An animated solid, in step 10.2, is a beam modifier, such as a wedge or block, that can be described as a polyhedron (cf. FIG. 12.1). The polyhedron may be static or it may be moving, i.e. animated, as described below. Each animated solid modifier is described by specification of its geometry, material properties and animation, in step 10.3.

An elevation grid is used to represent a compensating filter, in step 10.4. This is a beam modifier that has a flat side opposite a side with a curved shape of arbitrary complexity (cf. FIG. 12.2), which is designed to provide a precisely structured radiation beam cross-section. The flat side of the compensating filters may face either toward or away from the source. Its geometry and material properties are input in step 10.5.

The custom port of FIG. 12.4 is solid in the shaded perimeter region and open in the center. Mathematically, this port may be described either as a blocking port or a cutout port, in step 10.6. Its geometry and material properties are input in step 10.7.

In step 10.8, a multi-leaf collimator (MLC) is included. An MLC is described in step 10.9 by specification of the geometry, material properties and animation of its leaves (cf. FIG. 12.3). These include the direction of leaf motion (i.e. whether leaves travel along the x-axis or the y-axis in the beam coordinate system), the size and location of each leaf, the number of leaf pairs, and the thickness, density, and PEGS4 material name of the leaves. For each frame of the animation, the positions of the leaf pairs are all specified.

A soft wedge, in step 10.10, is used to describe animation of the source due to moving jaws. There are four types of soft wedges, corresponding to which of the four jaws (lower, upper, left, right) is moving. Its geometry, material properties and animation are input in step 10.11.

In addition to the motion of beam modifiers within the treatment head, the treatment head itself may move, as specified in step 10.12. This is combined with the description of all of the beam modifiers in step 10.13 to give a complete description of the beam modifiers and their dynamics.

Dynamic treatment is described in NXEGS using a series of "frames", each of which consists of the position and geometry of the dynamic component at a certain time. If necessary, the component geometry at intermediate times is determined by interpolation between the frames. Three slightly different approaches are used in the representation. The beam orientation is described by a sequence of static frames, each of which represents the beam over a time interval, with intervals of equal length. Animation of modifiers is also described by a sequence of static frames, but each frame comes with a weight that determines the relative time interval corresponding to that frame. Animation of the photon jaws uses linear interpolation between two or more frames to provide the position of the jaws at any intermediate time. The time for each simulated trajectory is chosen at random. For every dynamic element, the whole animation trajectory is mapped to the unit time interval from 0 to 1, and for every inserted particle a uniform random time is chosen for its insertion. Particle weights are numbers given to each particle, which multiply the energy deposition for that particle and all of its daughter particles, as used earlier in EGS4. Use of particle weights for animation of dynamic beam modifiers is new in NXEGS. In other words, the weight associated with each frame (corresponding to the desired time interval for that frame during a Monte Carlo simulation) is attributed to the emitted particle so that the particle weight will automatically reflect the significance (in a time sense) of the frame relative to the other frames. Each emitted particle's weight then corresponds to the weight assigned to each frame.

The dynamics of the treatment head is described in a hierarchical way, as in the key-frame technique of computer graphics [10]. In this description, the positions of components of an object are described relative to the object. This implies, for example, that the motion of a treatment head can be fully described by its position and direction and that the beam modifiers within the treatment head will then move along with the treatment head. Dynamics of a beam modifier is specified only if the beam modifier moves relative to the treatment head.

A flowchart for the animation process is given in FIG. 11. First in step 11.1, set the initial position of the beam modifiers. In the case of static treatment, this is also the permanent position of the head. In the case of dynamic treatment, subsequent frames are defined.

In step 11.2, a list of frames is input, describing the motion or dynamics of the beam modifiers and their components, as discussed above. In the simple case that a beam modifier does not move, then the animation sequence consists of only a single frame. For each particle that is emitted from the source (step 11.3), a random time is selected, as in step 11.4, and the corresponding frame (or linear interpolation of frames) with its associated or corresponding weight is determined, in step 11.5. This serves as input to the simulation in step 11.6.

Schematic diagrams of beam modifiers are shown in FIGS. 12.1–12.4, including a polyhedral beam modifier in 12.1, a compensating filter in 12.2, an MLC in 12.3 and a custom port in 12.4.

Patient Setup

The next step is the patient setup, which is described in FIG. 13. The patient setup consists of its geometry and material properties, as well as a set of patient options. The bolus (if any) is considered as part of the patient.

The patient setup starts with input of the patient CT scan data in step 13.1 corresponding to steps 8.1 of FIG. 8 and 2.5 and 2.6 of FIG. 2. From the CT numbers, values of density for the material of the patient are obtained through a standardized linear relation.

Next in step 13.2, a patient geometry is constructed, to be consistent with the CT data and the desired treatment region. The patient geometry consists of a rectangular set of voxels, defined by a rectangular grid, in the patient coordinate system. The scope of the patient is chosen to be large enough to contain the matrix of voxels and the trap of the treatment head. Simulation is only performed within this region, so the region must be selected large enough that any backscatter from outside scope is not significant. The position of the patient matrix, in the patient coordinate system, is specified by the three most negative values of the coordinates. In addition, the relative position of the beam modifiers and the patient is described through a transformation between the two coordinate systems. Note that there is no need to construct voxels or a grid in the beam modifiers geometry, since dose distribution in the beam modifiers is not reported, and material properties in the beam modifiers are defined by the boundaries of the beam modifiers.

Patient material properties originate from image data consisting of density values from a CT scan, as in conventional RTP systems. In step 13.3, the corresponding material in the patient geometry is determined by a mapping from the material density, as measured by CT scan numbers, to electron densities. NXEGS contains a default mapping, but this may be replaced by user-supplied mapping. This mapping is described as follows: First a number of mass density values are prescribed. These serve as "breakpoints" that define intervals of mass density values. Within each of these intervals (i.e. between two breakpoints), the map between mass density and electron density is linear, with coefficients that change from one interval to the next.

Based on this electron density value, the material type is identified. Each voxel is assigned a media identifier, which is a PEGS4 data name, in step 13.4. PEGS4 data consists of the transport parameters for the materials involved in the radiation transport. The transport parameters include scattering cross sections and other interaction parameters that depend on the molecular and atomic structure of the different materials. These are specified from a set of standards, such as those of ICRU (International Commission on Radiation Units and Measurements). This use of PEGS4 by NXEGS is similar to the use of PEGS4 by EGS4.

A bolus is inserted into the patient grid by changing the media type (i.e. the density and PEGS4 name) in some voxels of the patient grid, in step 13.5. The geometry of the bolus is directly measured, and its material properties should be readily available. Finally, in step 13.6 the geometry and material properties of the patient and bolus are put into a data structure, which is the output of the patient setup, and in step 13.7 this is input to the simulation process.

Transport

Next, simulation (step 2.7 of FIG. 2 and step 8.5 of FIG. 8) and scoring (i.e. dose deposition) are described. The simulation procedure is outlined in FIG. 14. First in step 14.1, the source models (cf. FIG. 7), beam modifiers setup (cf. FIG. 10) and patient setup (cf. FIG. 13) are input into the system. Next, in step 14.2 the simulation is performed in the beam modifiers (cf. FIG. 15) and in the patient (cf. FIG. 16). This starts from source particles chosen from the PSD of the source model, as determined in the commissioning process. Afterwards, in step 14.3 the resulting energy deposition is converted to dose, by division by the density in each voxel. In step 14.4, the resulting dose values are postprocessed to reduce statistical error (cf. FIG. 25). The final output is the dose distribution in step 14.5.

Simulation in the beam modifiers is illustrated in FIG. 15. First particles are sampled from the source model in step 15.1. The simulation for the sampled particles consists of a series of transport steps, interactions and generation of secondary particles, using the primary and secondary particles, in step 15.2. In each of these steps, transport through most beam modifiers, including animated solids and compensating filters, is computed by full Monte Carlo simulation in step 15.3. For details of the simulation of particle interactions, see FIG. 17. For the MLCs and custom ports, however, particle transport is performed by a throughput function in step 15.4. The throughput function allows a certain fraction of particles that are incident on the beam modifier to pass through; the remainder are removed from the simulation. This simplifies transport through a uniformly dense and uniformly thick beam modifier which are characteristics of the MLC (FIG. 12.3) and the custom port (FIG. 12.4).

At the end of a simulation step, several tests are made to determine the next step, just as in EGS4. If a particle's energy falls below a cutoff energy value, as checked in step 15.5, the particle is discarded in step 15.6. If a particle hits the trap, as checked in step 15.7, it is stored for use in the simulation in the phantom (cf. FIG. 16) in step 15.8. If a particle leaves the scope, without hitting the trap, as checked in step 15.9, it is discarded in step 15.10. Otherwise, the simulation is continued by returning to step 15.2 for each particle. In addition, new particles are created in the simulation process and their transport is simulated while the parent particle is stored in step 15.11. This process is continued until all of the particles (primary and secondary) are either discarded, hit a trap or leave the scope. Note that energy deposition in the beam modifiers is not reported.

Particle transport in the patient (phantom), including any bolus, is computed through Monte Carlo simulation, as illustrated in FIG. 16. The input in step 16.1 to the simulation in the patient is the particles from the beam modifiers trap, as generated in FIG. 15. The initial position of these particles in the patient/phantom coordinates is determined from their position in the trap of the beam modifiers by a linear relation between the two coordinate systems.

The simulation for the sampled particles consists of a series of transport steps, interactions and generation of secondary particles, in step 16.2. During the transport, the simulated particles interact with the material of the patient in step 16.3, depositing energy and creating new particles, as further described in FIG. 17.

At the end of a simulation step, several tests are made to determine the next step. If a particle's energy falls below a cutoff energy value, as checked in step 16.4, the particle is discarded and its energy is deposited in the nearby cells in step 16.5. If a particle leaves scope, as checked in step 16.6, it is discarded in step 16.7. Otherwise, the simulation is continued by returning to step 16.2 for each particle. In addition, new particles, created in the simulation process, are simulated while the parent particle is stored, in step 16.8. This process is continued until all of the particles (primary and secondary) are either discarded or leave scope.

The particle interactions in NXEGS are described in FIG. 17. For an incoming particle in step 17.1, the possible interactions are grouped here as discrete photon interactions in 17.2, discrete electron interactions (including multiple scattering) in 17.3 and continuous energy deposition in 17.4.

The simulation step produces deposition of energy from the interaction in 17.5. Next, the energy and position of the scattered primary particle are checked (as in FIGS. 15 and 16) in 17.6. In step 17.7, new secondary particles are generated from the particle interactions. A secondary particle is then simulated while the parent particle is stored, as in 17.8. Secondary particle simulation includes the new variance reduction method for multiple sampling of electrons produced by Compton scattering, as described further in FIG. 18.

Acceleration Methods

A number of acceleration methods including variance reduction have been developed.

Some of these variance reduction methods work by splitting particles into multiple representative particles at certain points in the transport simulation. The increase in the number of particles is balanced by assignment of a weight to each of the particles. For example, if a given particle of initial weight w is split into 4 particles, then each should be given weight w/4 (or more generally a set of weights that add to w). Secondary particles inherit the weight of their parent particles. At the end, the dose deposited by a particle is multiplied by the weight of the particle.

The reason for employing particle splitting and weights is to optimize the use of the particles. For simple interactions (i.e. cross sections with little variation), relatively few particles are needed to get an accurate sample of the effect of the interaction. For complex interactions (i.e. cross sections with a lot of variation) many particles are needed to adequately sample the interaction. So the simulation is performed most efficiently if few particles are used for the simple interactions, but the few particles are split into many when a complicated interaction occurs.

Multiple Electron Sampling for Compton Scattering

Monte Carlo transport in both beam modifiers and patient/phantom is effectively identical to that of BEAM and EGS4, respectively, with a few exceptions. A new variance reduction method for Compton scattering, which is illustrated in FIG. 18, is included in NXEGS. Compton scattering is the scattering of photons off of electrons, which can impart energy to the electrons. The effect of Compton scattering on the photons is unchanged from EGS4, but the electron interaction is changed. In EGS4, a single electron may be generated by a Compton event. Whether or not an electron is generated, as well as its energy and direction, is determined by random sampling from an appropriate cross section, given by PEGS4. In NXEGS, each generated electron is replaced by a plurality of m electrons, each with a fractional weight 1/m. These multiple electrons may all have the same energy and direction. The direction is randomly chosen around the photon direction using the cross section from PEGS4. The resulting electrons set in motion by Compton scattering are distributed over the path of the incident photon. The electrons are treated as secondary electrons in steps 15.11, 16.8 and 17.7.

Starting from the incident photon in step 18.1, a Compton scattering event is chosen from the cross section in 18.2. The photon deflection is the same as in conventional EGS4, as shown in 18.3. The electron, however, is multiply-sampled with a weight that compensates for the multiple samples, in step 18.4. The multiple electrons are distributed along the path of the incident photon in step 18.5. The use of multiple electrons, and the accompanying weights, for Compton scattering is a new application of the general method of particle splitting for variance reduction, as described above in "Description of Related Art".

Distribution of the multiple electrons along the path of the photon is done uniformly with a step equal to the mean free path (MFP) multiplied by a weight fraction. In NXEGS the multiple electrons are distributed along the path of the photon before the Compton interaction, but they also can be distributed along the path after the interaction or both. before and after the interaction. A random offset x, having value between 0 and 1 inclusive, is applied to this sequence. That is, the electrons are sampled at the points with the coordinates (x+n)*MFP/m where m is the splitting factor (generally fixed at a value, e.g., between 1 and 10), x is random offset, and n is a nonnegative integer varying from 0 to m−1, for each offset value x. The electrons are independently sampled using the relevant scattering cross-section. If no secondary electron is produced in any of the n samples of the Compton event, then there is no electron for that position. As a result the number of produced electrons is stochastic.

Additional Variance Reduction Methods

Three new variance reduction methods for acceleration have been developed for NXEGS: control variates, bidirectional path construction and multiple voxel size.

Control Variates

The first of these new variance reduction methods is the control variates method. Control variates have been used extensively for Monte Carlo computation of integrals [22 pp. 107–109], but have not been used for Monte Carlo simulation of radiation transport. The integral of a function f(x) can be written as the statistical average E[f(x)] of f(x) in which x is a random variable. This average can be estimated by an average of values $f(x_i)$, for l=1, . . . ,N, in which the $x_i$'s are Monte Carlo samples of the random variable x. The control variate method uses another function g that is similar to f. The average of f is then represented as $$E[f(x)]=E[(f(x)-g(x))]+E[g(x)]. \quad (13)$$

Monte Carlo simulation is then applied to the average of f−g, rather than that of f. The average of g is assumed to be either known exactly or else easily computed. If the variance of f−g is smaller than that of f, then this results in considerable error reduction.

The same procedure can be used for Monte Carlo simulation of radiation transport. In equation (13), let x denote an entire particle trajectory (more precisely, a shower) and let f(x) represent the resulting dose distribution in a given set of voxels. The average E[f(x)] is then the average dose distribution, which is simulated by the Monte Carlo procedure described above by random sampling of the particle trajectories x. So, the control variate method for radiation transport involves choice of a function g(x) that is an approximation to the dose distribution f(x).

Several examples of the simplified transport are presented here. The first example of control variates is to use larger voxels (i.e., a coarser grid). Radiation transport is easier to compute for larger voxels because there is a smaller memory requirement and there are less boundary crossings to compute. Use of the dose deposition on a coarse grid as a control variate for dose deposition on a fine grid is a new method, but is related to the postprocessing methods described below. A second example of control variates is to use simplified cross sections. Radiation transport with simplified cross sections is faster because it is easier to sample from the cross sections and because less particles are required for the same accuracy. These two examples are discussed in detail below.

FIGS. 19.1–19.3 and 20 illustrate the use of simulation on a coarse grid as a control variate for simulation on a fine grid. In this example, the function f in (13) is the dose distribution on the fine grid, the function g is the dose distribution on the coarse grid and the variable x stands for a particle trajectory. FIG. 19.1 shows that simulation on the coarse grid allows longer steps. FIG. 19.2 shows that simulation on the coarse grid may be performed with short steps. Finally, FIG. 19.3 shows how simulation on the fine grid requires short steps. It may be seen that simulation is faster on the coarse grid. To emphasize the differences between these three computations, we rewrite (13) as $$E[f_S(x)]=E[(f_S(x)-g_S(x))]+E[g_L(x)], \quad (14)$$

in which $f_S$ is the dose computed by small step size on a fine grid, $g_S$ is the dose due to small step size on a coarse grid, and $g_L$ is the dose due to large step size on a coarse grid.

In step 20.1 of FIG. 20, simulation on the fine grid is performed using a relatively small number of particles. In step 20.2 the same simulation, with the same number of particles, the same step size and the same random number sequence, is performed on the coarse grid, and the resulting coarse grid dose distributions is subtracted from the fine grid dose distribution in step 20.3. Because of the correlation between these two dose distributions, the resulting dose difference has a very small error. Moreover, this computation is fast because of the small number of particles. In step

20.4, the simulation is repeated with a larger number of particles for the same coarse grid. This computation is fast because it involves fewer boundary crossings and accurate because of the large number of particles. Then in step 20.5 the coarse grid dose distribution is added to the previous dose difference, as in (13) to get a correct dose distribution. Although this method requires extra computational work (i.e., computation on both the fine grid and the coarse grid), the increased accuracy can make the method quite efficient, so that on balance the method is both accurate and fast.

The use of a simplified cross section is similar. FIGS. 21.1 and 21.2 show a simplified cross section (FIG. 21.1) and a complex cross section (FIG. 21.2). In this example, the function f in (13) is the dose distribution for the original complex cross section, the function g is the dose distribution on the simplified cross section, and the variable x stands for a particle trajectory. As in the example of a fine grid and a coarse grid, computation for the simplified cross section is faster and more accurate, both because the cross section is simpler and because more particles can be used. First compute the dose, using a relatively small number of particles, for both the complex and simple cross-sections, and take the difference of these two doses. Then compute the dose, using a large number of particles, for the simple cross-section. Finally add the dose distribution for the simple cross-section to the previous dose difference. The resulting method is both accurate and fast.

The above described example illustrates an embodiment of the invention in which the dose distributions $f_S(x)$ and $g_S(x)$ are calculated using a parameter such as step and grid size (small step size on a coarse grid for $g_S$ as in FIG. 19.2, small step size on a fine grid for $f_S$ as FIG. 19.3) or cross section (complex cross section of FIG. 21.2) with the same relatively small number of particles and the same random sequence for selecting the particles. In contrast the dose distribution function $g_L(x)$ is calculated using a simplified representation of the same parameter, such as step and grid size (large step size on a coarse grid per FIG. 19.1) or cross section (simple cross section of FIG. 21.1) but using a much larger number of particles to increase the sample population, thus reducing error. Clearly the parameters of step and grid size and cross section are representative and non-limiting examples.

Bidirectional Construction

A second new variance reduction method is that of bidirectional path construction. Bidirectional construction is one that allows the transport path to be constructed from both its start and its end, rather than sequentially from its start, as in a standard method. This was first developed for light ray tracing in image processing [23]. The advantage of a bidirectional construction for radiation transport is twofold. First, some regions of the patient are of more interest than others, e.g. the cancerous region and nearby sensitive tissues are of particular importance. Second, the error in a voxel is inversely proportional to the square root of the number of particles in the voxel, and directly proportional to the weight multiplier of the particles. In order to obtain a uniform accuracy level throughout the region, put more particles with smaller weights in the regions of high dose. The bidirectional construction is used for the multiple scattering process for the electrons, which is the dominant part of the transport process for either an electron beam or a photon beam.

The direct and bidirectional constructions are compared in FIGS. 22.1 and 22.2a–22.2c. FIG. 22.1 shows a direction construction, which sequentially constructs the 4 steps in the particle path from point x0 to point x4. The point x4 is located in a given voxel of interest. The total dose within the given voxel would include all direct paths that have a point within (or that pass through) the given voxel. FIGS. 22.2a–22.2c shows the bidirectional construction, which uses successive subdivision of the path from x0 to x4. In FIG. 22.2a, the beginning and end points x0 and x4 are first chosen and a single path is constructed from x0 to x4. This path is split into two segments in FIG. 22.2b, and each of these two segments is split into two more paths in FIG. 22.2c. The splitting of the paths is done to achieve the smaller step sizes used in the Monte Carlo beam simulation.

Use of the bidirectional construction in the transport simulation is illustrated in FIG. 23. In step 23.1 the initial position, direction and energy are sampled for a particle. In step 23.2 the final values are chosen within the region of interest (e.g., in the cancerous region or in sensitive tissues), and in step 23.3 the intermediate values are constructed by successive subdivision. In step 23.4 a weight is calculated to correct for any error in the probability of the bidirectional path construction, and in step 23.5 that weight is used to average the dose distribution. Utilizing weights to average results is known as in the method of importance sampling [22 pp. 92–103, 23].

The direct construction is stochastic and is described by a transition probability. Consider a path $x_D=(x_0, x_1, x_2, \ldots, x_n)$ generated by the direct construction. The initial point $x_0$ is chosen from some initial probability density $p_0(x_0)$. Then the next point $x_1$ is chosen according to a conditional probability density $p_D(x_1|x_0)$, which is the probability for choosing the point $x_1$ given that the preceding point is $x_0$. Then the next point $x_2$ is chosen according to the conditional probability density $p_D(x_2|x_1)$, which is the probability for choosing the point $x_2$ given that the preceding point is $x_1$. Continuing on this way all of the points are chosen from their distributions. The resulting probability density $p_D(x_D)$ for the whole path $x_D$ is the product $$p_D(x_D)=p_0(x_0)p_D(x_1|x_0)p_D(x_2|x_1) \ldots p_D(x_n|x_{n-1})$$

Consider a particular voxel and define $d(x_D)$ to be the dose in that voxel resulting from the path $x_D$. The total dose within a given voxel from the direction construction is $$d=E[d(x_D)]=\Sigma p_D(x_D)d(x_D)$$

in which the sum is over all of the paths generated by the direct construction.

The bidirectional construction differs from this direct construction mainly in the order with which the points are determined. In the direct construction, the points are chosen in the consecutive order: first $x_0$, then $x_1$, then $x_2$, and so forth to $x_n$. In the bidirectional construction, on the other hand, the points are chosen in an order that represents successive subdivision of the path. This most easily explained if n is a power of 2, although the construction is easily modified for any other choice of n. For n=2k, the order of construction of the points is first $x_0$, then $x_n$, then $x_{n/2}$, then $x_{n/4}$, then $x_{3n/4}$, then $x_{n/8}$ and so forth until all of the points are constructed.

The initial point $x_0$ is chosen from the same initial probability density $p_0(x_0)$. The intermediate points are chosen using a conditional probability density, in which the choice of the desired point comes from a probability density $p_B$ that depends on the points that have already been chosen. The probability for a path $x_B=(x_0, x_1, x_2, \ldots, x_n)$ is given by the product $$p_B(x_B)=p_0(x_0)p_B(x_n)p_B(x_{n/2}|x_0,x_n)p_B((x_{n/4}|x_0,x_{n/2})$$
$$p_B(x_{3n/4}|x_{n/2},x_n)\ldots.$$

in which each term is the corresponding conditional probability.

The bidirectional construction is statistically equivalent to the direct construction if the probability densities for the two paths are equal, that is if $$p_B(x)=p_D(x).$$

for any path x. In this case, the dose d in said voxel is just the expectation over the bidirectional construction $$d=E[d(x_B)]=\Sigma p_B(x_B)d(x_B)$$

in which the sum is over all of the paths generated by the bidirectional construction. On the other hand, it may not be possible to perform a perfect bidirectional construction, satisfying $p_B(x)=p_D(x)$. Errors in the probability density can be corrected by insertion of a weight function w, defined by $$w(x)=p_D(x)/p_B(x)$$

for any path x. This resulting dose, following the method of importance sampling [22], is then $$d=E[w(x_B)d(x_B)]=\Sigma w(x_B)p_B(x_B)d(x_B)=\Sigma p_D(x_B)d(x_B)$$

which is equivalent to the total dose from the direct construction. Use of the bidirectional construction is advantageous because of the ability to position paths in the most important regions, but this must be balanced against the extra work involved in computation of the weight w.

As an example of the bidirectional construction, consider Brownian motion b(t) in one spatial dimension. Suppose that $b(t_0)=x_0$. Let $b(t_2)=x_2$. The value of $x_2$ could be chosen in a region of interest or it could be chosen according to the distribution for Brownian motion which is $$b(t_2)=b(t_0)+\text{sqrt}(t_2-t_0)\omega$$

in which ω is a standard gaussian random variable. The Brownian bridge formula says that for any t with $t_0<t_1<t_2$, $$b(t_1)=\alpha b(t_0)+\beta b(t_2)+\gamma v$$

in which $$\alpha=(t_2-t_1)/(t_2-t_0)$$

$$\beta=(t_1-t_0)/(t_2-t_0)$$

$$\gamma=\text{sqrt}((t_2-t_1)(t_1-t_0)/(t_2-t_0))$$

and v is a standard gaussian random variable, independent of ω. These formulas show how to correctly insert a point into the path of a particle undergoing Brownian motion at an intermediate time, if the positions at starting and ending times are already known. In this case, there is no error in the distribution of the points from the bidirectional construction, so that the weights are w=1.

Choice of the final point in the bidirectional construction could be based on several different strategies. For computation of dose distribution throughout the phantom or patient, the final point should be chosen over the entire voxel with a probability density that is (approximately) equal to that for the final point of the direct construction. As described above, this can be done exactly for Brownian motion. For computation of dose in a given voxel, the final point may be chosen in that voxel. For computation of dose in an ion chamber, the final point may be chosen in the small volume of the ion chamber. For dose distribution value at a single point y, the final point may be always taken to be y.

Note that dose deposition occurs at all points along a particle path, so that it may be necessary to take the "final" point in the bidirectional construction to be at different values of n along the path.

Multiple Voxel Sizes

A third new variance reduction method is to use voxels of multiple sizes in the computation. The reason for this is that through much of the patient, the density of the material is uniform. In these uniform regions, small voxels are inefficient because of the memory and the time spent in computing boundary crossings. Use of larger voxels in the uniform regions and smaller voxels in the nonuniform regions can considerably accelerate the computation. Acceleration of computational speed translates into the ability to simulate the transport of more particles for the same computation time, thus reducing error in the dose distribution.

Use of multiple voxel sizes is illustrated in FIG. 24. In step 24.1 a fine grid is constructed. In step 24.2 a multi-scale grid is constructed. The advantage of the multi-scale grid is that on large voxels the transport steps can be taken to be large, as in step 24.3. The dose distribution is recorded on the fine grid, as in step 24.4. This aspect of the invention may be seen by referring to FIGS. 19.1 showing the coarse grid with long steps and comparing it to FIG. 19.3 showing the fine grid with small steps.

Postprocessing

Postprocessing is a method for reducing the error in a dose distribution, without changing the Monte Carlo simulation. It is applied to the dose distribution after the radiation transport simulation is finished. By reducing the error through postprocessing, NXEGS requires simulation of fewer particles. Therefore postprocessing accelerates the Monte Carlo simulation, because it reduces the computational time required to achieve a specified level of accuracy, even though it does not speedup the simulation of particle transport. Postprocessing is described in step 2.8 of FIG. 2 and shown in more detail in FIG. 25.

This process is similar to that used in nonlinear image processing [8,9], and it is distinct from the linear filtering methods discussed in [15,16]. The difference between a linear method and a nonlinear method is paramount. As discussed below, linear filtering induces smoothing and oscillations (known as "Gibbs phenomenon") that distort the important, sharp transitions in the spatial distribution of radiation dose; nonlinear image processing does not involve any smoothing.

First, the dose array, consisting of dose values for each voxel, is input to the postprocessor in step 25.1. Then some information on the amplitude of the signal and noise is extracted in 25.2. Using this information, an image processing method is prepared in 25.3 and applied to the image in 25.4. The output from the postprocessing method is a postprocessed dose, in step 25.5, with reduced statistical error.

Examples of two types of nonlinear image processing methods (nonlinear filters and nonlinear diffusion) are described here. The first type of methods is that of nonlinear filters using a basis, such as the wavelet, Fourier or cosine basis. The filter parameters may be chosen based on the information that was extracted from the signal in step 25.2.

An example of a nonlinear filter is the Donoho-Johnstone soft thresholding [8]. For noisy signal $u_0$, the denoised signal u is given by $$u=Du_0 \quad (15)$$

in which, for any function w, the operator D acts on the coefficients of the (discrete) wavelet, Fourier or cosine transform by $$(Dw)\hat{} = \text{sgn}(w\hat{})(|w\hat{}|-t)^+ \quad (16)$$

$$t = \text{sqrt}(2 \log(n)) \gamma_1 \sigma / \text{sqrt}(n) \quad (17)$$

in which $w\hat{}$ and $(Dw)\hat{}$ are the wavelet, Fourier or cosine coefficients of w and Dw respectively, t is a threshold, the superscript + indicates the positive part (the thresholding), n is the number of data points (i.e. voxels) and the parameters $\gamma_1$ and $\sigma$ are chosen based on the noise properties of the noisy image $u_0$; i.e. $\sigma$ is the noise level in the image (dose) and $\gamma_1$ is a constant determined in [8].

The action of equation (16) is described as follows. Start by applying the wavelet, Fourier or cosine transform to the signal (i.e. the dose) w to obtain the set of transform coefficients $w\hat{}$. Then transform each coefficient as follows: Replace $w\hat{}$ by its absolute value $|w\hat{}|$. If $|w\hat{}|$ is larger than t, then replace it by $(|w\hat{}|-t)$; otherwise replace it by 0. Finally, multiply the result by −1, if $w\hat{}<0$.

In practice, the coefficient $\gamma_1$ may be chosen to optimize the noise reduction. The nonlinearity of this thresholding method, including the absolute value, the "sgn" function, the dependence of the parameter t on the noise level $\sigma$ in (17), and the use of t as a threshold in (16), distinguishes this nonlinear filter from the linear filtering methods of [15] and [16].

The action of this nonlinear filter is best understood by comparison to a linear filter. In general an operator D is defined to be linear if it satisfies the following two equations:

$$D[f+g]=D[f]+D[g]$$

$$D[cf]=cD[f]$$

for any two functions f and g and any constant c. If D does not satisfy these two equations, then it is nonlinear. Application of a linear filter involves multiplication of the coefficients $w\hat{}(k)$ by a function $\phi(k)$; i.e., $$(Dw)\hat{}(k) = \phi(k) w\hat{}(k). \quad (18)$$

For example, the simplest filter consists of a cutoff in wavenumber space above a certain value k*, for which $$\phi(k)=1 \text{ if } |k|<k^*$$

$$\phi(k)=0 \text{ if } |k|>k^*. \quad (19)$$

The linear filter has the problem of Gibbs phenomena. If the dose distribution contains any sharp features, across which there is a rapid change in the dose, then a linear filter will induce oscillations on either side of the transition. The soft-thresholding method of Donoho-Johnstone minimizes the Gibbs phenomena, by correctly choosing where to make the cutoff in k and by moving the entire spectrum down, rather than simply cutting it off.

This is illustrated in FIGS. 26.1–26.4. Consider a known "exact" dose, as illustrated in FIG. 26.1, and a corresponding "noisy" dose produced by Monte Carlo simulation in FIG. 26.2. Application of a linear filter removes some of the oscillatory noise from the dose but also produces new oscillations near regions where the dose has a sharp transition, as shown by the arrows in FIG. 26.3. The non-linear filtering method described above eliminates most of these spurious oscillations, as shown in FIG. 26.4.

Another type of nonlinear image processing is based on application of partial differential equations (PDE) for nonlinear diffusion. This is an example of an image processing method that is not a filter. First consider the simple example of application of linear diffusion to an image.

$$\partial u / \partial t = \text{div}((\text{grad } u)) - \lambda(u - u_0) \text{ for } t > 0$$

$$u = u_0 \text{ at } t = 0. \quad (20)$$

In this equation $u_0$ is the noisy image (e.g., the dose distribution), and $u(t)$ is a smoothed image, in which the "time-like" variable t acts as a smoothing parameter. The final denoised image (e.g., the dose distribution) is the limit of $u(t)$ as $t \to \infty$. This has the effect of smoothing out the small oscillations in the solution that are caused by statistical noise. The problem with this method is that it performs too much smoothing, so that a region of rapid transition gets spread out.

An alternative that retains sharpness of narrow transition regions is the use of nonlinear diffusion equations. A specific choice of nonlinear PDE is the Osher-Rudin equation [9]. Start with the initial, noisy dose distribution $u_0$ and solve the following equation forward in time:

$$\partial u / \partial t = \text{div}((\text{grad } u)/|\text{grad } u|) - \lambda(u - u_0) \text{ for } t > 0$$

$$u = u_0 \text{ at } t = 0. \quad (21)$$

The limiting value as t gets large is the resulting, denoised solution. The coefficient $\lambda$ is a parameter that is chosen based on the amount of noise in the signal $u_0$. The original, noisy signal is both the initial data and a driving force in the PDE. As described in [9], insight into the effect of nonlinear diffusion as a denoising method comes from relating it to the following variational quantity:

$$V[u] = \int |\text{grad } u| + \lambda (u-u_0)^2 dx. \quad (22)$$

For example, in the limit $t \to \infty$, the solution $u(t)$ of (21) approaches the function that minimizes $V[u]$. In addition the time dynamics of u, as prescribed by (21), follows the path (in the space of functions u) of steepest descent for $V[u]$.

Nonlinear diffusion is illustrated in FIGS. 27.1–27.4. As in FIGS. 26.1–26.4, consider a known "exact" dose, as illustrated in FIG. 27.1 and a corresponding "noisy" dose produced by Monte Carlo simulation in FIG. 27.2. Application of a linear diffusion removes most of the oscillatory noise from the dose but also incorrectly smoothes out sharp transitions in the dose, as shown in FIG. 27.3. The nonlinear diffusion method described above eliminates most of this smoothing, as shown in FIG. 27.4.

In the nonlinear methods described above, a measure of the statistical error in the dose distribution is required. This can be computed by the use of batches, as in EGS4. For a computation with a set of N particles, divide the particles into n batches, each of which contains N/n particles. Since each of these gives an estimate of the dose distribution, the variance in the dose distribution can be measured by calculation of the variance among these n values. In this way the value of $\sigma$ above is computed, for determination of the parameter t in (17) or as a guide to choice of the parameter $\lambda$ in (21).

New Transport Methods

NXEGS employs several new transport methods in order to increase the accuracy of the transport computation. These include zombie transport, Molière tabulation and the uniform method.

Zombie Transport

"Zombie transport" is the name that is used to describe a new method for energy deposition of particles that reach the energy cutoff. The new method is illustrated graphically in FIG. 28, and the algorithm for it is detailed in FIG. 29. The EGS4 method is to deposit all of the energy of such a particle in the voxel where it is located when it first reaches the energy cutoff. The resulting statistical error is reduced in the zombie transport method by distributing the energy of the particle over some of the neighboring voxels. Starting from a point at which the energy cutoff has been reached, as in Step 29.1, the improved method used in NXEGS continues the path of the particle in a straight line, the direction of which is the direction of the particle when it reached the energy cutoff, as in Step 29.2. Let the particle energy E dissipate at a constant rate along this extended path (i.e. dE/dx=-c), in which the rate (c) is determined by the material cross section, as in Step 29.3. The constant c is changed to a different constant, denoted c', if the particle crosses into a voxel with a different material or a different density of the same material. The length of the extended particle path is determined by the length at which the energy is all used up (i.e. E=0). Six voxels are shown in FIG. 28, with voxel 1 being the initial voxel at which the particle reached the cut-off energy (as specified in EGS4). The extended path goes through voxels 2–6. The energy deposited in each voxel is the energy that is dissipated in the voxel; i.e., the energy deposited in the nth voxel is $E_n$=c d, in which d is the length of the portion of the extended path that lies in the nth voxel, as in Step 29.4.

In a medium with very small density (such as air), the statistical errors in the energy distribution as calculated using EGS4 are magnified in the dose, since the dose is the energy deposition divided by the density. In these regions, zombie transport significantly reduces the statistical error in the dose.

Uniform Transport Method and Molière Tabulation

The uniform transport method, illustrated in FIGS. 30 and 30a, is a new method for electron transport in which a single transport step corresponds to a fixed number of elastic scatterings. The term uniform implies a fixed number of elastic scatterings represented by a single Molière scattering event. This is in contrast to EGS4 for which a single step corresponds to a maximum amount of energy loss. In both NXEGS and EGS4, a step may be interrupted by occurrence of a discrete events such as Bremstrahlung emission, Möller scattering, Bhabha scattering and annihilation.

In the uniform method, all of the discrete scattering cross sections are tabulated to get the total cross section per unit path length for each type of discrete event as a function of particle energy, in Step 30.1. For each type of discrete event, there is one table for each material in the phantom/patient. Density fluctuations in the material are accounted for by a scaling of the total cross section.

Use of a transport step that consists of a fixed number of elastic scatterings allows for tabulation of the Molière scattering cross section as well. The resulting table gives the path length as a function of the particle energy corresponding to the fixed number of elastic scattterings. At the end of each particle step a scattering direction is determined, in Step 30.2.

In the uniform method, boundary crossing is handled differently than in EGS4 and PRESTA. The particle path is continued beyond the boundary, but the length of the path beyond the boundary is scaled according to the local density in the region, in Step 30.3.

From the tabulated cross sections for each type of discrete scattering, the probability of a discrete scattering for a given transport step is extracted. Based on a random decision with this probability, the particle is scattered, with position and other scattering variables (e.g., direction, energy loss and new particle creation) that are randomly chosen using the full scattering cross section. This is performed for each type of discrete scattering, in Step 30.4.

Finally, a point along the path is chosen (either deterministically or randomly), at which the choice of Molière scattering angle is made using the cross section at that point, as in FIG. 30.5.

FIG. 30a represents graphically the discrete event which may or may not occur and the Molière scattering which is always simulated for each transport step. The method simulates the transport of electrons using a Monte Carlo calculation and, for a given energy of a simulated particle, determines a step size in the Monte Carlo calculation to correspond to a fixed number of elastic scatterings. The step size is between an initial and end position (see FIG. 30a) and the particle path is a straight path between said initial and end positions. Next, one determines whether a discrete event occurs along said particle path based on the cross section of the particle within the material through which the particle path traverses. If a discrete event does not occur along the particle path, then a first intermediate point is randomly selected between the initial position and the end position along the particle path. A scattering angle at the first intermediate point is determined based on a tabulated cross section of the material existing at the first intermediate point. A Molière scattering event is simulated at the first intermediate point with the determined scattering angle. The Molière scattering event corresponds to the fixed number of elastic scatterings. The scattering angle determines a new end point for the particle path. If the particle path crosses a voxel boundary, the Molière scattering event or the discrete event may take place within the initial voxel or an adjacent voxel (where the end point may be located), and the appropriate cross sections are taken from the material properties where the event takes place.

In addition to the Molière scattering event, energy loss is simulated along said particle path using a continuous slowing down approximation which includes an exponential function of energy dE/dt=-kE where k is a constant dependent on the material through which the particle path traverses and E is a simulated particle energy.

If a discrete event does occur along said particle path, then one randomly selects a discrete point along the particle path at which the discrete event occurs, and determines a new particle path which is a straight line path extending from the discrete point to a final point such that the fixed number of elastic scatterings takes place between the initial point and the final point, and the direction of the new particle path is determined by the scattering angle of the discrete event at the discrete point. Further, one randomly selects a second intermediate point on a line segment between the initial and discrete points or between the discrete and final points, and perform the Molière scattering as described above.

Speed and Accuracy

NXEGS provides several alternatives for managing the tradeoff between speed of the computation and accuracy of the resulting dose distribution. For a given simulation, in step 31.1, the simulation can be run with several alternative controls for when it should stop, described in steps 31.2, 31.3 and 31.4. For the first method in step 31.2, a fixed number of source particles is prescribed. Since each source particles generates a number of secondary particles, this is referred to as a shower or history. An alternative method, in step 31.3, allows specification of the required relative accuracy. The third alternative, in step 31.4, allows specification of the estimated process time. At least 10,000 particles are simulated in either of these alternatives. In each case, the NXEGS simulation system is run, as in 31.5. At regular intervals, achievement of the simulation goals is checked, in step 31.6. If they have been met, the computation is stopped in 31.7, but, if not, the computation is continued by returning to step 31.5.

The final result of the simulation is the dose distribution in the phantom/patient.

In conformance with the EGS4 formulation, the NXEGS simulation described and claimed herein treats the electrons (and positrons) as well as the photons (x-rays) as "particles" for the purposes of the Monte Carlo calculation. Thus in the appended claims, the terms "particles" or "radiation" are intended to encompass, in both cases, all types of radiation emanating from the radiation source such as electrons (and positrons) as well as the photons (x-rays).

Appendix 1. Calibration Data

The NXEGS beam commissioning system is designed to commission clinical beams for use in the NXEGS Monte Carlo dose simulation system. The data required for photon beam commissioning is very similar to that used by non-Monte Carlo methods, such as Clarkson or FFT/superposition convolution. This data is of three types: general data on the therapy unit, dose scan data and non-scanning dose factors.

I. General Data

The following general data is required:
1. Manufacturer, Model, and Year of Manufacture of Unit.
    Example: Varian Linac 2100C/D (1997)
2. Geometric Parameters (dimensions) for the Unit.
    Distance from source/target to the upper surfaces of the upper and lower jaws, and to isocenter.
    Jaws thickness
    Jaws material IA. Data Specific to the Photon Beam
1. Parameters of the Wedge.
    Geometrical dimensions (coordinates of all vertices, for example)
    Distance from the source/target
    Orientation during measurements: (a) flat face toward source/target or phantom; (b) orientation in the plane perpendicular to the beam
    Material
2. Parameters of the Block Tray
    Geometrical dimensions
    Distance from the source/target
    Composition/material
        Example: The composition of steel might be (steel [1.0000]=Fe[0.9807]+Mn[0.0130]+C[0.0023])

IB. Data Specific to the Electron Beam
1. Parameters for each Electron Applicator ("Scraper")
    Geometrical dimensions (outer and inner x- and y-sizes, thickness)
    Distance from the source/target
    Material
2. X-ray collimator field sizes (at SAD), for each Beam Energy and Cone.

II. Absolute Calibration Data and Conditions

The following information is required for each beam energy for the photon beam and for each beam energy and each cone for the electron beam. For the photon beam, a reference point without contamination artifacts (reference depth equal to 10 cm) is recommended.
    Setup type (SAD or SSD)
    Location of the reference point (specified by 2 numbers).
        SAD setup: SAD and source-to-chamber distance
        SSD setup: SSD and reference depth.
    Reference field size (10×10 or 15×15 is recommended).
        SAD setup—at SAD, SSD setup—at SSD.
    Calibration factor (dose in [cGy/MU] at the reference point for the reference field size).

III. Photon Beam Data—Dose Scans

The following data is needed for each photon beam energy at the nominal SSD. Additional data may be taken at other SSD's.

1. Central Axis Depth Dose Scans—Open Fields
    This data consists of the dose along the central axis (as a function of depth) for each of a range of square field sizes.
    Recommended square field sizes (cm): 4×4, 5×5, 7×7, 10×10, 12×12, 15×15, 20×20, 25×25, 30×30, and max. field size. Additional field sizes may be measured.
    Recommended depth increment along the central axis: 1–2 mm.

2. Diagonal Profile Scans
    This data consists of the dose along the diagonal (in the plane perpendicular to the beam central axis) for the maximal field size for each of a range of depths. At least one SSD value is required.
    Recommended depths (cm): dmax, 0.0, 0.5, 1.0, 2.0, 3.0, 5.0, 7.0, 10.0, 15.0, 20.0, 25.0, and 30.0. Additional depths may be measured.
    Recommended scan increment along the diagonal: 1–2 mm.

3. Open Field Aligned Profile Scans
    This data consists of the dose on a line through the beam center and along an axis direction (in the plane perpendicular to the beam central axis) for each combination of a range of depths and field sizes.
    Recommended square field sizes (cm): 5×5, 10×10, 15×15, 20×20, 25×25, 30×30, and max. field size. Additional depths and field sizes may be measured.
    Recommended depths (cm): dmax, 0.0, 5.0, 10.0, 15.0, 20.0, 25.0, and 30.0.
    Recommended scan increment along the axis 1–2 mm.

4. Wedged Field Aligned Profile Scans (For One Wedge)
    This data consists of the dose on a line through the beam center and along an axis direction (in the plane perpendicular to the beam central axis) for each combination of a range of depths and field sizes.
    Recommended square field sizes (cm): 5×5, 10×10, 15×15, 20×20, and max. field size. Additional depths and field sizes may be measured.
    Recommended depths (cm): dmax, 0.0, 5.0, 10.0, 15.0, 20.0, 25.0, and 30.0.
    Recommended scan increment along the axis 1–2 mm.

IV. Photon Beam Data—Non-Scanning

The following dose factors are needed for each photon beam energy at the nominal SSD. A reference depth without contamination artifacts (10 cm) is recommended for the beam data (field size factors and wedge factors).

1. In-Air Output Factors
    These are measured at isocenter for each of the following fields:
    Square fields of size (cm) 4×4, 5×5, 6×6, 7×7, 8×8, 10×10, 12×12, 15×15, 20×20, 25×25, 30×30, 35×35, and max. field size.
    Rectangular fields with x-field size equal to 10 cm, and with y-field size equal to 4, 5, 6, 7, 8, 10, 12, 15, 20, 25, 30, 35, and max. field size.
    Rectangular fields with y-field size equal to 10 cm, and with x-field size equal to 4, 5, 6, 7, 8, 10, 12, 15, 20, 25, 30, 35, and max. field size.

2. In-Water Output Factors
    This is the ratio of the output at the reference point for a given field size to that for the reference field size. The ratio is measured for the following range of square field sizes (cm): 4×4, 5×5, 7×7, 10×10, 12×12, 15×15, 20×20, 25×25, 30×30, 35×35, . . . , (max. field size)×(max. field size).

3. Wedge Factors (in Water)

This is the ratio of the output at the reference point in the presence of the wedge to the output without the wedge. Recommended field sizes are 4×4, 5×5, 6×6, 7×7, 8×8, 10×10, 12×12, 15×15, 20×20, 25×25, 30×30, 35×35, . . . , (max. field size)×(max. field size).

4. Block Tray Transmission Factor

This is the ratio of the beam intensity coming out of the tray to that going in. In addition, specify whether or not the block tray was in place when the other measurements were being made.

V. Electron Beam Data

The following data is needed for each electron beam energy and cone.

1. Central Axis Depth Dose Scan

This data consists of the dose along the central axis (as a function of depth). Data for a SSD equal to SAD is required. Recommended depth increment is 1 mm. Required range is from 0 to Rp+10 cm.

2. Open Field Aligned Profile Scans

Crossplane profile scans are required. Inplane profile scans are optional. Data for two SSD's (nominal and extended) is required.

Minimum is that two major axis scans are required. First at depth between 0.5 cm and dref/2. Second one below Rp+2 cm depth.

Recommended depths (cm): 0.5, 1.0, 2.0, 3.0, . . . , dmax, Rp+2, Rp+10 (cm).

Recommended scan step 2 mm.

3. Diagonal Profile Scans

One diagonal profile scan is required, two (45 and 135 degrees) are recommended at two depths.

Recommended depths: dmax/2 (or dref/2 by TG51 definition of the reference depth), Rp+2 (cm).

SSD equal to SAD.

Recommended scan step 2 mm.

4. Absolute Output Factors (in [cGy/MU])

Absolute dose at 4 SSDs at the reference depth for the given energy and cone are required. Recommended SSDs are 100, 105, 110, 115 cm. More SSDs recommended. List of SSDs should include those values that were used for profile measurements.

List of Abbreviations cGy. Centi-Gray.
dmax. Maximum value of dose.
dref Reference depth.
MU. Monitor Unit.
Rp. Practical Range
SAD. Source-axis distance.
Sp. Phantom scatter factor
SSD. Source-surface distance.

What is claimed is:

1. A method of commissioning a radiation source for use in radiation therapy comprising the steps of:

(a) inputting measured dose data into a data processor, said measured dose data derived from:
  (i) exposing a phantom to radiation from said source; and
  (ii) measuring the radiation dose to obtain a measured dose in said phantom resulting from the exposing step, said measured dose measured at a plurality of points within said phantom, at least some of said points being axial points located at positions along a substantially central axis of said radiation source and others of said points being transverse points located at positions along an axis transverse to the central axis, (b) performing a Monte Carlo simulation of said radiation source to determine a simulated dose at said plurality of points; and (c) modeling said radiation source using said simulated dose and said measured dose.

2. The commissioning method as recited in claim 1 wherein said modeling includes the step of obtaining a phase space distribution of particles leaving said source.

3. The commissioning method as recited in claim 1 wherein said modeling includes the step of obtaining a distribution of particle positions, directions and energies leaving said source.

4. The method as recited in claim 1 wherein radiation source is part of a treatment head which includes an accelerator emitting a beam of radiation and said step of measuring the radiation dose further comprises the step of:

measuring said radiation dose at said plurality of axial and transverse points for a plurality of beam energies from the accelerator.

5. The method as recited in claim 4 wherein said accelerator has at least one jaw or scraper which defines the beam exit size and wherein said step of measuring the radiation dose further comprises the step of measuring said radiation dose for a plurality of positions of said at least one jaw or scraper.

6. The method as recited in claim 5 wherein said treatment head includes a beam modifier and said step of measuring the radiation dose further comprises the step of measuring said radiation dose for at least one position of said beam modifier.

7. The method as recited in claim 6 wherein said beam modifier comprises a wedge.

8. The method as recited in claim 5 wherein said step of performing the Monte Carlo simulation comprises the steps of:

(a) defining at least one simulated sub-source comprising at least one of a focal source and non-focal source;

(b) dividing said at least one simulated sub-source into beamlets, each having a relatively small range of positions, energies and directions; and (c) for each of said beamlets, performing a Monte Carlo simulation to calculate said simulated dose at said plurality of points.

9. The method as recited in claim 8 wherein said step of modeling said radiation source comprises the steps of:

(a) combining a distribution of said simulated dose for each beamlet to form a transport matrix, each column of which defines a vector having values corresponding to said simulated dose for one of the beamlets;

(b) using said transport matrix and said measured radiation dose, calculating the amplitude of each beamlet for each of said simulated sub-sources; and (c) determining a phase space distribution for each simulated sub-source based on said calculated amplitudes.

10. The method as recited in claim 1 wherein said step of performing the Monte Carlo simulation comprises the steps of:

(a) defining at least one simulated sub-source comprising at least one of a focal source and non-focal source;

(b) dividing said at least one simulated sub-source into beamlets, each having a relatively small range of positions, energies and directions; and (c) for each of said beamlets, performing a Monte Carlo simulation to calculate said simulated dose at said plurality of points.

11. The method as recited in claim 10 wherein said step of modeling said radiation source comprises the steps of:
   (a) combining a distribution of said simulated dose for each beamlet to form a transport matrix, each column of which defines a vector having values corresponding to said simulated dose for one of the beamlets;
   (b) using said transport matrix and said measured radiation dose, calculating the amplitude of each beamlet for each of said simulated sub-sources; and
   (c) determining a phase space distribution for each simulated sub-source based on said calculated amplitudes.

12. The method as recited in claim 9 wherein said step of calculating the amplitude of each beamlet comprises using a constraint.

13. The method as recited in claim 12 wherein said constraint is applied as one of a penalization or a projection.

14. The method as recited in claim 1 wherein said radiation source comprises one of photons and electrons.

15. The method as recited in claim 14 wherein said photons include X-rays.

16. A method of commissioning a radiation source for use in radiation therapy comprising the steps of:
   (a) positioning a phantom to receive radiation from a said source;
   (b) exposing said phantom to radiation from said source;
   (c) measuring the radiation dose in said phantom resulting from the exposing step,
      said dose measured at a plurality of points within said phantom,
      at least some of said points being axial points located at positions along a substantially central axis of said radiation source and others of said points being transverse points located at positions along an axis transverse to the central axis,
   (d) performing a Monte Carlo simulation of said radiation source to determine a simulated dose at said plurality of points; and
   (e) modeling said radiation source using said simulated dose and said measured dose.

17. The commissioning method as recited in claim 16 wherein said modeling includes the step of obtaining a phase space distribution of particles leaving said source.

18. The commissioning method as recited in claim 16 wherein said modeling includes the step of obtaining a distribution of particle positions, directions and energies leaving said source.

19. The method as recited in claim 16 wherein radiation source is part of a treatment head which includes an accelerator emitting a beam of radiation and said step of measuring the radiation dose further comprises the step of:
   measuring said radiation dose at said plurality of axial and transverse points for a plurality of beam energies.

20. The method as recited in claim 19 wherein said accelerator has at least one jaw or scraper which defines the beam exit size and wherein said step of measuring the radiation dose further comprises the step of measuring said radiation dose for a plurality of positions of said at lease one jaw or scraper.

21. The method as recited in claim 20 wherein said treatment head includes a beam modifier and said step of measuring the radiation dose further comprises the step of measuring said radiation dose for at least one position of said beam modifier.

22. The method as recited in claim 21 wherein said beam modifier comprises a wedge.

23. The method as recited in claim 20 wherein said step of performing the Monte Carlo simulation comprises the steps of:
   (a) defining at least one simulated sub-source comprises at least one of a focal source and non-focal source;
   (b) dividing said at least one simulated sub-source into beamlets, each having a relatively small range of positions, energies and directions of said radiation; and
   (c) for each of said beamlets, performing a Monte Carlo simulation to calculate said simulated dose at said plurality of points.

24. The method as recited in claim 23 wherein said step of modeling said radiation source comprises the steps of:
   (a) combining a distribution of said simulated dose for each beamlet to form a transport matrix, each column of which defines a vector having component values corresponding to said simulated dose for one of the beamlets;
   (b) using said transport matrix and said measured radiation dose using said phantom, calculating the amplitude of each beamlet for each of said simulated sub-sources; and
   (c) determining a phase space distribution for each simulated sub-source based on said calculated amplitudes.

25. The method as recited in claim 23 wherein said step of performing the Monte Carlo simulation comprises the steps of:
   (a) defining at least one simulated sub-source comprises at least one of a focal source and non-focal source;
   (b) dividing said at least one simulated sub-source into beamlets, each having a relatively small range of positions, energies and directions of said radiation; and
   (c) for each of said beamlets, performing a Monte Carlo simulation to calculate said simulated dose at said plurality of points.

26. The method as recited in claim 25 wherein said step of modeling said radiation source comprises the steps of:
   (a) combining a distribution of said simulated dose for each beamlet to form a transport matrix, each column of which defines a vector having component values corresponding to said simulated dose for one of the beamlets;
   (b) using said transport matrix and said measured radiation dose using said phantom, calculating the amplitude of each beamlet for each of said simulated sub-sources; and
   (c) determining a phase space distribution for each simulated sub-source based on said calculated amplitudes.

27. The method as recited in claim 16 wherein said radiation source comprises one of photons and electrons.

28. The method as recited in claim 27 wherein said photons include X-ray.

29. A method of commissioning a radiation source comprising the steps of:
   (a) inputting; measured dose data into a data processor, said measured dose data derived from:
      (i) exposing said phantom to radiation from said source; and
      (ii) measuring the radiation dose to obtain a measured dose in said phantom resulting from the exposing step, said measured dose measured at a plurality of points within said phantom, at least some of said points being axial points located at positions along a substantially central axis of said radiation source and others of said points being transverse points located at positions along an axis transverse to the central axis, (b) performing a Monte Carlo simulation of said radiation source to determine a simulated dose at said plurality of points; and (c) modeling said radiation source using said simulated dose and said measured dose.

30. The commissioning method as recited in claim 29 wherein said modeling includes the step of obtaining a phase space distribution of particles leaving said source.

31. The commissioning method as recited in claim 29 wherein said modeling includes the step of obtaining a distribution of particle positions, directions and energies leaving said source.

32. The method as recited in claim 29 wherein radiation source is part of a treatment head which includes an accelerator emitting a beam of radiation and said step of measuring the radiation dose further comprises the step of:

measuring said radiation dose at said plurality of axial and transverse points for a plurality of beam energies from the accelerator.

33. The method as recited in claim 32 wherein said accelerator has at least one jaw or scraper which defines the beam exit size and wherein said step of measuring the radiation dose further comprises the step of measuring said radiation dose for a plurality of positions of said at least one jaw or scraper.

34. The method as recited in claim 33 wherein said treatment head includes a beam modifier and said step of measuring the radiation dose further comprises the step of measuring said radiation dose for at least one position of said beam modifier.

35. The method as recited in claim 34 wherein said beam modifier comprises a wedge.

36. The method as recited in claim 33 wherein said step of performing the Monte Carlo simulation comprises the steps of:

(a) defining at least one simulated sub-source comprising at least one of a focal source and non-focal source;

(b) dividing said at least one simulated sub-source into beamlets, each having a relatively small range of positions, energies and directions; and (c) for each of said beamlets, performing a Monte Carlo simulation to calculate said simulated dose within said plurality of points.

37. The method as recited in claim 36 wherein said step of modeling said radiation source comprises the steps of:

(a) combining a distribution of said simulated dose for each beamlet to form a transport matrix, each column of which defines a vector having values corresponding to said simulated dose for one of the beamlets;

(b) using said transport matrix and said measured radiation dose, calculating the amplitude of each beamlet for each of said simulated sub-sources; and (c) determining a phase space distribution for each simulated sub-source based on said calculated amplitudes.

38. The method as recited in claim 29 wherein said radiation source comprises one of photons and electrons.

39. The method as recited in claim 38 wherein said photons include X-rays.

40. A method of commissioning a radiation source comprising the steps of:

(a) positioning a phantom to receive radiation from a said source;

(b) exposing said phantom to radiation from said source, (c) measuring the radiation dose in said phantom resulting from the exposing step,
said dose measured at a plurality of points within said phantom,
at least some of said points located along a central axis of said radiation source and others of said points located along an axis transverse to the central axis, (d) performing a Monte Carlo simulation of said radiation source to determine a simulated dose at said plurality of points; and (e) modeling said radiation source using said simulated dose and said measured dose.

41. A method of modeling a radiation source, emitting radiation in the form of particles comprising the steps of:

(a) defining at least one simulated sub-source comprising one of a focal source and an extra focal source; each simulated sub-source having a relatively small interval of energy values and a relatively small interval of angular values, (b) performing a Monte Carlo simulation of particles leaving said at least one simulated sub-source to determine a simulated dose distribution; and (c) determining a phase space distribution of radiation leaving said at least one simulated sub-source using said simulated dose distribution and actual dose measurements.

42. The method as recited in claim 41 wherein said actual dose measurement is performed using a plurality of points, at least some of said points located at positions along a substantially central axis of said radiation source and others of said points located at positions along an axis transverse to the central axis.

43. A method of modeling a radiation source, emitting particles, in a linear accelerator used for radiation therapy comprising:

(a) defining at least one simulated sub-source from the group of simulated sub-sources consisting of a focal source and an extra focal source;

(b) performing a Monte Carlo simulation of radiation leaving said at least one simulated sub-source to determine a simulated dose distribution; and (c) determining a phase space distribution of radiation in an exit plane of said linear accelerator using said simulated dose distribution and actual dose measurements.

44. A method of performing radiation planning therapy comprising the steps of:

(a) performing a CT scan of a patient to provide patient-dependent information in a region of the patient to be treated;

(b) utilizing a source model based on dosimetry data which includes at least 10 dosimetry points;

(c) providing treatment head information concerning the characteristics and geometry of a treatment head; and (d) simulating a dose distribution using a Monte Carlo calculation based on a source model, the patient-dependent information and the treatment head information.

45. The method as recited in claim 44 wherein, said source model is provided by modeling a radiation source, in a linear accelerator used for radiation therapy, said modeling comprising the steps of:

(a) defining at least one simulated sub-source comprising at least one of a focal source and an extra focal source;

(b) performing a Monte Carlo simulation of radiation leaving said at least one simulated sub-source to determine a simulated dose distribution; and (c) determining said source model of radiation in an exit plane of said linear accelerator using said simulated dose distribution and actual dose measurements.

46. A method of defining a source model of an accelerator emitting radiation comprising the steps of:

(a) measuring the actual radiation dose distribution from said accelerator over a spatial volume defined within a phantom and for a plurality of accelerator energies;

(b) using Monte Carlo simulation to calculate a transport matrix, said transport matrix relating the actual radiation dose distribution to a source phase space distribution, said source phase space distribution defined as the probability distribution of the position, energy and direction of radiation from said accelerator;

(c) calculating said phase space distribution using said transport matrix and said actual radiation dose distribution, said phase space distribution defining said source model.

47. The method as recited in claim 46 wherein said step of measuring the actual radiation dose distribution from said accelerator is performed with a plurality of positions of jaw or scraper configurations of said accelerator.

48. A method of simulating radiation transport through a treatment head of a linear accelerator, said treatment head having at least one beam modifier, said method comprising the steps of:

(a) inputting into a data processor, parameters corresponding to a physical description of the treatment head and the at least one beam modifier included in the treatment head;

(b) simulating the introduction of particles from a source into the treatment head; and (c) performing simulated transport of particles through the at least one beam modifier in the treatment head through at least one of a Monte Carlo method or a throughput function.

49. A method of radiation treatment planning comprising the steps of:

(a) performing one of (1) commissioning a linear accelerator to obtain a source model or (2) using a source model from a linear accelerator that has already been commissioned, wherein said commissioning includes utilizing at least 10 dosimetry points;

(b) simulating one or more beams based on a source model;

(c) specifying a simulated treatment head, including (1) geometry and (2) material properties of at least one beam modifier for each beam;

(d) setting up a simulated patient or a simulated phantom;

(e) simulating particle transport through the simulated treatment head using at least one of a Monte Carlo method or a throughput function for each beam;

(f) simulating particle transport through the simulated patient or simulated phantom using said Monte Carlo method;

(g) calculating a radiation dose in the simulated patient or simulated phantom; and (h) providing an output of the calculated dose.

50. The method as recited in claim 49 further including the step of simulating a bolus as part of the simulated patient.

51. A method of radiation treatment planning comprising the steps of:

(a) simulating one or more beams based on a source model;

(b) specifying a simulated treatment head, including (1) geometry, (2) motion and (3) material properties of at least one beam modifier for each beam;

(c) setting up a simulated patient or a simulated phantom;

(d) simulating particle transport through the simulated treatment head using at least one of a Monte Carlo method or a throughput function for each beam;

(e) simulating particle transport through the simulated patient or simulated phantom using Monte Carlo method;

(f) calculation a radiation dose in the simulated patient or simulated phantom; and (g) providing an output of the calculated dose.

52. A method of specifying at least one beam modifier for use in Monte Carlo simulation of a particle motion through a treatment head which includes a radiation source and at least one beam modifier, said method comprising the steps of:

(a) inputting into a data processor a geometry specifying said at least one beam modifier by performing at least one of the following three steps:
    (i) for a beam modifier in the shape of a polyhedron, inputting the coordinates of each vertex of said polyhedron and specifying the edges of connecting vertices, and inputting the position and orientation of the polyhedron;
    (ii) for a beam modifier in the form of a multi-leaf collimator, inputting the number and size of each leaf; and
    (iii) for a beam modifier in the shape of a compensating filter, consisting of a flat side and a curved shape of arbitrary complexity opposite the flat side, inputting the height of the curved shape above each point of the flat side, and specifying whether the flat side points toward or away from the radiation source; and (b) inputting a type and density of material that constitutes said at least one beam modifier.

53. The method as recited in claim 52 further including at least one of the steps of:

(a) for said polyhedron, specifying multiple positions and orientations of said polyhedron to simulate motion; and (b) for said multi-leaf collimator, inputting a motion sequence of each leaf.

54. The method as recited in claim 53 further comprising the step of inputting the position and orientation of the at least one beam modifier within the treatment head as a function of time if the treatment head or at least one beam modifier is moving.

55. The method as recited in claim 52 further comprising the step of inputting the position and orientation of the beam modifiers within the treatment head as a function of time if the treatment head is moving.

56. A method of performing radiation planning therapy comprising the steps of:

(a) performing a CT scan of a patient to provide patient-dependent information in a region of the patient to be treated;

(b) providing treatment head information concerning the characteristics and geometry of a treatment head;

(c) simulating a dose distribution using a Monte Carlo calculation based on a source model, the patient-dependent information and the treatment head information; and (d) wherein, as part of step (b), the method include specifying at least one beam modifier for use in said Monte Carlo calculations of particle motion through said treatment head which includes a radiation source and said at least one beam modifier, said step of specifying including:
  (i) inputting into a data processor a geometry specifying said at least one beam modifier by performing at least one of the following three steps:
    (1) for a beam modifier in the shape of a polyhedron, inputting the coordinates of each vertex of said polyhedron and specifying the edges of connecting vertices, and inputting the position and orientation of the polyhedron;
    (2) for a beam modifier in the form of a multi-leaf collimator, inputting the number and size of each leaf; and
    (3) for beam modifier in the shape of a compensating filter, consisting of a flat side and a curved shape of arbitrary complexity opposite the flat side, inputting the height of the curved shape above each point of the flat side, and specifying whether the flat side points toward or away from the radiation source; and
  (ii) inputting a type and density of material that constitutes said at least one beam modifier.

57. The method as recited in claim 52 further comprising the steps of:
  specifying movement of said at least one beam modifier by the steps of:
    inputting a series of at least one of (1) positions and (2) orientations of said at least one beam modifier and a series of treatment time intervals during which at least one beam modifier remains in each position and orientation;
    moving at least one beam modifier corresponding to said inputted positions and orientations and for said treatment time intervals so as to simulate a moving beam modifier during a Monte Carlo simulation.

58. The method as recited in claim 57 further comprising the steps of randomly sampling the particles over said series of treatment time intervals.

59. The method as recited in claim 52 further comprising the steps of:
  specifying movement of said at least one beam modifier by the steps of:
    inputting a series of frames defined by specifying at least one of (1) positions and (2) orientations of said at least one beam modifier and a particle weight corresponding to each of said at least one of said frames;
    randomly selecting a frame for each of a plurality of simulated particles emitted from said radiation source; and
    applying said corresponding particle weight to each of said plurality of simulated emitted particle for use in said Monte Carlo simulation;
    whereby utilizing said particle weight simulates a time interval for each of said frames, and thus simulates the change of said at least one of the position and orientation of said at least one beam modifier so as to simulate moving said at least one beam modifier during the Monte Carlo simulation.

60. A method for computing the dose deposition due to particles whose energy is below a cutoff, as part of a Monte Carlo simulation, comprising the steps of:
  (a) determining that a given particle has reached a cutoff energy within a given voxel; and
  (b) for particles below the cutoff energy, performing the steps of:
    (i) extending the particle path in a straight path from the point at which the cutoff was reached in the direction of the particle motion at said point; and
    (ii) simulating a constant energy deposition rate using a rate constant along said straight path.

61. The method as recited in claim 60 wherein the step of extending the particle path includes extending the particle path through at least one additional voxel other than said given voxel.

62. The method as recited in claim 61 wherein a first rate constant is selected for said given voxel and a second, different rate constant is selected for said at least one additional voxel.

63. A method of simulating the transport of electrons using a Monte Carlo calculation comprising the steps of:
  (a) for a given energy of a simulated particle, determining a step size in the Monte Carlo calculation to correspond to a fixed number of elastic scatterings wherein said step size is between an initial and end position and the particle path is a straight path between said initial and end positions;
  (b) determining whether a discrete event occurs along said particle path based on the cross section of the particle within the material through which the particle path traverses;
  (c) if a discrete event does not occur along the particle path, then
    (i) randomly selecting a first intermediate point between the initial position and the end position along said particle path;
    (ii) determining a scattering angle at the first intermediate point based on a tabulated cross section of the material existing at the first intermediate point;
    (iii) simulating a Molière scattering event at the first intermediate point with the determined scattering angle, said Molière scattering corresponding to said fixed number of elastic scatterings; and
    (iv) said scattering angle determining a new end point for the particle path.

64. The method as recited in claim 63 wherein said particle path crosses a voxel boundary.

65. The method as recited in claim 63 further including the steps of:
  (a) simulating the deposition of energy along said particle path using a continuous slowing down approximation which includes an exponential function of energy $dE/dt = -kE$ where k is a constant dependent on the material through which said particle path traverses and E is a simulated particle energy.

66. The method as recited in claim 63, wherein if a discrete event does occur along said particle path, then performing the following steps:
  (a) randomly selecting a discrete point along the particle path at which the discrete event occurs;
  (b) determining a new particle path which is a straight line path extending from the discrete point to a final point such that said fixed number of elastic scatterings between said initial point and said final point, and the direction of said new particle path is determined by the scattering angle of the discrete event at the discrete point;
  (c) randomly selecting a second intermediate point on a line segment between the initial and discrete points or between the discrete and final points;

(d) determining a scattering angle at the second intermediate point based on a tabulated cross section of the material existing at the second intermediate point;

(e) simulating a Molière scattering event at the second intermediate point with the determined scattering angle, said Molière scattering corresponding to said fixed number of elastic scatterings; and (f) said scattering angle determining a new end point for the particle path.

67. A method for commissioning a source model for an electron beam wherein the source model includes a focal electron subsource and a focal photon subsource, both lying on the central axis of a linear accelerator, wherein said source model includes a sampling plane perpendicular to the central axis in which simulated electrons and photons are specified by their position r from the central axis and their energy E, wherein the position r defines an angle theta, and the position r is randomly selected and the particle is assigned a weight through fluence functions for the electron and photon subsources and the energy E is determined through energy spectra for the electron and photon subsources, said method comprising the steps of:

(a) selecting an initial estimate for:
  (i) positions of the electron and photon subsource along the central axis;
  (ii) parameters defining the energy spectra for the electrons and photons; and
  (iii) parameters defining the fluence functions for the electrons and photons; and (b) using the initial estimate, simulating a plurality of dose distributions, including output factors, percentage depth dose (PDD) curves, and dose profiles;

(c) comparing the simulated output factors to the measured output factors and determining an improved estimate for the positions of the electron and photon subsource along the central axis;

(d) comparing the simulated PDD curves to the measured PDD curves and determining an improved estimate for the parameters defining the energy spectra for the electrons and photons; and (e) comparing the simulated dose profiles to the measured dose profiles and determining an improved estimate for the parameters defining the fluence functions for the electrons and photons.

68. The method as recited in claim 67 wherein the source model is used in radiation therapy treatment planning and in which the simulation is performed using a Monte Carlo transport method in a treatment head and a pencil beam method in a phantom.

69. The method as recited in claim 67 further comprising the steps of using the improved estimates found in steps c) through e) as new initial estimates, repeating steps b) through e), at least one time.

70. The method as recited in claim 67 further comprising the steps of performing simulation of an additional plurality of dose distributions after at least one of steps c), d) and e).

71. The method as recited in claim 67 wherein the source model is further defined to include varying the direction of electrons emitted at the sampling plane resulting from a simulated scattering, in which the change in direction is randomly selected.

72. The method as recited in claim 71 wherein the change in direction is randomly selected from a gaussian density.

73. The method as recited in claim 67 wherein determining the improved estimates for the parameters in steps c), d) and e) includes performing a chi-square fit of the simulated output factors, PDD curves and dose profiles respectively.

74. A method for defining a source model for an electron beam wherein the source model includes the following:

(a) defining a focal electron subsource lying on the central axis of a linear accelerator;

(b) defining focal photon subsource lying on the central axis of the linear accelerator;

(c) defining a sampling plane perpendicular to the central axis;

(d) specifying fluence functions, which are functions of the position r from the central axis, for each of electrons and photons;

(e) specifying energy spectra for each of said electrons and photons;

(f) determining the direction of each of said electrons and photons by the straight line direction from the respective focal subsource location to a point in the sampling plane; and (g) specifying a scattering of electrons by varying the direction of said electrons from the determined direction from step f).

75. The method as recited in claim 74 wherein a quasi-random sequence is used in determining one or more of the following:

(a) a position in the sampling plane for said electrons and photons;

(b) an energy from the energy spectra for said electrons and photons; and (c) a scattering angle for electrons.

76. The method as recited in claim 75 in which the quasi-random sequence is one of the following:

(a) a Sobol sequence; and (b) a Halton sequence.

77. A method for commissioning a source model for a photon beam wherein the source model includes a focal photon subsource and a focal electron subsource, both lying on the central axis of a linear accelerator, and an extrafocal photon subsource lying on a plane perpendicular to the central axis, wherein said source model includes a sampling plane perpendicular to the central axis in which simulated electrons and photons are specified by their position r from the central axis and their energy E, wherein the position r defines an angle theta, and the position r is randomly selected and the particle is assigned a weight through fluence functions for the electron and photon subsources and the energy E is determined through energy spectra for the electron and photon subsources, said method comprising the steps of:

(a) determining the spatial distribution of said extrafocal photon subsource to fit output factors in air;

(b) performing Monte Carlo simulation of radiation transport for a plurality of beamlets, each of which corresponds to subset of energies and angles for said focal photon subsource or said focal electron subsource, and obtaining simulated dose values at each point of a phantom for which there are measured dose values; and (c) using a matrix of said simulated dose values in determining the spectrum and fluence for said focal photon subsource or said focal electron subsource to fit the measured dose values.

78. The method as recited in claim 77 in which the focal photon subsource and the focal electron subsource lie at the center of the target, the extrafocal subsource lies on the target, and the sampling plane is on the lower surface of the lower collimator jaws.

79. The method as recited in claim 77 in which the spatial distribution of the extrafocal photon subsource consists of a sum of gaussian distributions.

80. The method as recited in claim 77 in which effects of backscatter from the collimator are included by a weight factor that is bilinear in the jaw opening, for which the parameters are determined to fit the output factors in air.

81. The method as recited in claim 77 wherein the source model is further defined to include varying the direction of electrons emitted at the sampling plane resulting from a simulated scattering, in which the change in direction is randomly selected.

82. The method as recited in claim 81 wherein the change in direction is randomly selected from a gaussian density.

83. The method as recited in claim 77 in which the extrafocal photon subsource and the focal electron subsource have energy spectra that are independent of the particle direction, and the focal photon subsource has an energy spectrum that depends on the angle between the photon direction and the central axis.

84. A method for defining a source model for a photon beam wherein the source model includes the following:
   (a) defining a focal photon subsource lying on the central axis of a linear accelerator;
   (b) defining a focal electron subsource lying on the central axis of the linear accelerator;
   (c) defining an extrafocal photon subsource lying on a plane perpendicular to the central axis of the linear accelerator;
   (d) defining a sampling plane perpendicular to the central axis;
   (e) specifying fluence functions, which are functions of the position r from the central axis, for each of the electron and photon subsources;
   (f) specifying energy spectra for each of the electron and photon subsources;
   (g) selecting a point in the sampling plane for each electron from the focal electron subsource, each photon from the focal photon subsource and each photon from the extrafocal photon subsource;
   (h) selecting a point on the plane of the extrafocal photon subsource;
   (i) determining the direction of said photon from the focal photon subsource and said electron from the focal electron subsource by the straight line direction from the respective focal subsource location to the respective point in the sampling plane;
   (j) determining the direction of said photon from the extrafocal photon subsource by the straight line direction from said point on the plane of the extrafocal photon subsource to the respective point in the sampling plane; and
   (k) specifying a scattering of electrons by varying the direction of said electrons from the determined direction from step i).

85. A method of error reduction of Monte Carlo simulation radiation transport comprising the steps of:
   (a) calculating a dose distribution $f_S(x)$ using a first Monte Carlo simulation using a number, n, of particles and a random number sequence;
   (b) calculating a dose distribution $g_S(x)$ based on a simplified representation of the radiation transport using a second Monte Carlo simulation with said number of particles n and said random sequence;
   (c) calculating a dose distribution $g_L(x)$ based on said simplified representation using a third Monte Carlo simulation with a number of particles m where m is greater than n; and
   (d) reducing the error in the dose distribution $f_S(x)$ by using $f_S(x)-g_S(x)+g_L(x)$ as the error reduced dose distribution.

86. The method as recited in claim 85 wherein said first Monte Carlo simulation uses a fine grid in defining voxels for a treatment area and said second and third Monte Carlo simulations use a coarse grid.

87. The method as recited in claim 85 wherein said first Monte Carlo simulation uses an interaction or scattering cross section and said second and third Monte Carlo simulations use a simplified interaction or scattering cross section.

88. The method of error reduction in radiation transport comprising the steps of:
   (a) performing a Monte Carlo simulation transport calculation to determine a dose distribution in a region of interest; and
   (b) reducing the error of said dose distribution using control variates.

89. A method of accelerating computation of dose distributions in a target area comprising the steps of:
   (a) mathematically constructing a fine grid throughout regions of said target area where the density of the target area is non-uniform;
   (b) mathematically constructing a coarse grid throughout regions of said target area where the density of the target area is uniform; and
   (c) performing a Monte Carlo simulation of the dose distribution using transport steps defined within said coarse and fine grids wherein in said coarse grid, larger transport steps are used relative to transports steps used in said fine grid.

90. The method as recited in claim 89 further comprising the steps of recording the dose distribution for said coarse grid on said fine grid.

91. A method of improving the accuracy of a Monte Carlo simulation in radiation treatment planning for particle transport within a target region of interest comprising the steps of:
   (a) selecting an end point position within the target region of interest;
   (b) selecting an initial position outside of the target region;
   (c) selecting at least one intermediate point on a particle path connecting the initial and end positions randomly chosen using a bi-directional probability distribution;
   (d) repeating step c) for multiple particle paths having different intermediate points; and
   (e) calculation the total dose within the target region resulting from the summation or average of the doses of the multiple paths.

92. The method as recited in claim 91 wherein step e) includes:
   summing the dose resulting from each path with a weighting factor determined by an importance sampling method.

93. The method as recited in claim 91 wherein step e) includes:
   summing the dose resulting from each path with a weighting factor determined by pD/pB,
   where pD is the probability of selecting a path from a direct construction starting from the initial position and subsequently through each of the at least one intermediate points and ending at the end point, and wherein pB is the probability of selecting a path starting from the initial position and the end positions and subsequently through each of the at least one intermediate positions.

94. The method as recited in claim 91 further comprising the step of:

(f) repeating steps (a)–(e) for different end point positions.

95. A method of improving the simulation of a Compton scattering event in computing dose distributions of radiation resulting from Compton scattering events comprising the steps of:

(a) performing a Monte Carlo transport simulation using an electromagnetic source;

(b) determining Compton scattering events along a simulated transport path of said radiation in a treatment region of interest; and (c) at each Compton scattering event, simulating the generation of a plurality of electrons distributed along the transport path.

96. The method as recited in claim 95 further comprising the step of assigning weights 1/m to each of said electrons, where m is the number of electrons distributed along the path.

97. The method as recited in claim 95 further comprising the step of randomly distributing the plurality of electrons along the transport path in a region adjacent to said Compton event.

98. The method as recited in claim 97 wherein said adjacent region is immediately before said Compton event.

99. The method as recited in claim 97 wherein said adjacent region is immediately after said Compton event.

100. The method as recited in claim 97 wherein said adjacent region is immediately before and immediately after said Compton event.

101. The method as recited in claim 95 wherein the electrons are distributed in a step size equal to the mean free path (MFP) multiplied by a weight fraction wherein said position along the path has a random offset variable associated therewith.

102. A method for error reduction of Monte Carlo simulation for radiation transport by postprocessing the resulting energy or dose distribution using at least one of nonlinear filtering or image processing techniques.

103. The method as recited in claim 102 using one of the following techniques:

filtering applied to solution in which the filtering level is chosen based on the properties of the solution; and nonlinear diffusion techniques.

104. The method as recited in claim 102 wherein the radiation transport is applied to radiation therapy and wherein the method further uses one of the following techniques:

(a) a Donoho-Johnstone soft thresholding;

(b) a Osher-Rudin equation; and (c) a local cosine method.

* * * * *